(12) United States Patent
Lund et al.

(10) Patent No.: US 8,084,035 B2
(45) Date of Patent: Dec. 27, 2011

(54) CD38 MODULATED CHEMOTAXIS

(75) Inventors: Frances E. Lund, Saranac Lake, NY (US); Troy D. Randall, Saranac Lake, NY (US); Santiago Partida-Sanchez, Galloway, OH (US)

(73) Assignee: Trudeau Institute, Inc., Saranac Lake, NY (US)

( * ) Notice: Subject to any disclaimer, the term of this patent is extended or adjusted under 35 U.S.C. 154(b) by 0 days.

(21) Appl. No.: 12/703,062

(22) Filed: Feb. 9, 2010

(65) Prior Publication Data

US 2010/0297148 A1 Nov. 25, 2010

Related U.S. Application Data

(60) Division of application No. 11/058,924, filed on Feb. 15, 2005, now Pat. No. 7,695,933, which is a continuation-in-part of application No. 09/982,616, filed on Oct. 17, 2001, now Pat. No. 6,955,884.

(60) Provisional application No. 60/241,065, filed on Oct. 17, 2000.

(51) Int. Cl.
*A61K 39/00* (2006.01)
*A61K 39/385* (2006.01)
*G01N 33/53* (2006.01)
*C07K 14/52* (2006.01)

(52) U.S. Cl. ....... 424/185.1; 424/193.1; 435/6; 435/7.1; 530/350

(58) Field of Classification Search .................. None
See application file for complete search history.

(56) References Cited

U.S. PATENT DOCUMENTS 5,958,723 A 9/1999 Abramowitz et al.

FOREIGN PATENT DOCUMENTS

| WO | 94/17184 A1 | 8/1999 |
| WO | 02/32288 A2 | 4/2002 |

OTHER PUBLICATIONS

Mikayama et al. PNAS, 1993. 90: 10056-10060.*
Burgess et al J Cell Biol. 111:2129-2138, 1990.*
Wang et al. JBC, 2001 276:49213-49220.*
Abdallah M.A., Biellmann J.F., Nordstrom B., Branden C.I. The conformation of adenosine diphosphoribose and 8-bromoadenosine diphosphoribose when bound to liver alcohol dehydrogenase. Eur. J. Biochem. 1975;50:475-481.

(Continued)

*Primary Examiner* — Michail Belyavskyi
(74) *Attorney, Agent, or Firm* — Kenyon & Kenyon LLP

(57) ABSTRACT

The present invention relates to methods for modulating the migratory activity of cells expressing CD38 for the treatment of disorders including, but not limited to, inflammation, ischemia, asthma, autoimmune disease, diabetes, arthritis, allergies, infection with pathogenic organisms, such as parasites, and transplant rejection. Such cells include, for example, neutrophils, lymphocytes, eosinophils, macrophages and dentritic cells. The invention further relates to drug screening assays designed to identify compounds that modulate the ADP-ribosyl cyclase activity of CD38 and the use of such compounds in the treatment of disorders involving CD38 modulated cell migration. Additionally, the invention relates to the isolation and characterization of a CD38 homologue from the parasitic flatworm, *Schistosoma mansoni*.

14 Claims, 37 Drawing Sheets

Figure 1:
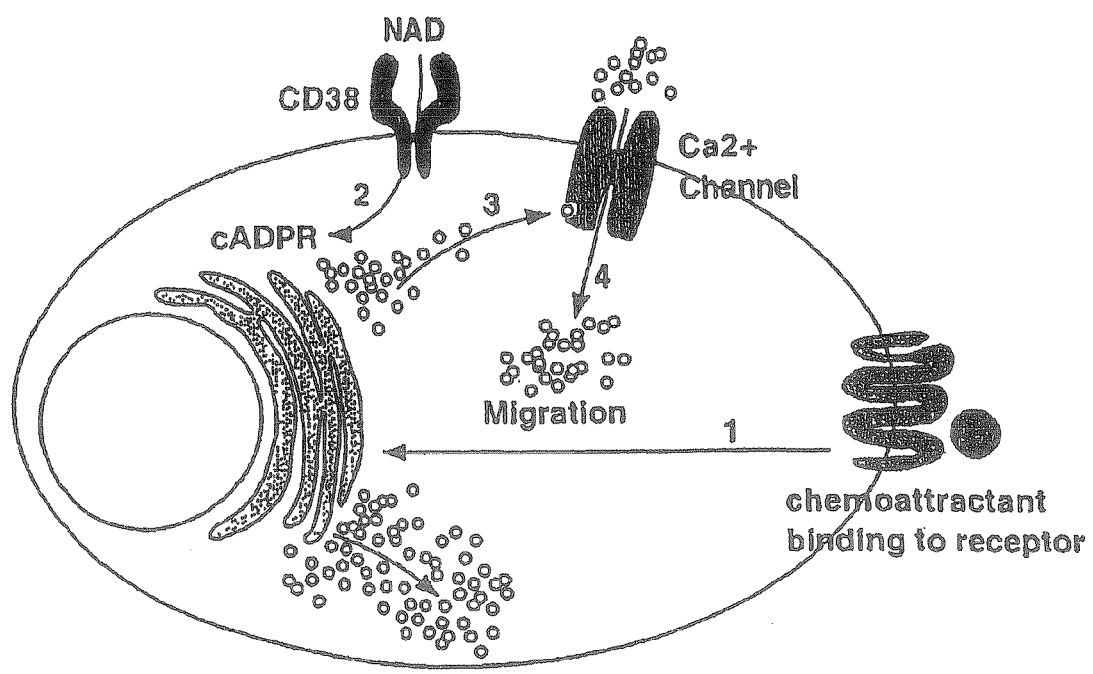

Normal cellular response to chemoattractant signaling.

OTHER PUBLICATIONS

Aarhus R., Graeff R.M., Dickey D.M., Walseth T.F., Lee H.C. ADP-ribosyl cyclase and CD38 catalyze the synthesis of a calcium-mobilizing metabolite from NADP. J. Biol. Chem. 1995;270:30327-30333.

Augustin A., Muller-Steffner H., Schuber F. Molecular cloning and functional expression of bovine spleen ecto-NAD+ glycohydrolase: structural identity with human CD38. J. Biochem. 2000;345:43-52.

Baggiolini M., Walz A., Kunkel S.L. Neutrophil-activating peptide-1/interleukin 8, a novel cytokine that activates neutrophils. J. Clin. Invest. 1989;84:1045-1049.

Berthelier V., Tixier J.M., Muller-Steffner H., Schuber F., Deterre P. Human CD38 is an authentic NAD(P)+ glycohydrolase. Biochem. J. 1998;330:1383-1390.

Brobnstein I., Fortin J.J., Voyta J.C., Juo R.R., Edwards B., Olesen C.E., Lijam N., Kricka L.J. Chemiluminescent reporter gene assays: sensitive detection of the GUS and SEAP gene products. Biotechniques 1994;17:172-174, 176-177.

Cakir-Kiefer, C. et al, "Unifying Mechanism for Aplysia ADP-ribosyl cyclase and CD38/NAD+ glycohydrolases", Biochem. J. (2000) vol. 349, pp. 203-210.

Clapper D.L., Walseth T.F., Dargie P.J., Lee H.C. Pyridine nucleotide metabolites stimulate calcium release from sea urchin egg microsomes desensitized to inositol trisphosphate. J. Biol. Chem. 1987;262:9561-9568.

Cockayne D.A., Muchamuel T., Grimaldi J.C., Muller-Steffner H., Randall T.D.., Lund F.E., Murray R., Schuber F., Howard M.C. Mice deficient for the ecto-nicotinamide adenine dinucleotide glycohydrolase CD38 exhibit altered humoral immune responses. Bloo 1998;92:1324-1333.

Day T.A., Haithcock J, Kimber M, Maule A.G.,. Functional ryanodine receptor channels in flatworm muscle fibres. Parasitology 2000; 120:417-422.

Day T.A. Maule A.G., Shaw C., Halton D.W., Moore S., Bennett J.L., Pax R.A. Platyhelminth FMRFamide-related peptides (FaRPs) contract Schistosoma mansoni (Trematoda; Digenea0 muscle fibres in vitro. Parasitology 1994; 109:455-459.

Day T.A., Bennett J.L., Pax R.A. Serotonin and its requirement for maintenance of contractility in muscle fibres isolated from Schistosoma mansoni. Parasitology 1994; 108:425-432.

Day T.A., Orr N., Bennett J.L., Pax R.A. Voltage-gated currents in muscle cells of Schistosoma mansoni. Parasitology 1993; 106:471-477.

Deaglio, S. et al., "Human CD38 (ADP-Ribosyl Cyclase) Is a Counter-Receptor of CD31, an Ig Superfamily Member", Immuno. J. vol. (1998) vol. 160 pp. 395-402.

Fernandez J.E., Deaglio S., Donati D., Beusan I.S., Corno F., Aranega A., Forni M., Falini B., Malavasi F. Analysis of the distributing of human CD38 and of its ligand CD31 in normal tissue. J. Biol. Regul. Homeost. Agents 1998;12:81-91.

Frohman M.A., Dush M.K., Martin G.R. Rapid production of full-length cDNAs rare transcripts; amplification using a single gene specific oligonucleotide primer. Proc. Natl. Acad. Sci. USA 1988;85:8998-9002.

Gadangi P., Longaker M., Naime D., Levin R.J., Recht P.A., Montesinos M.C., Buckley M.T., Carlin G., Cronstein B.N. The anti-inflammatory mechanism of sulfasalazine is related to adenosine release at inflamed sites. J. Immun. 1996;156:1937-1941.

Galione A., White A., Wilmott N., Turner M., Potter B.V., Watson S.P. cGMP mobilizes intracellular Ca2+ in sea urchin eggs by stimulating cyclic ADP-ribose synthesis. Nature 1993;365:456-459.

Galione A., Lee H.C., Busa W.B. Ca(2+)-induced Ca2+ release in sea urchin egg homogenates: modulation by cyclic ADP-ribose. Science 1991;253:1143-1146.

Graeff R.M., Walseth T.F., Hill H.K., Lee H.C. Fluorescent analogs of cyclic ADP-ribose: synthesis, spectral characterization, and use. Biochemistry 1996;35:379-386.

Graeff R, Munshi C, Aarhus R, Johns M, Lee H. C. A single residue at the active site of CD38 determines its NAD cyclizing and hydrolyzing activities. J. Biol. Chem. 2001; 276: 12169-12173.

Graeff R.M., Walseth T.F., Lee H.C. Radioimmunoassay for measuring endogenous levels of cyclic ADP-ribose in tissues. Methods Enzymol. 1997;280:230-241.

Graeff R.M., Walseth T.F., Fryxell K., Branton W.D., Lee H.C. Enzymatic synthesis and characterizations of cyclic GDP-ribose. A procedure for distinguishing enzymes with ADP-ribosyl cyclase activity. J. Biol. Chem. 1994; 269:30260-30267.

Guse, A.H. Cyclic ADP-ribose: a novel Ca 2+ mobilising second messenger. Cell. Signal 1999; 11:309-316.

Guse A.H., da Silva C.P., Berg I, Skapenko A.L., Weber K, Heyer P, Hohenegger M, Ashamu G.A. Schulze-Koops H, Potter B.V, Mayr G.W. Regulation of calcium signalling in T lymphocytes by the second messenger cyclic ADP-ribose. Nature 1999;398:70-73.

Hakamata Y. Nakai J., Takeshima H., Imoto K. Primary structure and distribution of a novel ryanodine receptor/calcium release channel from rabbit brain. FEBS Lett 1992; 312:229-235.

Harada N., Santos-Argumedo L., Chang R., Grimaldi J.C., Lund F.E., Branna C.I., Copeland N. G., Jenkins N.A., heath A.W., parkhouse R.M., Howeard M. Expression-cloning of a cDNA encoding a novel murine B cell activation marker. Homology to human CD38. J. Immunol. 1993;151:3111-3118.

Higashida H., Yokoyama S., Hashii M., Taketo M., Higashida M., Takayasu T., Ohshima T., Takasawa S., Okamoto H., Noda M. Muscarinic receptor-mediated dual regulation of ADP-ribosyl cyclase in NG108-15 neuronal cell membranes. J. Biol. Chem. 1997;272:31272-31277.

Howard M., Grimaldi J.C., Bazan J.F., Lund F.E., Santos-Argumedo L., Parkhouse R.M., Walseth T.F., Lee H.C. Formation and hydrolysis of cyclic ADP-ribose catalyzed by lymphocyte antigen CD38. Science 1993;262:1056-1059.

Jackson D.G., Bell J.I. Isolation of a cDNA encoding the human CD38 (T10) molecule, a cell surface of glycoprotein with an unusual discontinuous pattern of expression during lymphocyte differentiation. J. Immunol. 1990; 144:2811-2815.

Koguma T. Takasawa S., Tohgo A., Karasawa T., Furuya Y., Yonekura H., Okamoto H. Cloning and characterization of cDNA encoding rat ADP-ribosyl cyclase/cyclic ADP-ribose hydrolase (homologue to human CD38) from islets of Langerhans. Biochim. Biophys. Acta 1994;1223:160-162.

Lee H.C. A unified mechanism of enzymatic synthesis of two calcium messengers: cyclic ADP-ribose and NAADP. Biol. Chem. 1999;380:785-793.

Lee H.C. Walseth T.F., Bratt G.T., Hayes R.N., Clapper D.L. Structural determination of a cyclic metabolic of NAD+ with intracellular ntracellular Ca2+mobilizing activity. J. Biol. Chem. 1989; 264:1608-1615.

Lee H.C., Aarhus R. ADP_ribosyl cyclase: an anzyme that cyclizes NAD+ into a calcium-mobilizing metabolite. Cell Regul. 1991;2:203-209.

Lee, H. C., "Multiplicity of Ca2+ Messengers and Ca2+ Stores: A Perspective from Cyclic ADP-Ribose and NAADP", Curr. Mol. Med. (2004) vol. 4, pp. 227-237.

Lund F.E., Muller-Steffner H.M., Yu N., Stout C.D., Schuber F., Howard M.C. CD38 signaling in B lymphocytes is controlled by its ectodomain but occurs independently of enzymatically generated ADP-ribose or cyclic ADP-ribose. J. Immunol. 1999;162:2693-2702.

Muller-Steffner H.M., Augustin A., Schuber F., Mechanism of cyclization of pyridine nucleotides by bovine spleen NAD + glycohydrolase. Mechanism of cyclization of pyridine nucleotides by bovine spleen NAD+ glycohydrolase. J. Biol. Chem. 1996;271:23967-23972.

Muller H.M., Muller C.D., Schuber F. NAD+ glycohydrolase, an ecto-enzyme of calf spleen cells. Biochem. J 1983;2212(2):459-464.

Falk w., Goodwin R.H., Jr. Leonard E.J. A 48-well micro chemotaxis assembly for rapid and accurate measurement of leukocyte migration. J. Immunol. Methods 1980;33:239-247.

Munshi C., Thiel D.J., Mathews II, Aarhus R., Walseth T.F., Lee H.C. Characterization of the active site of ADP-bibosyl cyclase. J. Biol Chem 1999;274:30770-30777.

Munshi C, Aarhus R, Graeff R, Walseth T.F., Levitt D, Lee H.C. Identification of the enzymatic active site of CD38 by site-directed mutagenesis. J. Biol. Chem. 2000; 275:21566-21571.

Murphy P.M. The molecular biology of leukocyte chemoattractant receptors. Annu. Rev. Immunol. 1994;12;593-633.

Prasad G.S., McRee D.E., Stura E.A., Levitt D.G., Lee H.C., Stout C.D. Crystal structure of Aplysia ADP ribosyl cyclase, a homologue of the bifunctional ectozyme CD38. Nat. Struct. Biol. 1996;3:957-964.

Shinkai Y., Rathbun G., Lam K.P., Oltz E.M., Stewart V., Mendelsohn M., Charron J., Datta M., Young F., Stall A.M., Alt F.W., RAG-2-deficient mice lack mature lymhocytes owing to inability to initiate V(D)J rearrangement. Cell 1992;68:855-867.

Silva C.L., Cunha V.M., Mendonca-Silva D.L., Noel F. Evidence of ryanodine receptors in *Schistosoma mansoni*. Biochem. Pharmacol. 1998;56:997-1003.

Sorrentino V., Volpe P. Ryanodine receptors: how many, where and why? Trends Pharmacol. Sci. 1993; 14:98-103.

Takahashi K., Kukimoto I., Tokita K., Inageda K., Inoue S., Kontani K., Hoshino S., Nishina H., Kanaho Y., Katada T. Accumulation of cyclic ADP-ribose measured by a specific radioimmunoassay in differential human leukemic HL-60 cells with all-trans-retinoic acid. FEBS Lett. 1995;371:204-208.

Vu C.Q., Coyle D.L., Jacobson M.K. Natural occurrence of 2'-phospho-cyclic ADP ribose in mammalian tissues. Biochem. Biophys. Res. Commun. Jul. 30, 1997;236(3):723-726.

Vu C.W., Coyle D.L., Tai H.H., Jacobsen M.K. Intramolecular ADP-ribose transfer reactions and calcium signalling. Potential role of 2'-phospho-cyclic ADP-ribose in oxidative stress. Adv. Exp. Med. Biol.1997;419:381-388.

Weis J.H. 'race no more'; an alternative approach to cloning the 5' end of transcripts. Nucleic Acids res. 1994;22:3427-3428.

Yamamoto-Katayama, S. et al., "Crystallographic Studies on Human B.ST-1/CD157 with ADP-ribosyl Cyclase and NAD Gylcohydrolase Activities", J. Mol. Biol. (2002), vol. 316, pp. 711-723.

GenBank accession #AW017229, 2007.

* cited by examiner

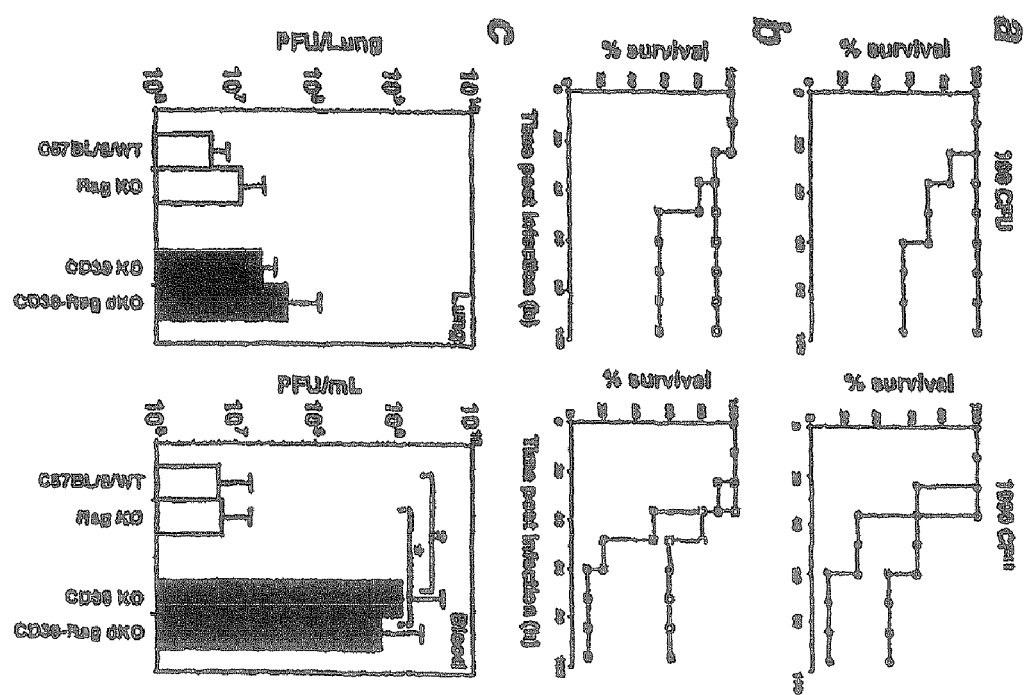
Figure 7 A-C

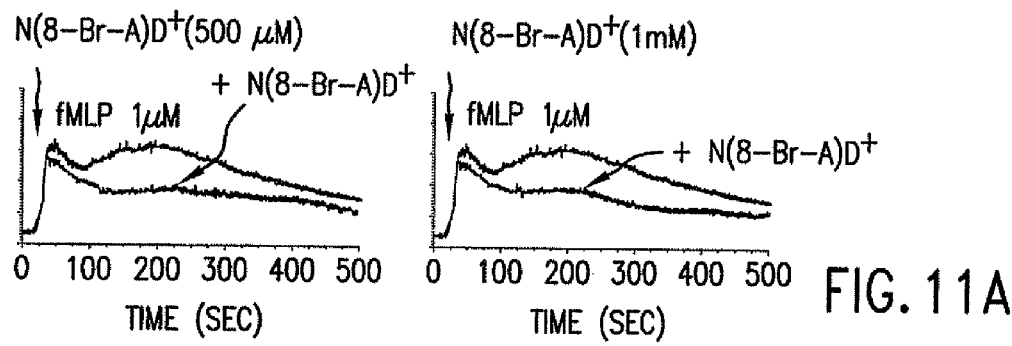
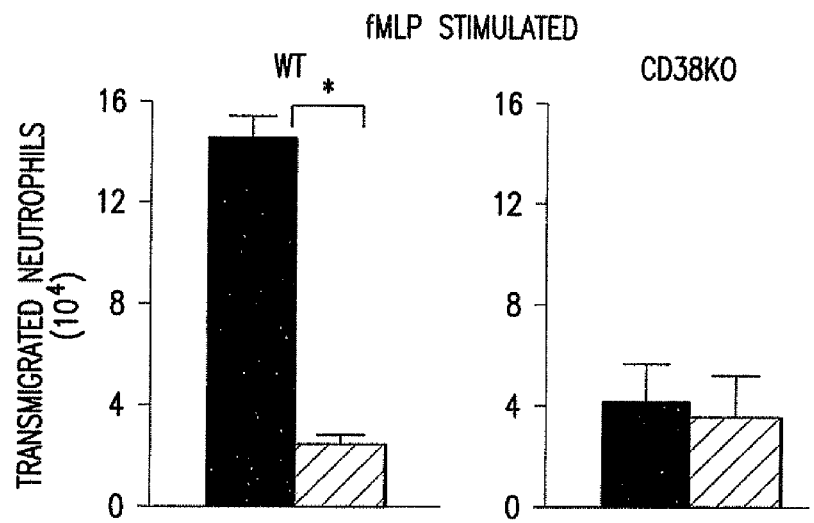
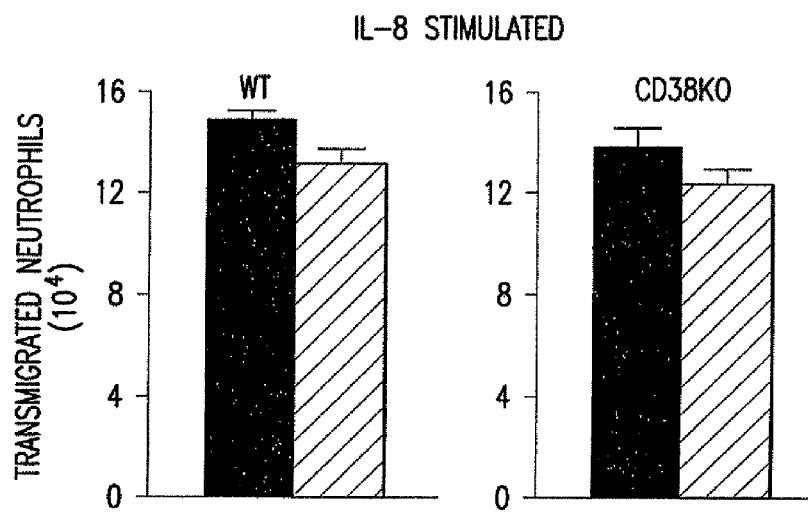

A.

```
GGCACGAGGTTATTTTTCACAATCTTTTAATTCAAATAATGATGAACGTAATATTGTTTC  60
             R  H  E  V  I  F  H  N  L  L  I  Q  I  M  M  N  V  I  L  F
TTACTTTATCAAATATTTTTGTCTTTAACTCTGCACAACATCAAATAAACTTACTTAGTG  120
 L  T  L  S  N  I  F  V  F  N  S  A  Q  H  Q  I  N  L  L  S
AAATAGTACAATCACGATGTACTCAGTGGAAGGTTGAACATGGAGCTACTAATATAAGTT  180
 E  I  V  Q  S  R  C  T  Q  W  K  V  E  H  G  A  T  N  I  S
GTAGTGAGATCTGGAATTCATTTGAAAGCATTTTACTTTCAACTCATACTAAATCAGCAT  240
 C  S  E  I  W  N  S  F  E  S  I  L  L  S  T  H  T  K  S  A
GTGTTATGAAATCAGGGTTATTCGATGATTTTGTTTATCAATTGTTTGAATTGGAACAAC  300
 C  V  M  K  S  G  L  F  D  D  F  V  Y  Q  L  F  E  L  E  Q
AACAACAACAGCGACACCACACAATTCAAACGGAACAATACTTCCATTCTCAAGTGATGA  360
 Q  Q  Q  Q  R  H  H  T  I  Q  T  E  Q  Y  F  H  S  Q  V  M
ACATCATTCGTGGAATGTGTAAACGTCTTGGAGTATGTCGTTCTCTAGAAACTACATTTC  420
 N  I  I  R  G  M  C  K  R  L  G  V  C  R  S  L  E  T  T  F
CAGGATATCTGTTTGATGAATTGAATTGGTGTAATGGCAGTTTAACAGGCAACACAAAAT  480
 P  G  Y  L  F  D  E  L  N  W  C  N  G  S  L  T  G  N  T  K
ACGGGACTGTATGTGGATGCGATTATAAAAGTAATGTTGTTCATGCGTTCTGGCAAAGTG  540
 Y  G  T  V  C  G  C  D  Y  K  S  N  V  V  H  A  F  W  Q  S
CTTCGGCTGAGTATGCCAGGAGAGCATCTGGTAACATCTTTGTGGTACTGAATGGCTCGG  600
 A  S  A  E  Y  A  R  R  A  S  G  N  I  F  V  V  L  N  G/S
TCAAAGCTCCATTTAATGAAAATAAAACTTTTGGAAAAATAGAACTACCATTGTTAAAAC  660
 V  K  A  P  F  N  E  N  K  T  F  G  K  I  E  L  P  L  K  K
ATCCTCGAGTACAACAATTAACAGTGAAATTAGTTCATAGTTTGGAAGATGTAAATAACC  720
 H  P  R  V  Q  Q  L  T  V  K  L  V  H  S  L  E  D  V  N  N
GACAAACATGTGAATCGTGGAGTCTGCAAGAACTTGCAAACAAGCTGAACTCTGTACATA  780
 R  Q  T  C  E  S  W  S  L  Q  E  L  A  N  K  L  N  S  V  H
TTCCTTTTCGTTGCATTGACGATCCTTTAGAGTTCAGACATTATCAATGCATTGAAAATC  840
 I  P  F  R  C  I  D  D  P  L  E  F  R  H  Y  Q  C  I  E  N
CTGGCAAACAACTATGTCAGTTTTCAGCTTCGACGGAGGTCAAACGTCGAGACATTACTCA  900
 P  G  K  Q  L  C  Q  F  S  A  S  T  R  S  N  V  E  T  L  L
TACTTTTTCCGCTAGTCATTTGTTTAACTTTTTATACTTCCATGAATTGAAATAACTTTT  960
 I  L  F  P  L  V  I  C  L  T  F  Y  T  S  M  N  .  N  N  F
CAGAACTAAACTTTGAACAGAGAAAGAGAACAATGATAATAAAGGAATAGGACATTAAAA  1020
 S  E  L  N  F  E  Q  R  K  R  T  M  I  I  K  E  .  D  I  K
AAAAAAAAAAAAAA  1034
 K  K  K  K  K
```

Figure 13

B.

```
S. mansoni SM38     --------------------  ---------------MMNVILF  LTLSNIFVFNSAQHQINLLS   27
A. califor. cyclase --------------------  ----------------------  ------------IVPTRELE    8
Human CD38          MANCEFSPVSGDKPCCRLSR  RAQLCLGVSILVLILVVVLA   VVVPRWRQTWSGPGTTKRFP   60
Human CD157         ----------MAAQGCAASR  LLQLLLQ------LLLLLLL   LAAGGARARWRAEGTSAHLR   44
                                                                                      :

S. mansoni SM38     EIVQSRCTQW---K--VEHG  AT-NISCSEIWNSFESILLS   THTKSACVMKSGLFDDFVYQ   81
A. califor. cyclase NVFLGRCKDYEITRYLDILP  RVRS-DCSALWKDFFKAFS-   --FKNPCDLDLGSVKDF---   61
Human CD38          ETVLARCVKY---TEI--HP  EMRHVDCQSVWDAFKGAFI-   --SKHPCNITEEDYQPL---  109
Human CD157         DIFLGRCAEY---RAL-LSP  EQRNKNCTAIWEAFKVA-L-   --DKDPCSVLPSDVDLF---   93
                        .**  .:             .*  .:*. *              * .*.:    :. :

S. mansoni SM38     LFELEQQQQQRHHTIQTEQY  FHSQVMNIIRGMCKRLGVCR   SLETTFPGYLFDELNWCNGS  141
A. califor. cyclase -FTSAQQQLPKNKVM-----  FWSGVYDEAHDVANTGRKYI   TLEDTLPGYMLNSLVWCGQR  115
Human CD38          -MKLGTQTVPCNKIL-----  LWSRIKDLAHQFTQVQRDMF   TLEDTLLGYLADDLTWCGEF  163
Human CD157         -INLSRHSIPRDKSL-----  FWENSHLLVNSFADNTRRFM   PLSDVLYGRVADFLSWCRQK  147
                      :      :    .:        :.    .   .

S. mansoni SM38     LTGNTKYGTVCG--CDYKSN  VVHAFWQSASAEVARRASGN   IFVVLNGSVK-AP-FNENKT  197
A. califor. cyclase ANPGFNEKVCPDF-KTCPVQ  ARESFWGMASSSYAHSAEGE   VTYMVDGSNPKVPAVRPDSF  174
Human CD38          NTSKINYQSCPDWRKDCSNN  PVSVFWKTVSRRFAEAACDV   VHVMLNGSRS--KIFDKNST  221
Human CD157         NDSGLDYQSCPT-SEDCENN  PVDSFWKRASIQVSKDSSGV   IHVMLNGSEP-TGAVPIKGF  205
                                                **  .*   ::.  :                :  :::**

S. mansoni SM38     FGKIELPLLKHPRVQQLTVK  LVHSLEDVNNRQTCESWSLQ   ELANKLNSVHIPFRCIDDPL  257
A. califor. cyclase FGKYELPNLTN-KVTRVKVI  VLHRLGE-KIIEKCGAGSLL   DLEKLVKAKHFAFDCVENPR  232
Human CD38          FGSVEVHNLQPEKVQTLEAW  VIHGGRE-DSRDLCQDPTIK   ELESIISKRNIQFSCKNIYR  280
Human CD157         FADYEIPNLQKEKITRIEIW  VMHEIGG-PNVESCGEGSMK   VLEKRLKDMGFQYSCINDYR  264
                    *.. .*: *   ::    :       ::.*        .*   ::     *  .:    .  : * :

S. mansoni SM38     EFRHYQCIENPGKQLCQFSA  S---TRSNVETLL------I   LFPLVICLTFYTSMN       303
A. califor.cyclase  AVLFLLCSDNPNARECRLAK  RFYRIA--------------   ----------------      258
Human CD38          PDKFLQCVKNPEDSSCTSEI  --------------------   ----------------      300
Human CD157         PVKLLQCVDHSTHPDCALKS  AAAATQRKAPSLVTEQRAGL   IIPLFLVLASRTQL-       318
                         * .:.    *                                                    
```

```
                        %I    %S
S. mansoni SM38         ----  ----
A. califor. cyclase     24    39
Human CD38              21    37
Human CD157             21    38
```

Figure 14 A-B

A.

| | | | | |
|---|---|---|---|---|
| Consensus | M.......... .L........S ....I...... L.......RC. ........... | 50 |
| Aplysia cd38p | MSPVAIVACV CLAVTLTRIS PSEAIFPTPE LQNVFLGRCK DVEITRVLTI | 50 |
| SM38p | M--MNVILFL TLSNIFVFNS AQHQI---NL LSEIVQSRCT QWKVEH---- | 41 |

| | | | | |
|---|---|---|---|---|
| Consensus | ........C. .W..F..... .....K..C.. ...G....DF.. ........... | 100 |
| Aplysia cd38p | LPRVKSDCRA LWTNRFKAFS F---RAPCNL DLGSYKDFFQ RAQQTLPKNK | 97 |
| SM38p | -GATNISCSE IWNSRESILL STHTKSACVM KSGLFDDFVY QLFELEQQQQ | 90 |

| | | | | |
|---|---|---|---|---|
| Consensus | .......... .......... .......... ..LE.T.PGY ....L..WC.. | 150 |
| Aplysia cd38p | VMFWSGVYDE --AHDF---- ADDGRKYI-- -TLECTLPGY MLNSLVMCGQ | 138 |
| SM38p | QRHHTIQTEQ YFHSQVMNII RGNCKRLGVC RSLETFFPGM LFDELNMCNG | 140 |

| | | | | |
|---|---|---|---|---|
| Consensus | .......... VC....D.... ......FW..A S..YA..A.G .......GS. | 200 |
| Aplysia cd38p | RDKPGFNQK- VCPDFKDCPV QARESFNGTA GSSYAHSAEG DVTYMVDGSN | 187 |
| SM38p | SLTGNTKYGT VG---GCDYKS NVVHAFWQSA GAEYARRASG NIFVVLNGS- | 186 |

| | | | | |
|---|---|---|---|---|
| Consensus | .......... .FGK.ELP.L ....V...... H.L....... ....C...SL | 250 |
| Aplysia cd38p | PKVPAYRPDS FFGKYELPNL TNK-MTKVKV IVLHQLGQKI I-ERCGAGSL | 235 |
| SM38p | -VKAPFNENK TFGKIELPLL KHPRMQQLTV KLVHSLEDVN NRQTQESWSL | 236 |

| | | | | |
|---|---|---|---|---|
| Consensus | ...L...... .....F.C...P .......C... NP.....CQ.. ........... | 300 |
| Aplysia cd38p | LDLENVVKAK KFGFDCVENP KSVLFLLDAD RMARERQLA KRYYRIA--- | 282 |
| SM38p | QELANKLNSV HIPFRQIDDP LEFRHYQCIE NFGKQLCQFS ASTRSNVETL | 286 |

| | | | | |
|---|---|---|---|---|
| Consensus | .......... ....... | 317 |
| Aplysia cd38p | ---------- ------ | 282 |
| SM38p | LILFPLVICL TFYTSMN | 303 |

B.

| | | | | |
|---|---|---|---|---|
| Consensus | M......... .......... .......... ...IL...L. .........Q. | 50 |
| Human CD38 | MANCEFSPVS GDKPCCRLSR RAQLCLGVSI LVLILVVVLA VVVPRWRQQW | 50 |
| SM38p | M--------- ---------- ---------- MNVILFLTLS NIFVFNSAQ- | 20 |

| | | | | |
|---|---|---|---|---|
| Consensus | .......... E.V..RC... .......... .C...W..F. .....S.H.K. | 100 |
| Human CD38 | SGPGTTKRFP ETVLARCVKY TEIHPEMRHV DCQSVWDAFK GAFIS---KH | 97 |
| SM38p | ---HQINLLS EIVQSRCTQW -KVEHGATNI SCSEIWNSRE SILLSTHTKS | 66 |

| | | | | |
|---|---|---|---|---|
| Consensus | .C......... ...YQ..... .......... ........S.. ........... | 150 |
| Human CD38 | PCNITEED-- ---YQPLMKL GTQTVPCNKI L----LWSRI KDLAHQFTQV | 138 |
| SM38p | ACVMKSGLFD DFVYQLFELE QQQQQRHHTI QTEQYFHSQV MNIIRGMCKR | 116 |

| | | | | |
|---|---|---|---|---|
| Consensus | ......LE.T ..GYL.D.L. WC....T... ...Y..C..... ..C.....N.V | 200 |
| Human CD38 | QRDMFTLEDT LLGYLADDLT WCGEFNTSKI NYQS-CPDWR KDC---SNNPV | 185 |
| SM38p | LGVCRSLETI FPGMLFDELN MQNGSLTGNT KYGTVDG--- --DYKSNVV | 161 |

| | | | | |
|---|---|---|---|---|
| Consensus | ..FW...S.. .A..A...... V.LNGS.... F..N.TFG.. E...L......V | 250 |
| Human CD38 | SVFWKTVSRR FAEACDVVH VMLNGSRSKI FDKNSTFGSV EVHNLQPEKV | 235 |
| SM38p | HAFWQSASAE YARRASGNIF VVLNGSVKAP FNENKTFGKI ELPLLKHPRV | 211 |

| | | | | |
|---|---|---|---|---|
| Consensus | Q.L.....H. ......R..C ......EL... ........I.F. C......... | 300 |
| Human CD38 | QTLEAWVIHG GRE-DSRDLC QDPTIKELES IISKRNIQFS CKNIYRPDKF | 284 |
| SM38p | QQLTVKLVHS LEDVNNRQTQ ESWSLQELAN KLNSVHIPFR QIDDPLEFRH | 261 |

| | | | | |
|---|---|---|---|---|
| Consensus | .QC..NP... .C......... .......... .........TS .. | 342 |
| Human CD38 | LQDVKNFEDS SQ-------- ---------- --------TS EI | 300 |
| SM38p | YQCIENGGKQ LCQFSASTRS NVETLLILFP LVICLTFYTS MN | 303 |

```
S. mansoni Sm38    MMNVILFHILSNIFVENSAQ HQINLLSEIVQSRCTQWKVE HGATNISCSEIWNSFESILL     60
S. japonicum Sm38  FNIMLSFILLNILLTPAVQ  CQRNFFADIVISRCILWTVT HNITNVACVDVWSSFEKTLL     59
                   **:.* : * **::  :.*  * *:::.** ***   *.*   *. **:.* ::*.***. **

S. mansoni Sm38    STHTKSACVMKSGLFDDFVY QLFELEQQQQRHHTIQTEQ  YFHSQVMNIIRGMCKRLGVC    120
S. japonicum Sm38  SISNQSECIVQSQLFDNFVH KTFEMQQQPN------QSGQ YFHSQVTHVIRGMCKRLGVC    113
                   * .:* *:::* ***:**:  : **:**  :          *: * ****** :.**********

S. mansoni Sm38    RSLETTFPGYLFDELNWCNG SLTGNTKYGTVCGCDYKSNV VHAFWQSASAEYARRASGNI    180
S. japonicum Sm38  RSLETTFPGYLFDELDWCNN SLIDSSHYGTVCKCDYYNGV INAFWKSASAEYARRASGTI    173
                   ***************.***. ** ..:*****  ** .* :***:**********. *

S. mansoni Sm38    FVVLNGSVKAPFNENKTFGK ICLPLLKHPRVQQLTVKLVH SLEDVNNRQTCESWSLQELA    240
S. japonicum Sm38  FVVLNGSAKLPFNENRTFGS VCLPQLKYPKVKQLIVKLIH NLEDSIPRHTCESINLLRLS    233
                   *******.* *****:***. :*** **.*.*::**.***:* .***   *.*  *  *.:

S. mansoni Sm38    NKLNSVHIPFRCIDDPLEFR HYQCIENPGKQLCQFSASDRSNVETLLLTFRYICNELT    297
S. japonicum Sm38  SKVKSSNISFSCINDPLEFK HYQCIQNPFNKQCRFSSANSNFFKICLLLSSLPICSTPI    293
                   .*::* :*.* **:*****: *****:** .:** :**:*:. **  .:***:   .*

%I  %S
S. mansoni Sm38    FVISMI   303  ---
S. japonicum Sm38  SPCRIT   299  56  74
                   : :*
```

Fig. 15

```
ATGATGAAYG  TNATHYTNTT  YYTNACNYTN  WSNAAYATHT  TYGTNTTYAA   50
YWSNGCNCAR  CAYCARATHA  AYYTNYTNWS  NGARATHGTN  CARWSNMGNT  100
GYACNCARTG  GAARGTNGAR  CAYGGNGCNA  CNAAYATHWS  NTGYWSNGAR  150
ATHTGGAAYW  SNTTYGARWS  NATHYTNYTN  WSNACNCAYA  CNAARWSNGC  200
NTGYGTNATG  AARWSNGGNY  TNTTYGAYGA  YTTYGTNTAY  CARYTNTTYG  250
ARYTNGARCA  RCARCARCAR  CARMGNCAYC  AYACNATHCA  RACNGARCAR  300
TAYTTYCAYW  SNCARGTNAT  GAAYATHATH  MGNGGNATGT  GYAARMGNYT  350
NGGNGTNTGY  MGNWSNYTNG  ARACNACNTT  YCCNGGNTAY  YTNTTYGAYG  400
ARYTNAAYTG  GTGYAAYGGN  WSNYTNACNG  GNAAYACNAA  RTAYGGNACN  450
GTNTGYGGNT  GYGAYTAYAA  RWSNAAYGTN  GTNCAYGCNT  TYTGGCARWS  500
NGCNWSNGCN  GARTAYGCNM  GNMGNGCNWS  NGGNAAYATH  TTYGTNGTNY  550
TNAAYGGNWS  NGTNAARGCN  CCNTTYAAYG  ARAAYAARAC  NTTYGGNAAR  600
ATHGARYTNC  CNYTNYTNAA  RCAYCCNMGN  GTNCARCARY  TNACNGTNAA  650
RYTNGTNCAY  WSNYTNGARG  AYGTNAAYAA  YMGNCARACN  TGYGARWSNT  700
GGWSNYTNCA  RGARYTNGCN  AAYAARYTNA  AYWSNGTNCA  YATHCCNTTY  750
MGNTGYATHG  AYGAYCCNYT  NGARTTYMGN  CAYTAYCART  GYATHGARAA  800
YCCNGGNAAR  CARYTNTGYC  ARTTYWSNGC  NWSNACNMGN  WSNAAYGTNG  850
ARACNYTNYT  NATHYTNTTY  CCNYTNGTNA  THTGYYTNAC  NTTYTAYACN  900
WSNATGAAY                                                   909
```

Figure 17

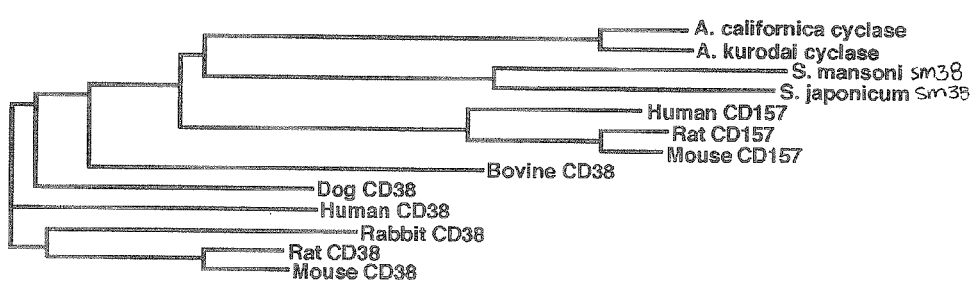
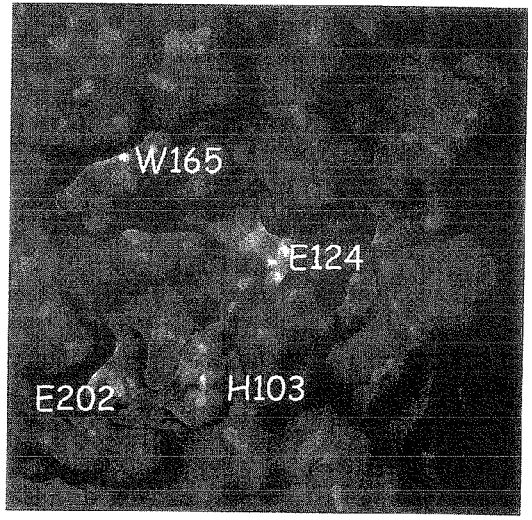
Figure 18

CD38 MODULATED CHEMOTAXIS

1. INTRODUCTION

This application is a divisional of U.S. application Ser. No. 11/058,924, filed Feb. 15, 2005, which issued as U.S. Pat. 7,695,933 which is a continuation-in-part of U.S. application Ser. No. 09/982,616 filed Oct. 17, 2001, which issued as U.S. Pat. 6,955,884, which claims priority to U.S. Provisional Application Ser. No. 60/241,065 filed Oct. 17, 2000.

The present invention relates to methods for modulating the migratory activity of cells expressing CD38 for the treatment of disorders including, but not limited to, inflammation, ischemia, asthma, autoimmune disease, diabetes, arthritis, allergies, infection with pathogenic organisms, such as parasites, and transplant rejection. Such cells include, for example, neutrophils, lymphocytes, eosinophils, macrophages and dentritic cells. The invention further relates to drug screening assays designed to identify compounds that modulate the ADP-ribosyl cyclase activity, NAD glycohydrolase activity, and transglycosidation activity of CD38 and the use of such compounds in the treatment of disorders involving CD38 modulated cell migration. The present invention relates to the isolation and characterization of a CD38 homologue from the parasitic flatworm, *Schistosoma mansoni*. The identification of such a homologue, referred to herein as SM38 or SARC, provides compositions and assays designed to screen for related enzymes in pathogenic organisms as well as compositions and assays to screen for compounds that modulate the activity and/or expression of SM38. Such compounds can be used to treat pathogenic disorders resulting from infection with such parasites. The invention is based on the discoveries that CD38 ADP-ribosyl cyclase activity is required for chemotaxis and that *S. mansoni* expresses a CD38 homologue that can regulate calcium responses in the parasite.

2. BACKGROUND OF INVENTION

Hematopoietically-derived cells, including cells such as neutrophils, monocytes, dendritic cells, eosinophils and lymphocytes, are important cellular mediators of the inflammatory response and respond to soluble inflammatory mediators by migration to the site of tissue injury or infection where the newly arrived cells perform their effector functions.

Neutrophils which represent 40-50% of the circulating leukocyte population are particularly important to both immunity and inflammation. Neutrophils are normally quiescent cells but upon stimulation can mediate a variety of different inflammatory activities. A large number of different agents are capable of activating neutrophils and this activation is normally mediated by binding of the activating agent to specific receptors expressed on the surface of neutrophils. Once activated, the neutrophils are capable of binding to endothelial cells and migrating to the site of tissue damage, a pathogen or a foreign material. Similarly, eosinophils are also potent inflammatory effector cells, although these cells are most often associated with allergic diseases such as asthma. Like neutrophils, eosinophils have a potent armory of proinflammatory molecules that can initiate and maintain inflammatory responses.

Once at the inflammatory site, recruited cells such as eosinophils and neutrophils induce further inflammation by releasing inflammatory products and recruiting other hematopoietically-derived cells to the site. In some cases, the inflammatory response mediated by the specifically recruited hematopoietically-derived cells protects the host from morbidity or mortality by eliminating the infectious agent. In other cases (i.e., autoimmunity, ischemia/reperfusion, transplantation, allergy), the inflammatory response further damages the tissue resulting in pathology. Thus, agents which alter inflammation or recruitment of cells may be useful in controlling pathology.

Although CD38 expression was at first believed to be restricted to cells of the B cell lineage, subsequent experiments by a number of groups have demonstrated that CD38 is widely expressed on both hematopoietic and non-hematopoietically-derived cells. Homologues of CD38 have also been found to be expressed in mammalian stromal cells (Bst-1) and in cells isolated from the invertebrate *Aplysia californica* (ADP-ribosyl cyclase enzyme) (Prasad G S, 1996, Nature Structural Bio 13:957-964)

More recently, CD38 was shown to be a multifunctional ecto-enzyme with NAD+glycohydrolase activity, transglycosidation activity and ADP-ribosyl cyclase activity, enabling it to produce nicotinamide, ADPribose (ADPR), cyclic-ADPR (cADPR) and nicotinic acid adenine dinucleotide phosphate (NAADP) from its substrates NAD+ and NADP+ (Howard et al., 1993 Science 252:1056-1059; Lee et al., 1999 Biol. Chem. 380; 785-793). Cyclic ADPR mediates intracellular calcium release through ryanodine receptor gated stores (Galione et al., 1991 Science 253:1143-1146; Lee, 1993 J. Biol. Chem. 268:293-299; Meszaros et al., 1993 Nature 354:76-78), while ADPR induces $Ca^{2+}$ influx in mammalian cells by activating the plasma membrane ion channel, TRPM2 (Perraud et al. 2001 Nature: 411:595-599; Sano et al. 2001 Science 293:1327-1330; Hara et al. 2002 Mol. Cell. 9:163-173). In addition, $NADP^+$, which is also utilized as a substrate by cyclases, can be transformed into nicotinic acid adenine dinucleotide ($NAADP^+$) in a base-exchange reaction in the presence of nicotinic acid (Aarhus et al. 1995. J. Biol. Chem. 270:30327-30333). $NAADP^+$ is a very powerful $Ca^{2+}$-mobilizing metabolite that mediates $Ca^{2+}$ release from intracellular stores that are gated independently of both $IP_3R$ and RyRs (Lee et al., 1995 J. Biol. Chem. 270:2152-2157). Thus, cyclases have the ability to produce at least three different second messengers that mobilize multiple independent sources of calcium, suggesting that these metabolites may be global regulators of calcium responses (Lee et al., 1999 Biol. Chem. 380; 785-793). All three of these second messengers are also produced by SM38.

Both cADPR and NAADP are known to induce calcium release from calcium stores that are distinct from those controlled by IP3 receptors (Clapper, D L et al., 1987, J. Biological Chem. 262:9561-9568). Instead, cADPR is believed to regulate calcium release from ryanodine receptor regulated stores, as agonists of ryanodine receptors sensitize cADPR mediated calcium release and antagonists of ryanodine receptors block cADPR dependent calcium release (Galione A et al., 1991, Science 253:143-146). Thus, it has been proposed that cADPR is likely to regulate calcium responses in tissues such as muscle and pancreas where ryanodine receptors are expressed. Interestingly, it was recently shown that the muscle fibers of the parasitic flatworm, *S. mansoni*, express ryanodine receptors and that agonists of ryanodine receptors such as caffeine can induce intracellular calcium release and muscle contraction in the parasite (Day et al., 2000 Parasitol 120:417-422; Silva et al., 1998, Biochem. Pharmaco. 156: 997-1003). In mammalian smooth muscle cells, the calcium release in response to acetylcholine can be blocked not only with ryanodine receptor antagonists, but also with specific antagonists of cADPR such as 8-NH2-cADPR or 8-Br-cADPR (Guse, A H, 1999, Cell. Signal. 11:309-316).

These findings, as well as others, indicate that ryanodine receptor agonists/antagonists including cADPR can regulate calcium responses in cells isolated from species as diverse as helminths to mammals, however, it is unclear whether ADP-ribosyl cyclase enzymes such as CD38 or SM38 are required for the production of cADPR in vivo. Additionally, there has been no direct evidence to link CD38 enzyme activity with downstream responses such as calcium release, proliferation, apoptosis, migration or other effector functions. Thus, despite the high level expression of CD38 on many cell types, no clear defining role for CD38 enzyme activity in immune responses has been established.

3. SUMMARY OF THE INVENTION

The present invention relates to methods for modulating the migratory activity of cells expressing CD38 involving the administration of agonists or antagonists of CD38 enzyme activity, and the cADPR mediated signal transduction pathway, including small molecules, large molecules, and antibodies. The invention also provides for compounds and nucleotide sequences that can be used to modulate CD38 gene expression.

The present invention further relates to the isolation and characterization of a CD38 homologue from the parasitic flatworm *Shistosoma mansoni*, herein referred to as SM38. The identification of such a homologue provides compositions and assays designed to screen for related enzymes in pathogenic micro-organisms (such as helminths) as well as compositions and assays to screen for compounds that modulate the activity of SM38. Such compounds can be used to treat pathogenic disorders resulting from infection with such pathogenic micro-organisms.

The invention relates to assays designed to screen for compounds that modulate the enzymatic activity of CD38 and/or SM38 (CD38/SM38), i.e., compounds that act as agonists and antagonists of CD38 enzyme activity. When screening for such compounds for treatment of helminth infection, it is preferred that the compound selectively inhibit SM38 and not CD38. In addition, the screens of the invention may be used to identify substrates of CD38/SM38 that are converted into antagonists or agonists of signal transduction pathways involving cADPR. The screens of the invention also maybe used to directly identify agonists and antagonists of signal transduction pathways involving cADPR.

The invention also relates to assays designed to screen for compounds that modulate CD38/SM38 gene expression. For example, cell-based assays can be used to screen for compounds that modulate CD38/SM38 transcription such as compounds that modulate expression, production or activity of transcription factors involved in CD38/SM38 gene expression; antisense and ribozyme polynucleotides that modulate translation of CD38/SM38 mRNAs and polynucleotides that form triple helical structures with the CD38/SM38 regulatory regions and inhibit transcription of the CD38/SM38 gene.

Identified compounds may be used in the treatment of disorders where the migratory activity of CD38-expressing cells, such as hematopoietically-derived cells, contributes to the development of such disorders. Such disorders include, but are not limited to inflammation, ischemia, asthma, autoimmune disease, diabetes, arthritis, allergies or transplant rejection where inhibition of migratory activity using, for example, CD38 antagonists would be desired. In contrast, in subjects infected with pathogenic microorganisms or immunosuppressed subjects it may be, desirable to induce the migratory activity of hematopoietically-derived cells using, for example, agonists of CD38. Additionally, identified compounds may be used to treat pathogenic disorders resulting from infection with pathogenic micro-organisms expressing SM38 or structurally related homologous proteins.

4. BRIEF DESCRIPTION OF THE FIGURES

FIG. 1. Normal Cellular Response to Chemoattractant Signaling. (1) Chemoattractant binds to receptor and initiates signaling. (2) CD38 hydrolyzes NAD and produces cADPR, which facilitates Ca2+release from internal stores. (3) Ca2+is released from cADPR-controlled internal stores which activates external Ca2+channel. (4) Extracellular Ca2+flows into the cell and allows migration.

Figure 2:
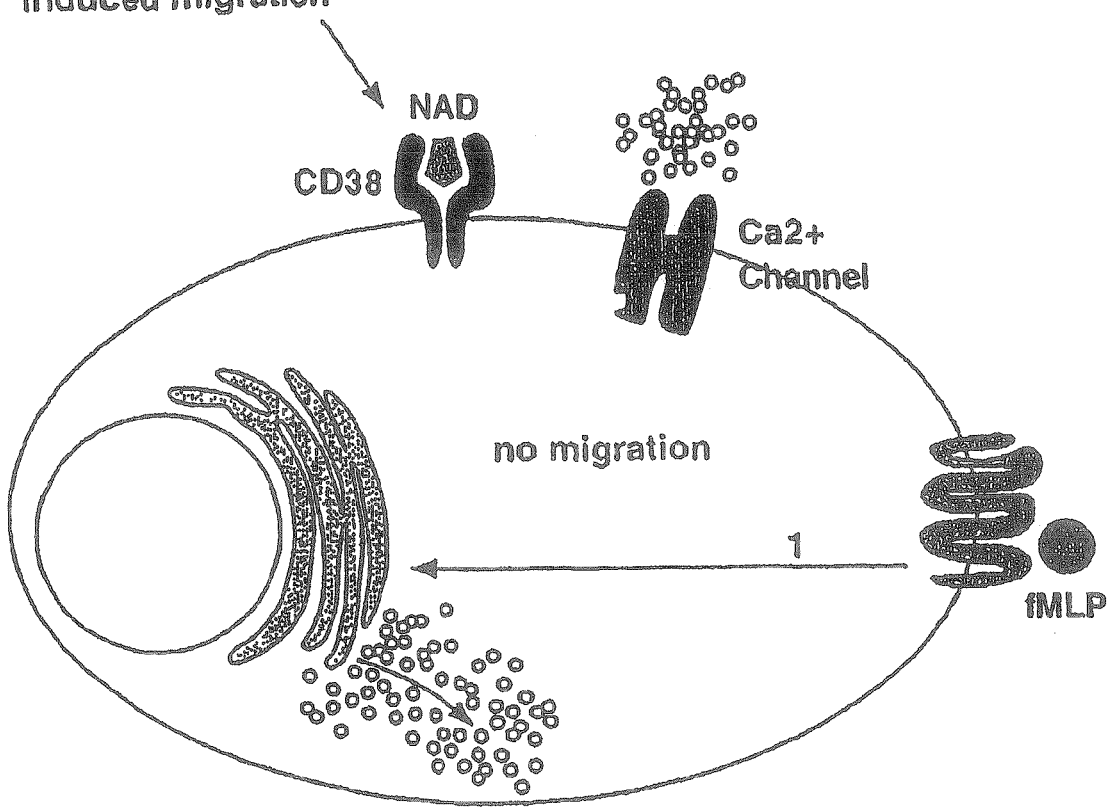

FIG. 2. Inhibitors of cADPR Production by CD38 Prevent Capacitative Ca2+ Entry and Chemoattractant Induced Migration (Screens will identify such compounds). (1) Chemoattractant binds to receptor and initiates signaling. (2) Inhibitor of CD38 prevents either hydrolysis of NAD (enzyme is inactive and no products are made) or specifically inhibits production of cADPR (blocks ADP-ribosyl cyclase activity, but enzyme may not be inactive). (3) Lack of cADPR results in no cADPR-mediated Ca2+release from internal stores. (4) No capacitative Ca2+influx and no migration.

Figure 3:
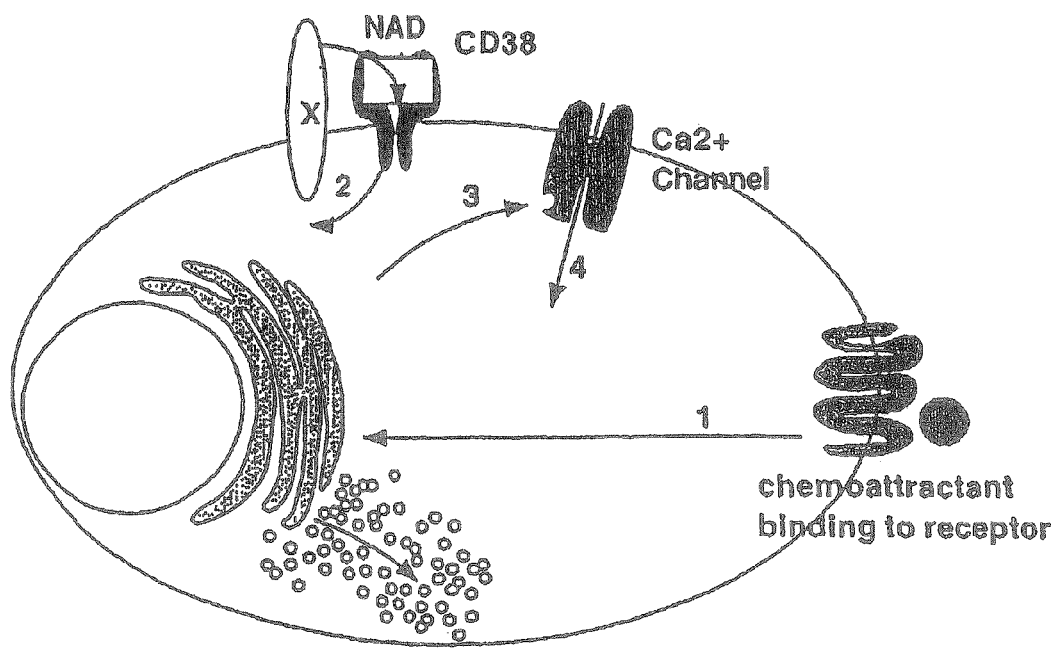

FIG. 3. Proteins that Regulate CD38 Enzyme Activity (Screens will identify compounds that activate or inactivate these proteins). (1) Chemoattractant binds to receptor and initiates signaling. (2) Protein X. modifies CD38 and inactivates CD38 enzyme activities. (3) Lack of cADPR results in no cADPR-mediated Ca2+release from internal stores. (4) No capacitative Ca2+influx and no migration.

Figure 4:
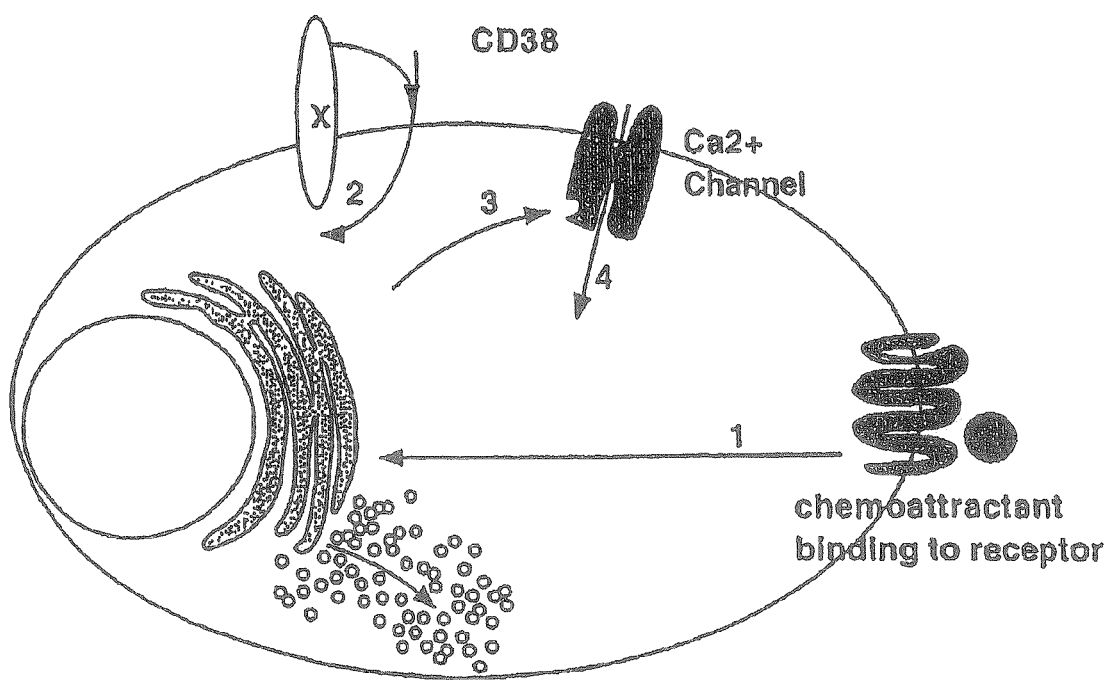

FIG. 4. Proteins that Regulate CD38 Expression (Screens will identify compounds that activate or inactivate these proteins). (1) Chemoattractant binds to receptor and initiates signaling. (2) Protein X represses CD38 gene transcription. (3) Lack of CD38 results in absence of cADPR which results in no cADPR-mediated Ca2+release from internal stores. (4) No capacitative Ca2+influx and no migration.

Figure 5:
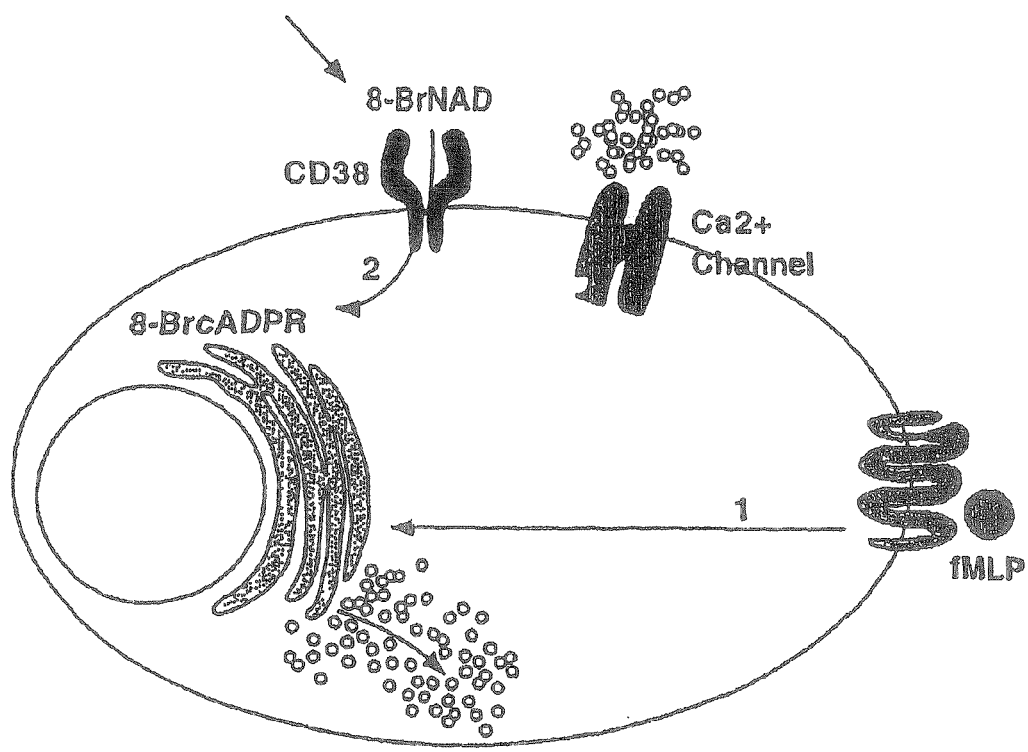

FIG. 5. Alternate Substrates for CD38 may generate inhibitors of cADPR and prevent capacitative Ca2+release (Screens will identify such compounds). (1) Chemoattractant binds to receptor and initiates signaling. (2) CD38 hydrolyzes modified substrate (8-BrNAD, for example) and produces modified product (8-Br-cADPR, for example) (3) Modified product competitively or non competitively inhibits cADPR induced Ca2+release from internal stores. (4) No capacitative Ca2+influx and no migration.

Figure 6:
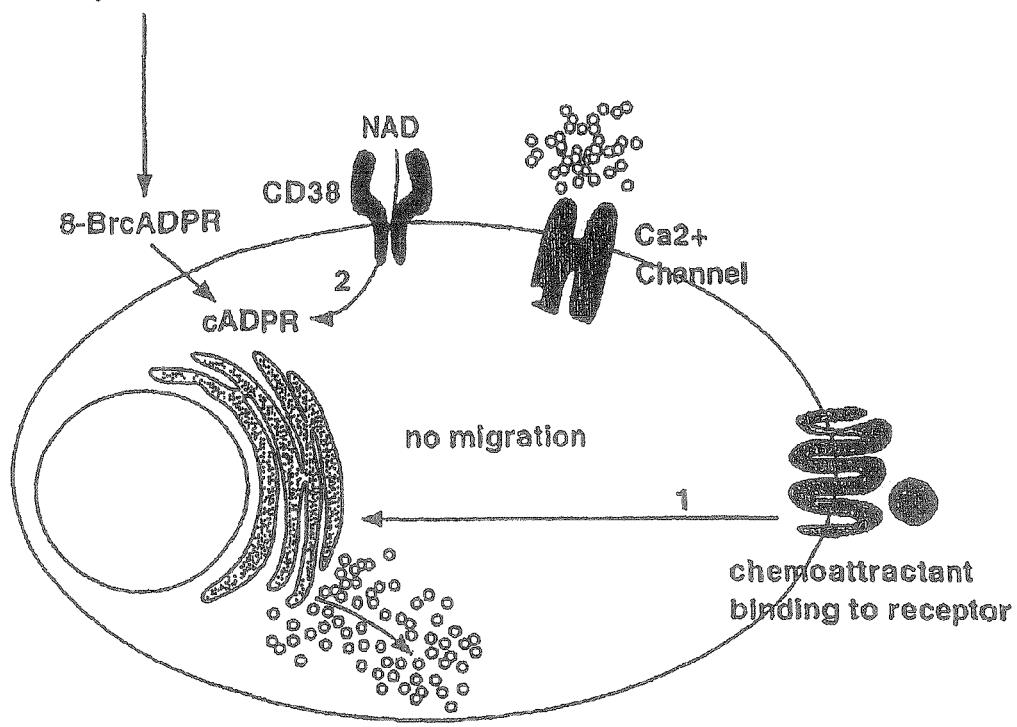

FIG. 6. Inhibitors of cADPR binding block capacitative Ca2+influx. (1) Chemoattractant binds to receptor and initiates signaling (Screens will identify such compounds). (2) CD38 hydrolyzes NAD and produces cADPR. (3) Inhibitor of cADPR (8-Br cADPR) competitively or non-competitively blocks cADPR induced Ca2+release from internal stores. (4) No capacitative Ca2+influx and no migration.

FIG. 7. CD38KO mice are more susceptible to *S. pneumoniae* infection. (a) C57BL/6 WT (open circles) and CD38KO (filled circles) mice were infected intra-tracheally with two doses of *S. pneumoniae*. The survival of infected animals was monitored over the next 4 days. (b) WT mice that had been irradiated and reconstituted with WT bone marrow (open squares) or CD38KO bone marrow (filled squares) were infected with two doses of *S. pneumoniae* and monitored for four days. The data are representative of at least 5 independent experiments. n=10 mice/group. (c) WT or Rag-2 KO (open bars) and CD38KO or CD38-Rag-2 double KO (filled bars) mice were infected intra-tracheally with *S. pneumoniae* and bacterial titers in lung and peripheral blood were determined at 12 hours post-infection. The data are representative of 3 independent experiments. N=10 mice/group. *P<0.001; Student's t test.

FIG. 8. CD38KO neutrophils are not recruited to the infection site and are unable to chemotax toward bacterially-derived chemoattractants. WT and CD38KO mice were infected intra-tracheally with S. pneumoniae, and the cellular infiltrate in the airways was collected and counted (panel a, WT=open bars and CD38KO=closed bars) at multiple timepoints post-infection. (b) The identity and frequency of the infiltrating cells in the lungs of infected WT and CD38KO mice was determined by microscopic examination (400× magnification) and counting of Diff-Quick stained cytocentrifuge preparations. (c) Differential cell counts in the lung lavage of WT (open bars) and CD38KO (closed bars) mice are presented as the mean number of cells×$10^6$±(SE). Similar results were obtained in 5 independent experiments. n=5 mice/group/timepoint. *P<0.01 **P=0.01; Student's t Test. (d) Purified bone marrow neutrophils from WT (open bars) and CD38KO mice (filled bars) were tested for their ability to migrate in response to medium, fMLP or IL-8 in a conventional transwell checkerboard chemokinesis/chemotaxis assay. The number of cells migrating to the bottom chamber of the transwell in the absence of any stimulation was not significantly different between CD38KO and WT neutrophils and ranged from 1500-2300 cells (not shown). The number of neutrophils migrating in response to equivalent concentrations of stimuli in both chambers (chemokinesis) and the number of neutrophils migrating in response to a chemotactic gradient (chemotaxis) is shown. The values shown are the mean±S.E. of four different experiments. *P<0.001; Student's t Test.

FIG. 9. CD38 expressing neutrophils produce cADPR and release intracellular calcium in response to cADPR and ryanodine. (a) Bone marrow, peripheral blood and peritoneal cavity cells were isolated from WT and CD38KO mice or WT and CD38KO mice that received an intraperitoneal injection of thioglycollate 12 hrs previously. CD38 expression on the Mac-1$^{hi}$GR 1$^{hi}$ neutrophils was analyzed by flow cytometry. Expression of CD38 on WT neutrophils (solid line histogram) and CD38KO neutrophils (dotted line histogram) is shown. (b) CD15+human peripheral blood neutrophils were assessed for CD38 expression by staining with anti-CD38 mAb (filled histogram) or an isotype control Ab (dotted line). (c) Cyclase activity was measured in WT and CD38KO bone marrow neutrophils. WT or CD38KO neutrophils were incubated alone (WT=circles and CD38KO=squares) or in the presence of NOD (WT=triangles and CD38KO=diamonds) for 10 minutes. The accumulation of the product, cGDPR, was measured fluorometrically. (d) RyR3 mRNA expression levels were determined by RT-PCR. cDNA was isolated from purified WT bone marrow neutrophils (PMN) or brain tissue. The amount of input cDNA is indicated. (e-g) Intracellular free calcium levels were measured by FACS in Fluo-3/Fura Red loaded bone marrow neutrophils. (e) Neutrophils were permeabilized with digitonin and then stimulated with ryanodine in the presence (orange line) or absence (blue line) of ruthenium red. (f) Neutrophils were permeabilized in digitonin and then stimulated with cADPR (blue line), heat inactivated cADPR (green line) or 8-Br-cADPR+cADPR (red line), (g) Neutrophils were stimulated with thapsigargin (blue line) or thapsigargin+8-Br-cADPR (red line). All data in panels' e-g are representative of at least three independent experiments.

FIG. 10. CD38 catalyzed cADPR regulates intracellular calcium release, extracellular calcium influx and chemotaxis in neutrophils. (a-c) Intracellular free calcium levels were measured by FACS in Fluo-3/Fura Red loaded bone marrow neutrophils. (a) CD38KO (red line) and WT (blue line) neutrophils were stimulated with fMLP or IL-8 in calcium-free buffer. (b) CD38KO (red line) and WT (blue line) neutrophils were stimulated with fMLP or IL-8 in calcium-containing buffer. (c) CD38KO (red line) and WT (blue line) neutrophils were preincubated in calcium-containing medium±8-Br-cADPR and then stimulated with fMLP or IL-8. All data in panels a-c are representative of at least five independent experiments. (d) WT neutrophils were pre-incubated with medium, EGTA or 8-Br-cADPR and then placed in the top chamber of a transwell that contained fMLP or IL-8 in the bottom chamber. The cells that migrated to the bottom chamber in response to the chemotactic gradient were collected and enumerated by flow cytometry. Values shown are mean±S.E. from three separate experiments with three wells/experimental condition. **P=0.008; Mann Whitney Rank Sum Test.

FIG. 11. An NAD+analogue regulates calcium influx and chemotaxis in fMLP-activated neutrophils. (a) Dye-loaded purified bone marrow neutrophils from WT mice were pre-incubated in medium (blue line) or increasing concentrations of N(8-Br-A)D+(red line) and then stimulated with fMLP. Changes in intracellular calcium levels were measured by flow cytometry. The data are representative of three independent experiments. (b-c) WT (left panel) and CD38KO (right panel) neutrophils were preincubated with medium (filled bars) or N(8-Br-A)D+(open bars) and then placed in the top chamber of a transwell which contained fMLP (panel b) or IL-8 (panel c) in the bottom chamber. The cells that migrated to the bottom chamber in response to the chemotactic gradient were collected and enumerated by flow cytometry. Values shown are mean t S.E. from three separate experiments with three wells/experimental condition. *P<0.001 Student's t Test.

Figure 12:
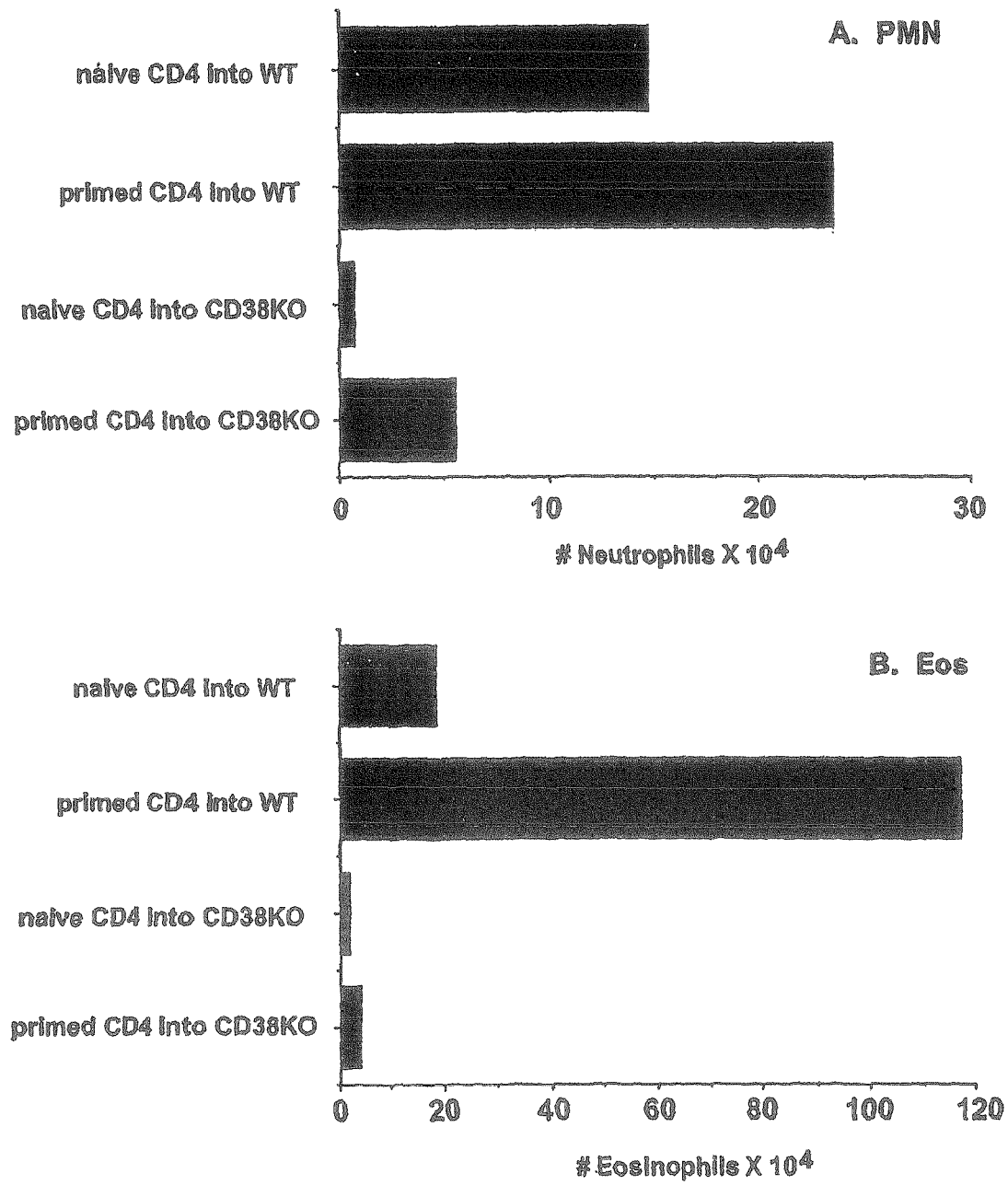

FIG. 12 A-B. The recruitment of neutrophils and eosinophils to the lungs in a model of allergic asthma is impaired in CD38 KO mice. Naive CD4 T cells from WT C57BL/6 mice or OVA-primed CD4 T cells from WT C57BL/6 mice were transferred to either WT C57BL/6 mice or to CD38KO-057BL/6 mice as indicated. Recipient mice were subsequently challenged on 7 consecutive days by intratracheal instillation of 10 μg OVA in PBS. Neutrophils (A) and eosinophils (B) in the lung lavage on the eighth day after initial challenge were enumerated by microscopic examination (400×) of Diff—Quick stained cytocentrifuge preparations FIG. 13. Identification and isolation of SARC cDNA. FIG. 13A. A full length cDNA encoding was cloned from a S. mansoni cDNA library using a cloned S. mansoni EST (Accession # AW017229) that was identified in a blast search using the consensus ADP-ribosyl cyclase family sequence. The putative initiation methionine(s) are indicated in green and the stop site is indicated in red. The primers used to clone the originally identified EST are shown in blue and the amino acids within the EST that are absolutely conserved within the cyclase family are indicated in yellow. FIG. 13B. Comparison of the amino acid sequence of S. mansoni SM38 with representative members of the ADP-ribosyl cyclase family. The absolutely conserved amino acids are indicated with * and conservative replacement amino acids are indicated with (:). The % identity and % similarity are indicated. The 10 conserved cysteine residues required for intradisulfide bonds and protein folding are indicated in red. The highly conserved "signature domain" within the active site of cyclase family members is shown in yellow, a critical substrate binding tryptophan residue is shown in green and the key catalytic glutamate residue is indicated in blue.

FIG. 14. SM38 is homologous to *Aplysia* ADP ribosyl cyclase and human CD38 cyclase. The protein sequence of SM38 was aligned with the protein sequences for *Aplysia* ADP-ribosyl cyclase (part a) and human ADP-ribosyl cyclase CD38 (part b). A high degree of homology (boxed residues) was observed with 21% identity between the *Aplysia* protein and SM38 and 23% identity between human CD38 and SM38. The conserved 10 cysteine residues present in all members of the cyclase protein family are also present in SM38 (shaded boxes). The two additional cysteines found in CD38 (underlined), but not in *Aplysia*, are also lacking in SM38. However, the SM38 protein contains two additional cysteine residues that are unique and are not found in either CD38 or *Aplysia* cyclase (underline). Most importantly, the active site catalytic residues identified for CD38 and *Aplysia* enzyme (starred residues) are also present in SM38.

FIG. 15. Amino acid sequence comparison between SM38 cloned from *S. mansoni* and a homologous protein identified from *S. japonicum* (Accession # AY222890). The conserved amino acids are indicated with * and the conservative replacement amino acids are indicated with a (:). The % identity and % similarity are indicated. The signal sequence, identified by the SignalP prediction program (Bendtsen, J. D. et al., 2004 *J Mol Biol;* 340:783-795), is indicated in green and the potential GPI anchor sequence (Eisenhaber, et al., 1998, *Protein Eng.,* 11:1155-1161) is indicated in magenta with the probable ω site for GPI addition shown in yellow. The 10 cysteine residues that are conserved among all cyclase family members are indicated in red and the two additional cysteine residues found only in *Schistoma* proteins are shown in orange. The invariant catalytic glutamate (E202) residue is shown in blue and the four potential N-linked glycosylation sites are in bold and italics.

Figure 16:
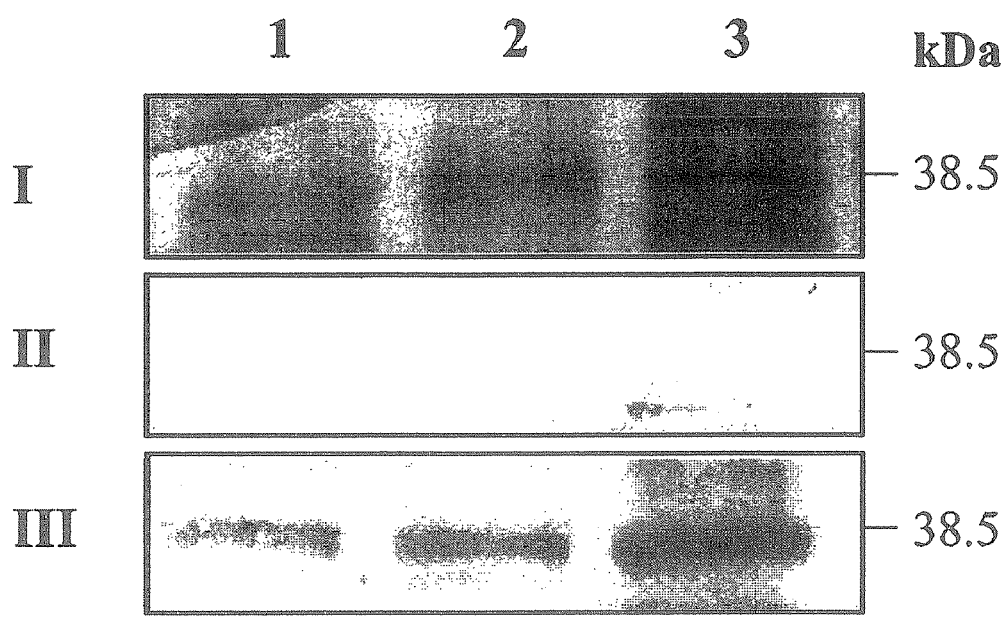

FIG. 16. Immunoreactivity of SM38 polyclonal antibodies with the native protein in schistosome extracts. Affinity purified SM38-polyclonal and normal mouse IgG were used to probe schistosome extracts separated onto 12% agarose gel. Panel I shows a Coomassie blue stained SDS-polyacrylamide gel (molecular weight range between and 33-45 kDa) of *S. mansoni* whole adult worm (lane 1), carcass (lane 2) and NP-40 (lane 3) extracts. Panel II shows reactivity of normal mouse IgG with schistosome extracts. No specific reactivity was found. Panel III shows that anti-SM38 mouse IgG detected a specific protein of an apparent molecular weight of about 38 kDa in all extracts tested.

FIG. 17. Reverse translation of SM38. The 303 amino acid coding region of SM38 was reverse-translated to identify a degenerate DNA sequence that would encode the SM38 protein.

FIG. 18. SM38 is a highly conserved protein expressed by two *Schistosoma* species. FIG. 18A. Phylogenetic comparison of cyclase family members. The amino acid sequences of the 11 previously identified members of the cyclase family (see Experimental Procedures for Accession #s) were compared to the two novel SM38 sequences and assembled into a phylogenetic tree. FIG. 18B. Proposed three dimensional structure of SM38. A homology model was constructed based on the crystallographic coordinates of both *Aplysia* ADP-ribosyl cyclase (PDB entry 1lbe) and human CD157 (PDB entry 1isf) using Modeller (50) and energy minimization using AMBER5. A ribbon representation of monomeric SM38 (green) is superimposed over that of human CD157 (red). The nicotinamide bound to CD157 (PDB entry 1ism) is shown as space filling model. Carbon atoms are colored in white, oxygen atoms in red, nitrogen atoms in dark blue and hydrogen atoms in cyan. FIG. 18C. Connoly surface of the putative active site of SM38. The surfaces of four important amino acids are highlighted using the color code defined in C. The amino acid residues shown include the putative catalytic Glu$^{202}$, the Glu$^{124}$ that regulates the ADP-ribosyl cyclase activity of CD38 and the substrate-binding Trp$^{165}$ and His$^{103}$. The rendering was performed using SYBYL (Tripos Inc.).

Figure 19:
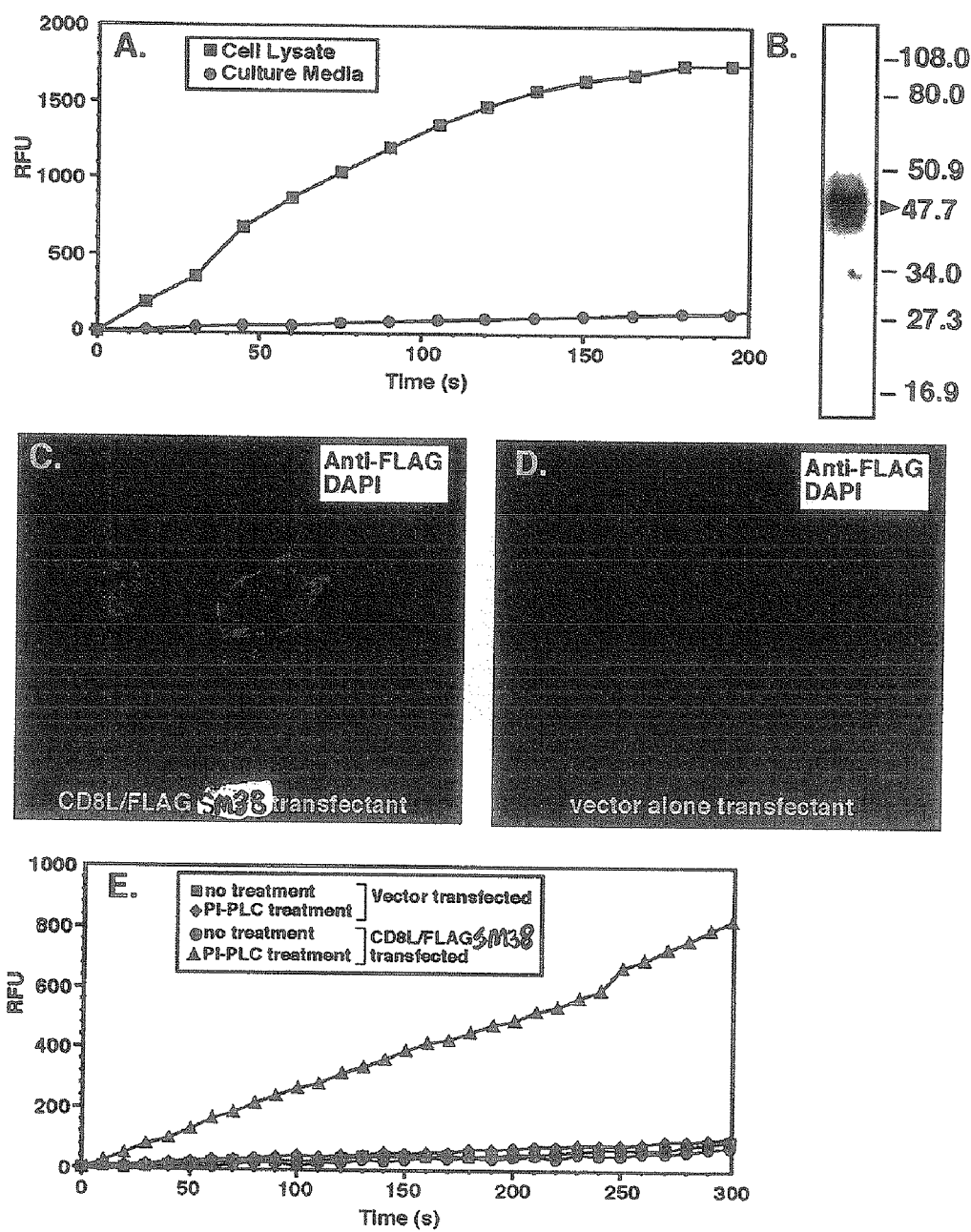

FIG. 19. *S. mansoni* SM38 is a GPI-anchored NADase when heterologously expressed in mammalian cells. FIG. 19A. Native SM38 is cell-associated. COS-7 cells were transiently transfected with the full length SM38 (SM38-opt). After three days, the culture media (circles) and cells were collected separately. The cells were lysed and the detergent soluble proteins were collected (squares). Aliquots of the cell lysate and the conditioned tissue culture media were incubated with ε-NAD$^+$ and conversion of ε-NAD$^+$ to fluorescent ε-ADPR was measured over time in a microplate fluorimeter. Data is represented in relative fluorescent units (RFU) vs time. No enzyme activity was observed in non-transfected COS-7 cells or COS-7 cells transfected with the empty vector (data not shown). FIG. 19B. SM38 is expressed as a ~48 kD protein in COS-7 cells. The native signal sequence of *S. mansoni* SM38 was replaced with the mammalian CD8 signal sequence and a FLAG tag (CD8L/FLAG-SM38). Cell lysates of COS-7 cells transiently transfected with the CD8L/FLAG-SM38 construct were analyzed by western blot using an anti-FLAG antibody to identify SM38. FIGS. 19C-D. SM38 is expressed as a plasma membrane-associated protein in transfected COS-7 cells. COS-7 cells were transiently transfected on slides with CD8L/FLAG-SM38 (panel C) or the empty expression vector (panel D). The transfected cells were fixed and stained with a biotinylated anti-FLAG antibody followed by fluorochrome coupled strep-avidin (red) and a nuclear counterstain (DAPI, blue). Cells were analyzed by fluorescent microscopy. FIG. 19E. SM38 is expressed as a GPI-anchored protein in COS-7 cells. COS-7 cells were transiently transfected with either CD8L/FLAG-SM38 (circles and triangles) or the control expression vector (squares and diamonds). Three days later the transfected cells were washed and then cultured in fresh media (squares and circles) or fresh media containing PI-PLC (diamonds and triangles). Two hours later the media was collected and incubated in the presence of ε-NAD$^+$. Conversion of ε-NAD$^+$ to fluorescent ε-ADPR was measured in a microplate fluorimeter and is reported as RFU vs time.

Figure 20:
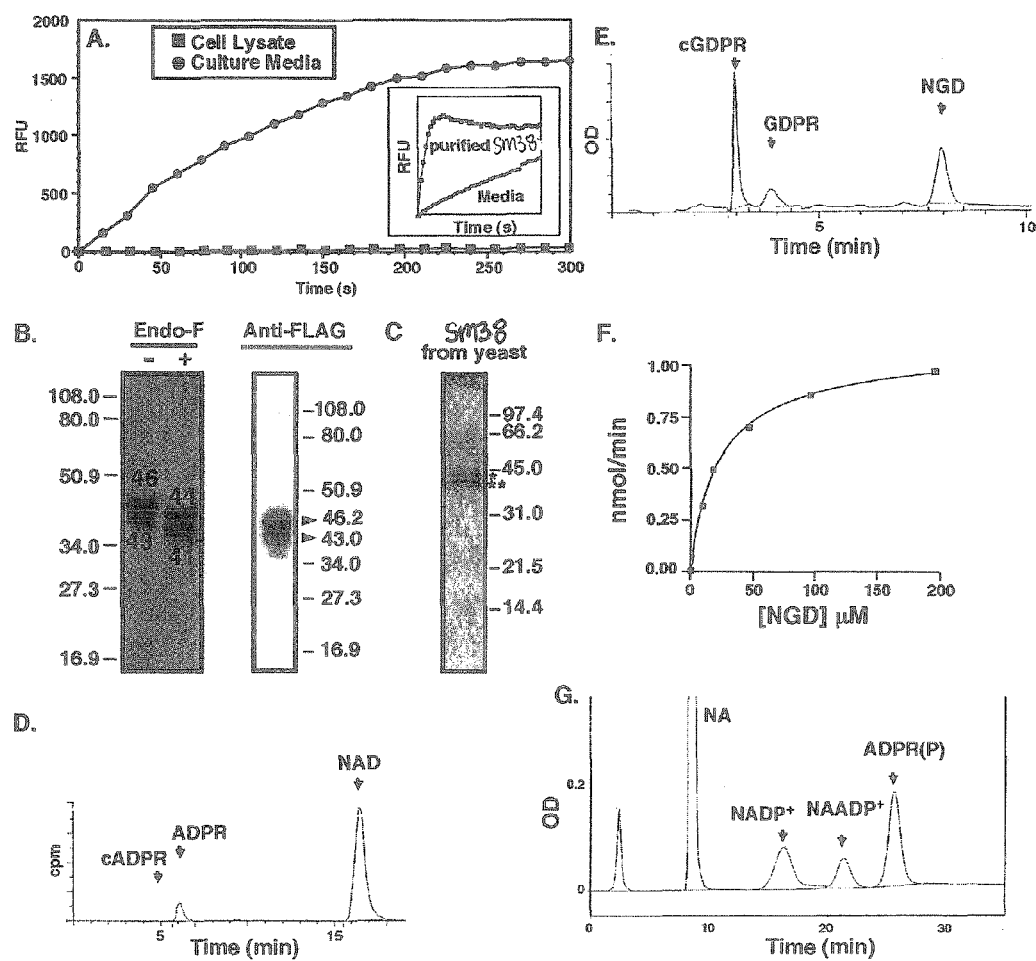

FIG. 20. Recombinant soluble SM38 catalyzes NAD glycohydrolase, cyclase and transglycosidation reactions. FIG. 20A. Recombinant soluble SM38 is secreted. COS-7 cells were transiently transfected with CD8L/FLAG-SM38ΔGPI, a construct lacking the GPI anchor sequence. Transfected COS-7 cells were lysed, detergent soluble proteins were collected and aliquots of the cell lysate (squares) and culture media (circles) were collected. Aliquots were then incubated with ε-NAD$^+$ and conversion and accumulation of fluorescent ε-ADPR was measured in a microplate fluorimeter. The remaining culture media was purified over an anti-FLAG column and aliquots were again tested for NADase activity using ε-NAD$^+$ as the substrate (inset). Data is reported in RFU vs time. FIG. 20B. Recombinant soluble SM38 is glycosylated in mammalian cells. Recombinant soluble SM38 was purified from COS-7 cells transiently transfected with CD8L/FLAG-SM38ΔGPI. Affinity purified SM38 was incubated in the presence or absence of Endoglycosidase-F1 (Endo-F) and the proteins were separated by SDS-PAGE and analyzed by silver staining (left panel) or western blotting with anti-FLAG antibody (right panel). The molecular weight of soluble recombinant SM38 is indicated. FIG. 20C. Recombinant soluble SM38 is expressed in *Pichia pastoris*. *Pichia* were transformed with an expression vector containing the SM38 ecto-domain. A stable clone was selected and SM38 production and secretion was induced with methanol. Secreted SM38 was purified from the media by chromatography and analyzed by SDS-PAGE and Coomassie staining. The molecular weights of the purified proteins are 45.2 (*) and 43.6 (**) kDa. FIG. 20D. Soluble recombinant SM38 catalyzes the transformation of $NAD^+$ to ADPR. Recombinant soluble SM38 was purified from *Pichia* and then incubated with radio-labeled $NAD^+$. The accumulation of radio-labeled ADPR and cADPR was measured by HPLC. FIGS. 20E-F. Soluble recombinant SM38 catalyzes the transformation of $NGD^+$ to cyclic GDP-ribose. Purified recombinant soluble SM38 was incubated with increasing quantities of $NGD^+$ and the accumulation of cyclic GDPR and GDPR was detected by HPLC and UV detection (260 nm) at various time points. 20G. SM38 catalyzes the transglycosidation of $NADP^+$ to $NAADP^+$. $NADP^+$ (1 mM) was incubated with recombinant purified SM38 at 37° C. in the presence of 20 mM nicotinic acid (NA). Aliquots were analyzed by HPLC. The compounds were detected by UV absorbance at 260 nm. ADPR(P), adenosine diphosphoribose 2'-phosphate.

Figure 21:
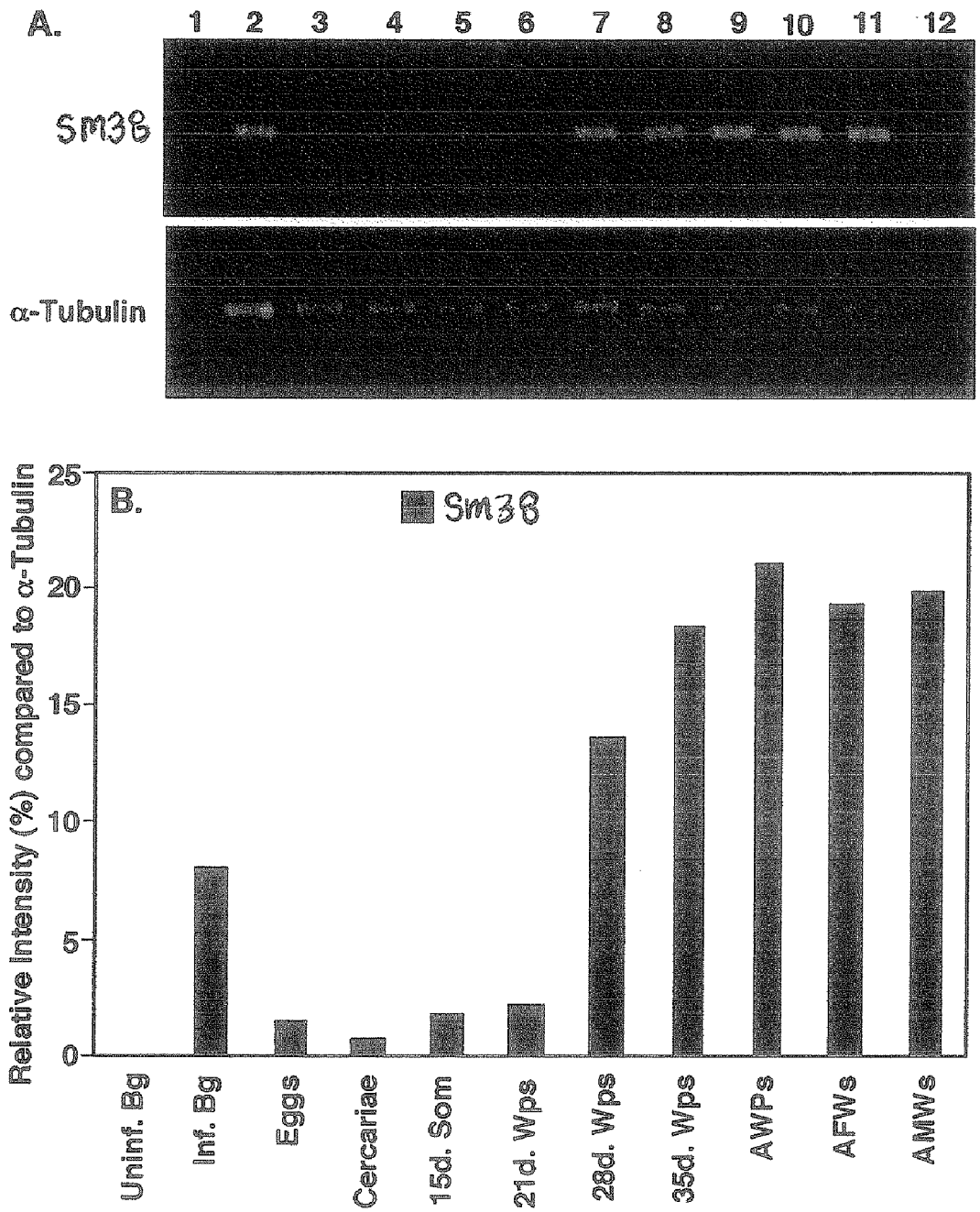

FIG. 21. SM38 expression is developmentally regulated in *S. mansoni*. FIG. 21A. cDNA prepared from RNA isolated from multiple developmental stages of *S. mansoni* was used as the template for RT-PCR reactions using SM38-specific primers. Schistosome specific α-tubulin primers were used to amplify a constitutively transcribed internal control gene. Tested stages are numbered from 1 to 12 and they represent the following: uninfected *B. glabrata*, 30-day infected *B. glabrata*, *S. mansoni* eggs, *S. mansoni* cercariae, *S. mansoni* 15-day schistosomules, 21-day schistosomules, 28-day worms, 35-day worms, adult (>42-day old) worm pairs, adult female worms, adult male worms and no reverse transcriptase (—RT) control, respectively. FIG. 21B. Bar-graph representation of the average expression level of SM38 exhibited by each tested developmental stage of the parasite life cycle as percentage of levels of α-tubulin internal control. Data shown are averages of values quantified from three independent PCR amplifications. Background (—RT control) was subtracted from each of the analyzed samples.

Figure 22:
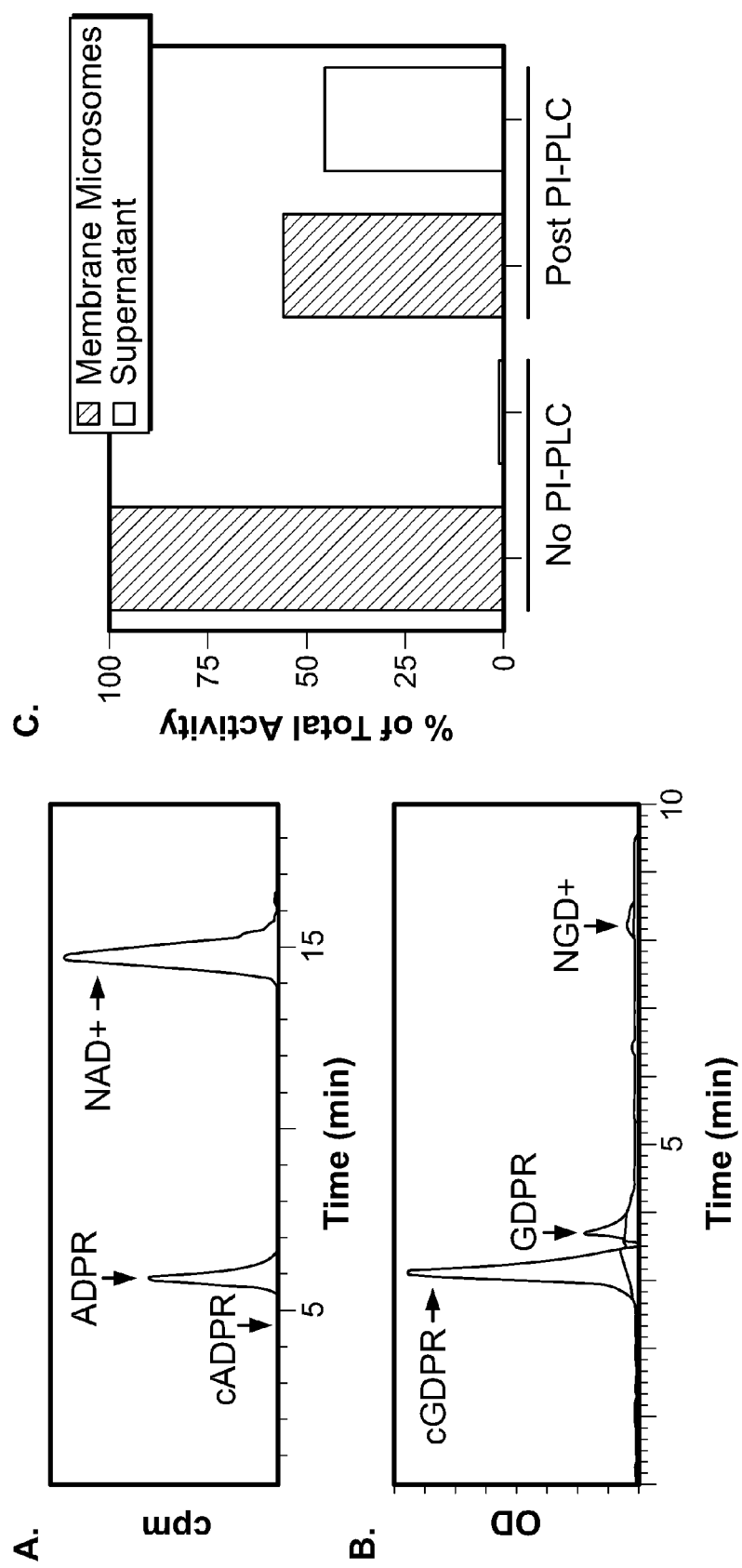
Figure 22:
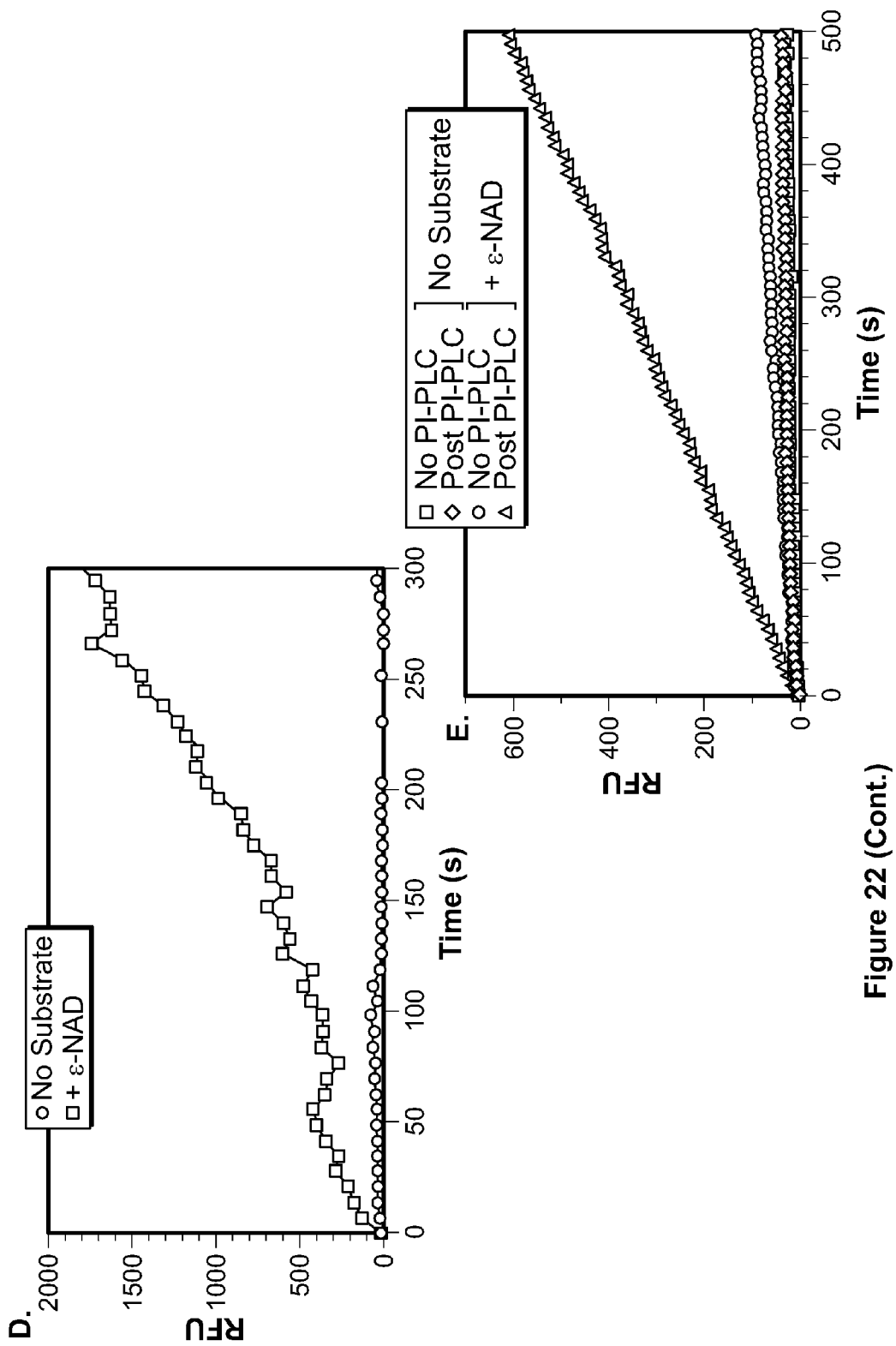

FIG. 22. Adult *S. mansoni* worms express a GPI-anchored NADase on the outer membrane. FIGS. 22A-C. Adult *S. mansoni* worms express a GPI-anchored $NAD^+$ glycohydrolase and $NGD^+$ cyclase. Membrane microsomes were prepared from 2 g of frozen adult *S. mansoni* worms. The microsomes were resuspended in buffer and incubated with $^{14}C$-labeled $NAD^+$ (A) or unlabeled $NGD^+$ (B). Product formation was measured by HPLC as described in FIG. 20. In panel C, the membrane microsomes were incubated in the presence or absence of PI-PLC for two h. The supernatant and membrane fractions were collected separately and then incubated with $^{14}C$-labeled $NAD^+$. ADPR production was measured by HPLC and results are presented as % activity compared to the non-treated membrane fraction. The specific activity of non-treated membrane microsomes was 36 nmol/min/mg protein. FIG. 22D. Adult *S. mansoni* worms express an outer membrane $NAD^+$ glycohydrolase. Ten live adult *S. mansoni* worms were placed in single wells of a 96 well plate and were incubated in media (circles) or media containing ε-NAD* (squares) and conversion of ε-$NAD^+$ to fluorescent ε-ADPR was measured in a microplate fluorimeter and is reported in RFU vs time. FIG. 22E. Adult *S. mansoni* worms express a GPI-anchored outer tegument NADase. Ten live adult *S. mansoni* worms were placed in single wells of a 96 well plate and were then incubated in the presence (diamonds and triangles) or absence (squares and circles) of PI-PLC for 2 h. The buffer from each of the wells was removed and then incubated in the presence (circles and triangles) or absence (squares and diamonds) of ε-$NAD^+$. Production of fluorescent c-ADPR was measured in a microplate fluorimeter and is reported as RFU over time.

Figure 23:
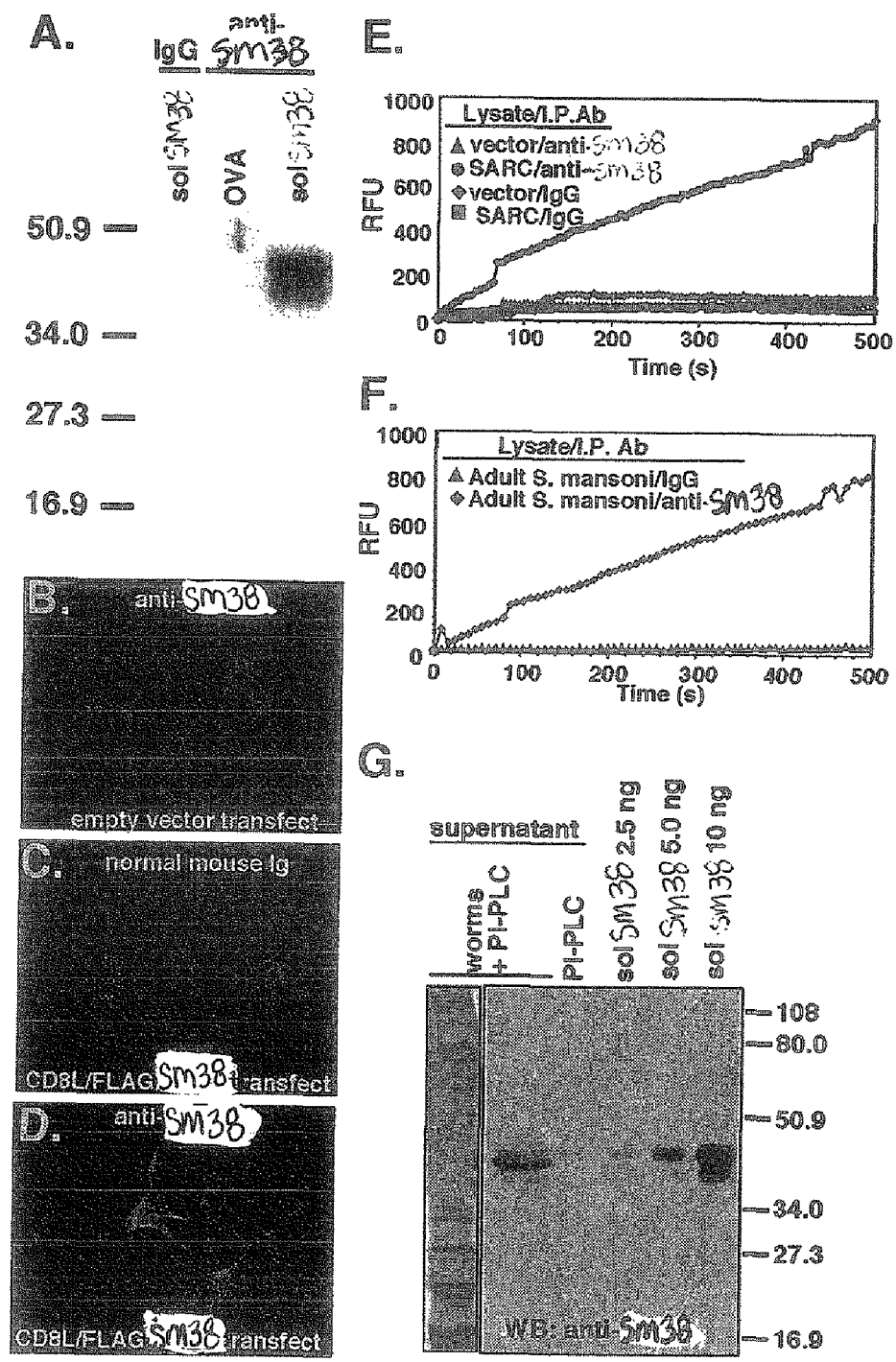

FIG. 23. Antiserum raised against the SM38 cDNA immunoprecipitates enzymatically active SM38 from adult *S. mansoni* worms. FIG. 23A. Antibodies raised in response to SM38 cDNA immunization recognize recombinant soluble SM38. Control serum (IgG) and antiserum collected from mice vaccinated with the CD8L/FLAG-SM38ΔGPI construct (anti-SM38) were used to probe western blots containing recombinant soluble SM38 or irrelevant protein (ovalbumin, OVA). FIGS. 23B-D. Antiserum raised in response to immunization with SM38 cDNAs specifically recognize plasma membrane-associated SM38. COS-7 cells were transiently transfected on slides with CD8L/FLAG-SM38 (C-D) or the empty expression vector (B). Three days later the cells were stained with anti-SM38 antiserum (B, D) or normal mouse serum (C) followed by fluorochrome coupled anti-mouse IgG (red) and a nuclear counterstain (DAPI, blue), FIG. 23E. Anti-SM38 antibodies immunoprecipitate functional SM38 protein from transfected COS-7 cells. COS-7 cells were transiently transfected with CD8L/FLAG-SM38 (squares and circles) or the empty expression vector (diamonds and triangles). Three days later the cells were lysed and the lysates were incubated with either normal mouse IgG protein G beads (diamonds and squares) or with anti-SM38 protein G beads (triangles and circles). The immunoprecipitated protein/bead complexes were incubated in the presence of ε-$NAD^+$ and the accumulation of fluorescent ε-ADPR was measured using a microplate fluorimeter. Data is reported in RFU vs time. 23F. Antibodies raised in response to SM38 cDNA immunization immunoprecipitate enzymatically active SM38 from adult *S. mansoni* lysates. Adult *S. mansoni* worms were lysed in detergent and the lysates were incubated with either normal mouse IgG protein G beads (triangles) or with anti-SM38 protein G beads (diamonds). The immunoprecipitated protein/bead complexes were incubated in the presence of s-$NAD^+$ and the accumulation of fluorescent ε-ADPR was measured using a microplate fluorimeter. Data is reported as RFUs vs time. FIG. 23G. Antibodies raised in response to SM38 cDNA immunization recognize a GPI-anchored protein expressed by adult *S. mansoni* worms. Live adult worms were incubated in HBSS in the presence of PI-PLC for 2 h. The supernatant was collected, concentrated and then electrophoresed on a SDS-PAGE gel. 15% of the total protein was analyzed by silver staining and western blot using anti-SM38 anti-serum. Control lanes include PI-PLC alone and increasing concentrations of recombinant soluble SM38.

Figure 24:
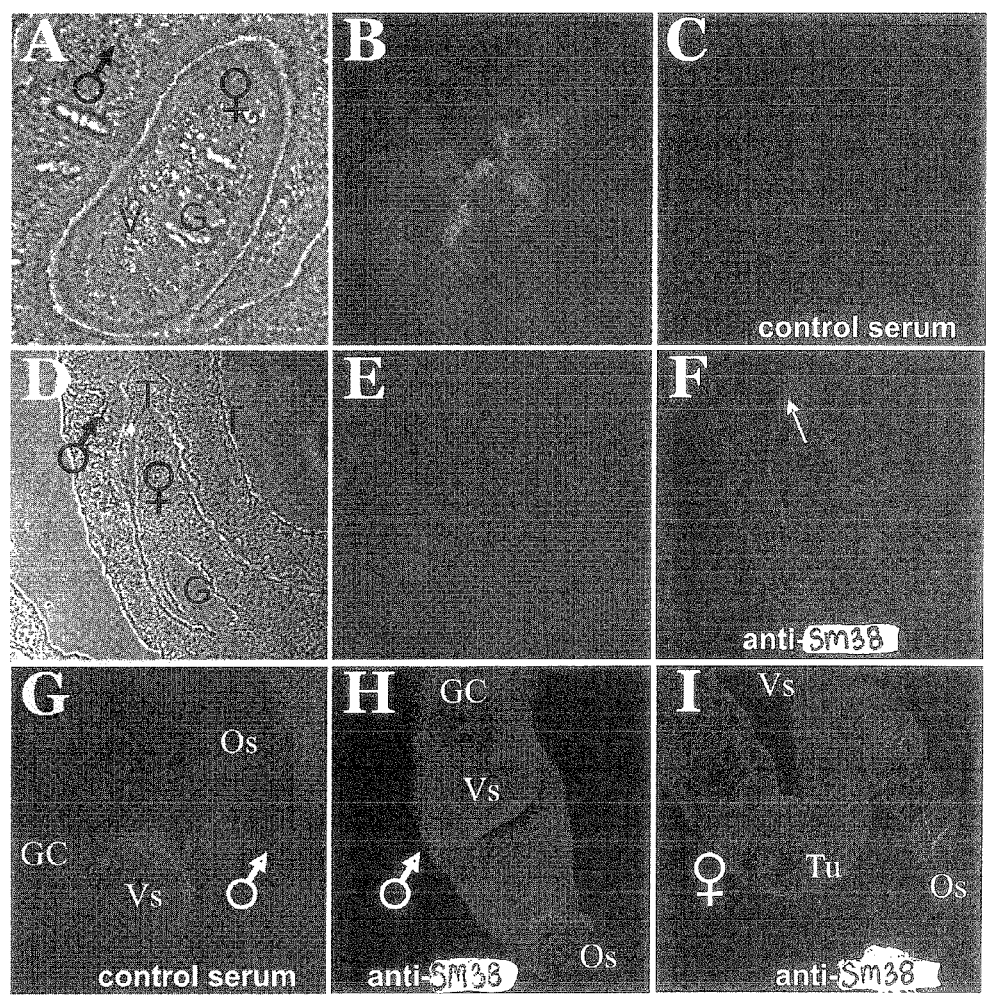

FIG. 24. Immunohistochemical localization of SM38 in adult *S. mansoni*. Adult 87 schistosome cryosections (A-F) and live or acetone-fixed whole-mount adult worms (G-I) were prepared. Panels A and D represent phase contrast fields. Samples visualized using a green fluorescence filter (Panels B and E) indicate auto-fluorescent structures including female worm vitellaria (Panel B). To localize SM38, sections and whole mounts were stained with the IgG fraction purified from the anti-SM38 antiserum (Panels F, H, I) or with normal mouse IgG (Panels C, G) followed by staining with anti-mouse IgG and Alexa Fluor 647 conjugated streptavidin. SM38 was visualized using a far-red fluorescence filter. Slides stained with normal mouse IgG did not show any specific reactivity (Panel C, G), while slides stained with anti-SM38 antibody showed specific staining in the tegument layer of male worm gynecophoric canal (arrow, Panel F). Acetone-fixed whole adult worms (male worm shown)

stained with anti-SM38 mouse IgG showed strong overall fluorescence (Panel H), while in live whole worms (female shown, Panel I) fluorescence was more localized to oral sucker (Os), ventral sucker (Vs) and tubercles (Tu). V stands for vitellaria, G is gut, T is tegument and GC is male gynecophoric canal. Sections and whole worms were photographed at 200× and 100× magnifications, respectively.

Figure 25:
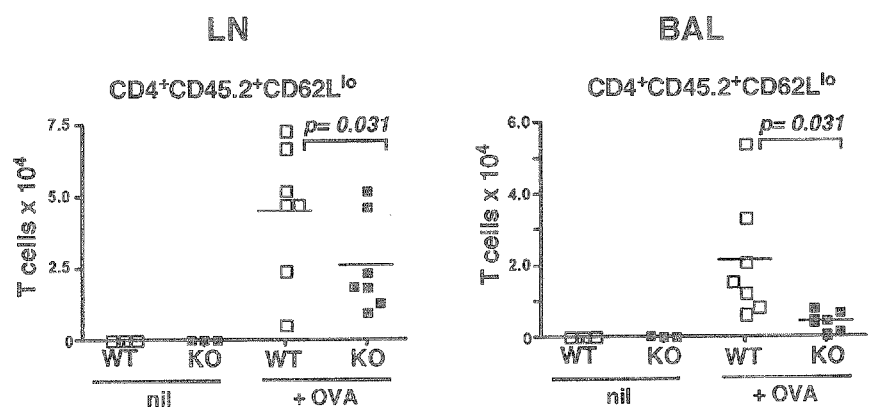
Figure 26:
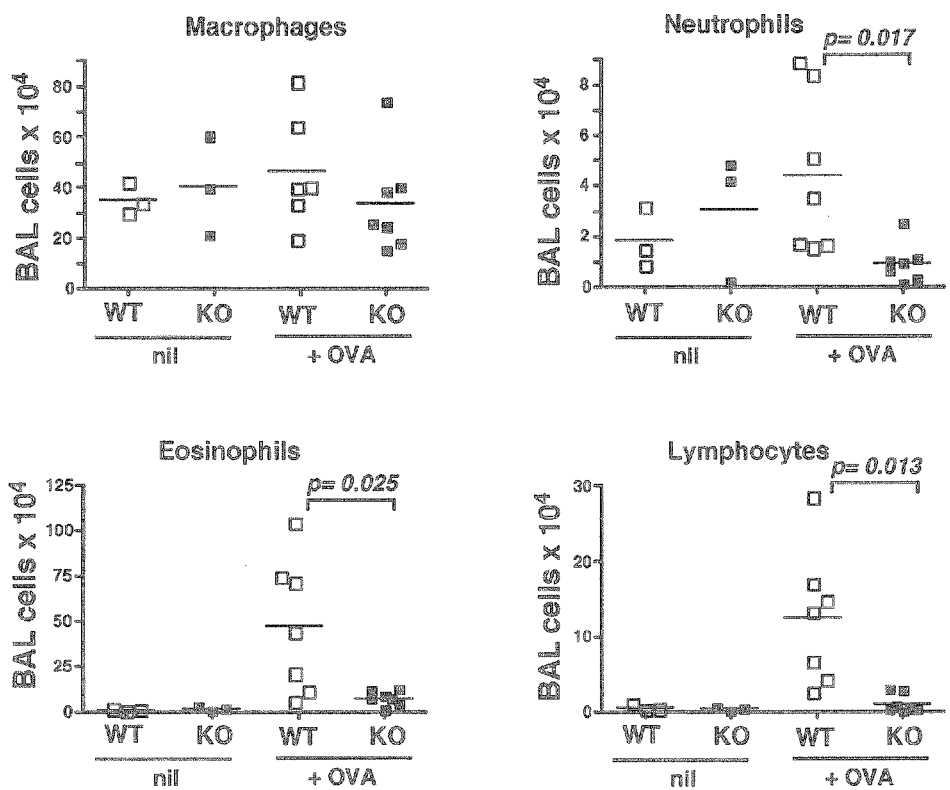

FIGS. 25-26. CD38 expression on allergen-specific T cells (or autoimmune T cells) is required for either their maturation into differentiated effector cells or for their migration to sites of inflammation. OVA-specific T cells which are CD38 deficient are reduced in number in both the lymph node and at the site of inflammation in the lungs of mice sensitized with 10 μg NP-OVA (n=7 mice/group) or PBS administered (n=3 mice/group). Similarly, the allergen-induced inflammatory response is suppressed in the lungs of mice receiving CD38 deficient T cells. The number of donor OVA-specific T cells with an activated phenotype) (CD45.2$^+$CD4$^+$CD62L$^{lo}$) present in the lymph node and BAL of the sham and allergen-challenged host is depicted in FIG. 25. The number of infiltrating inflammatory cells to the lungs of the mice is indicated in FIG. 26.

Figure 27:
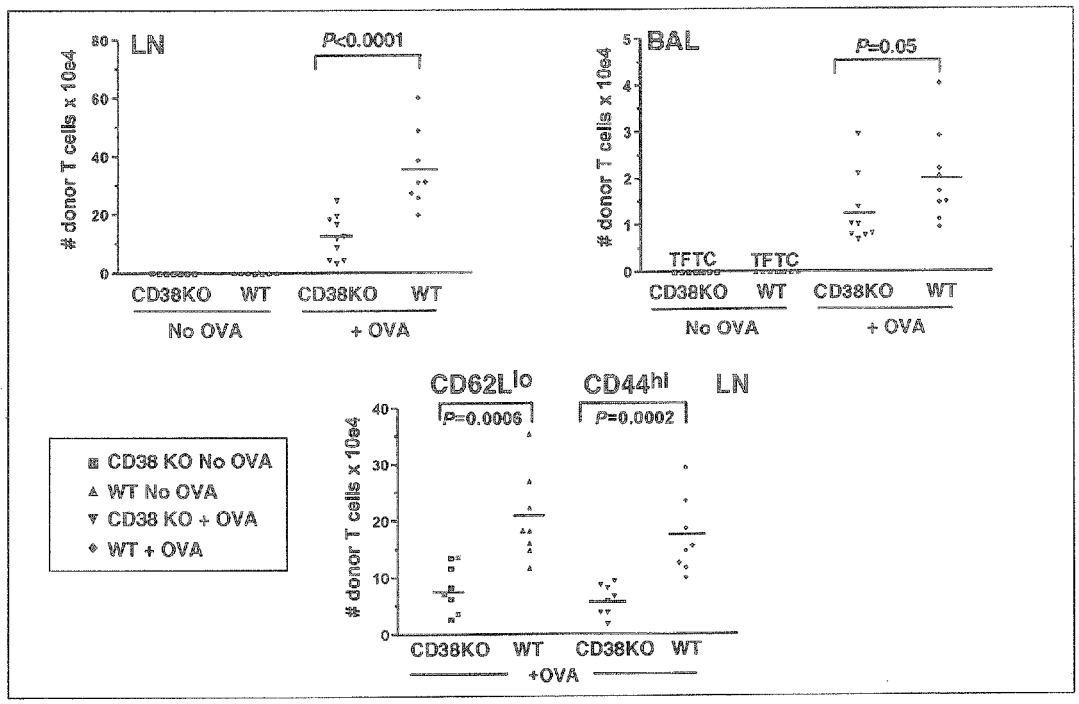
Figure 28:
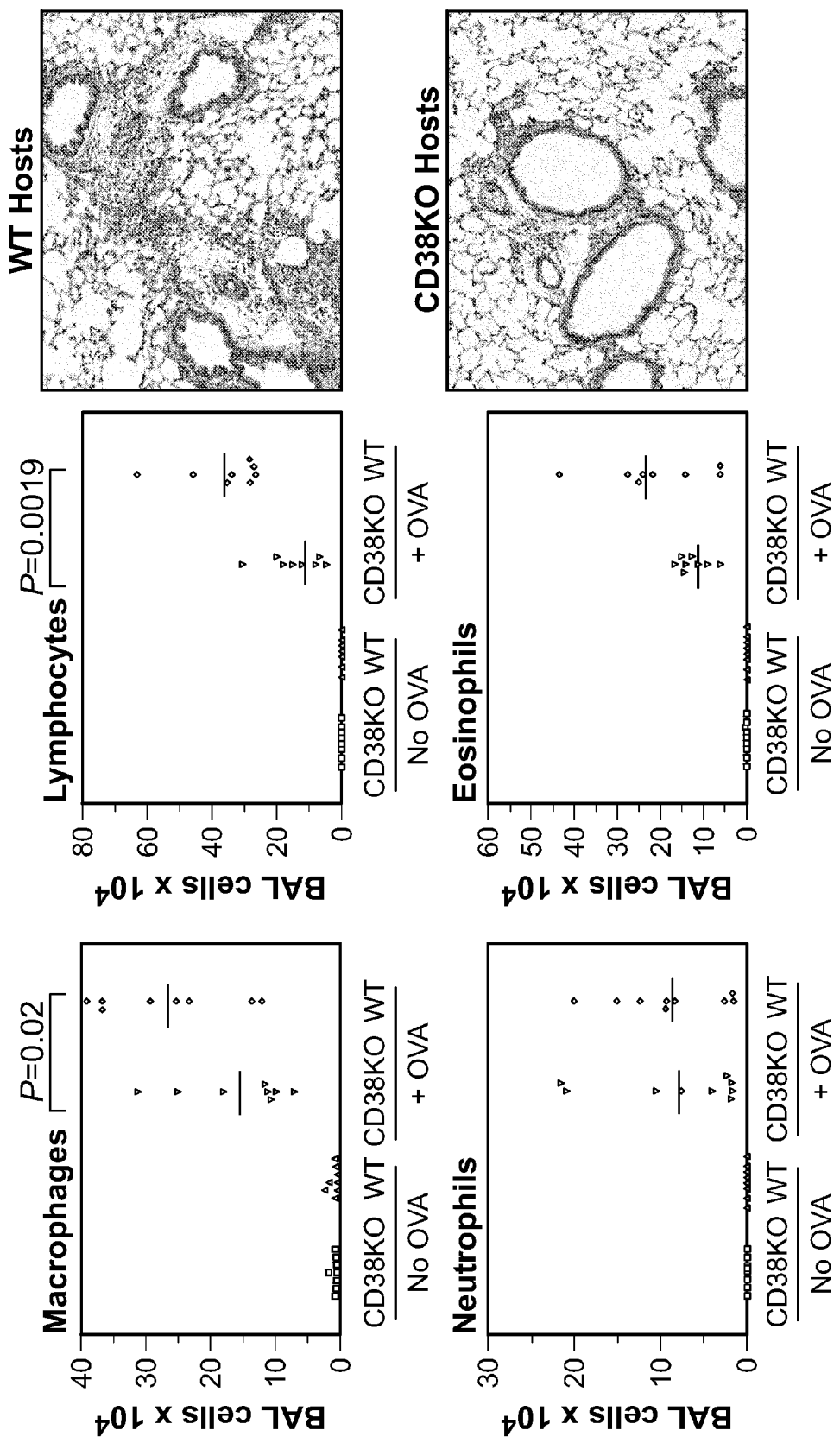

FIGS. 27-28. Priming of inflammatory allergen-specific T cells is reduced in CD38 deficient mice, even when the T cells are from normal animals. The number of donor OVA-specific T cells (CD45.2$^+$CD4$^+$) present in the lymph node and BAL of sham and allergen-challenged hosts is depicted in FIG. 27. The number of activated CD62Llo donor T cells present in the lymph nodes is also shown in FIG. 27. The number of infiltrating inflammatory cells to the lungs of the mice is indicated in FIG. 28. A representative H&E section of the lungs of OVA challenged WT or CD38 KO mice is also depicted in FIG. 28.

Figure 29:
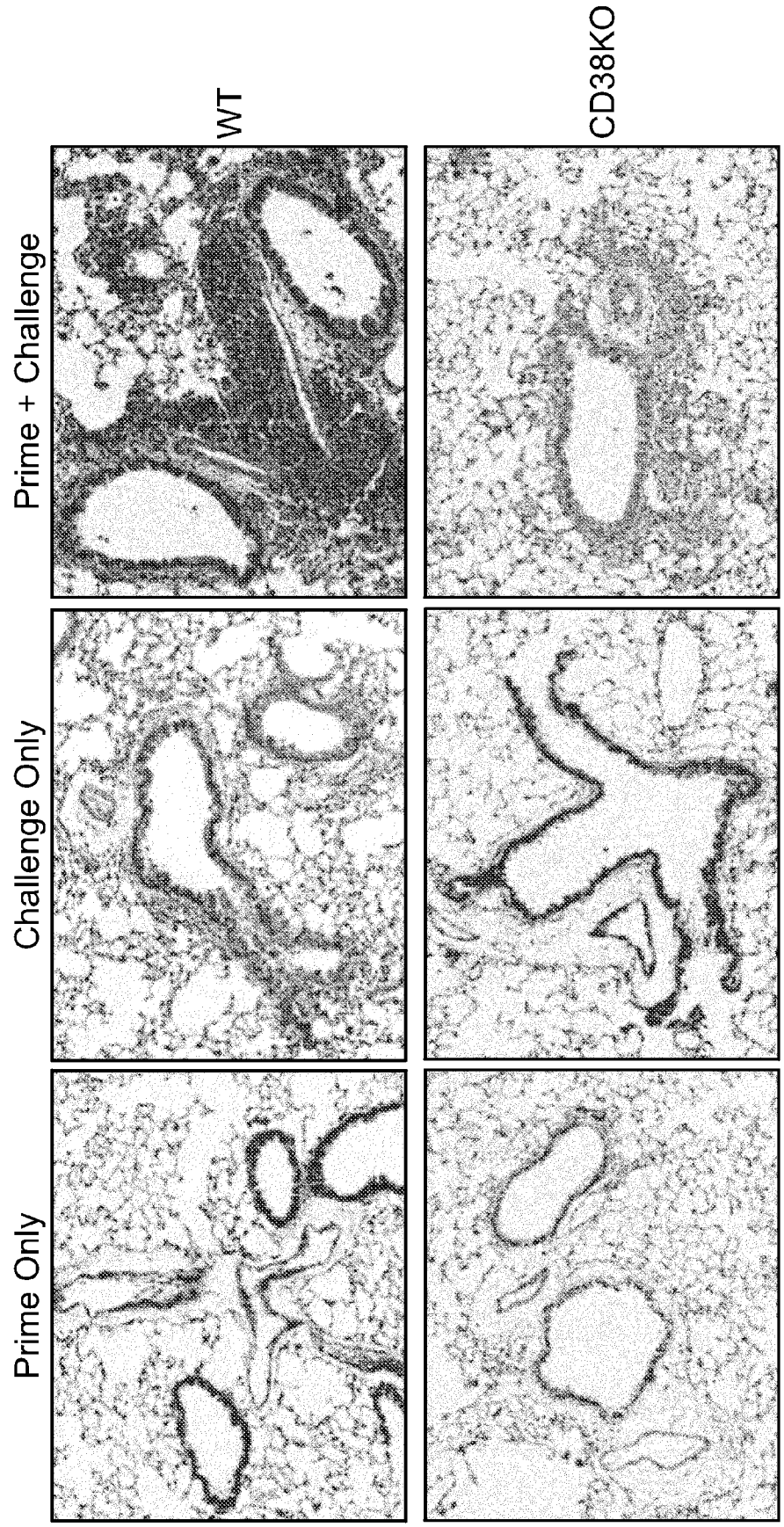

FIG. 29. Allergen-induced inflammatory responses in the lungs are reduced in CD38 deficient mice. CD38 deficient (KO) or normal C57BL/6 (WT) mice were primed with ovalbumin (OVA) on day 0 or were inoculated with PBS. On day 42 post-immunization, animals were either left untreated (prime only) or were challenged with 10 μg OVA administered intranasally I time/day for the next 7 days (prime+challenge group and challenge only group). The lungs were isolated from all groups of mice one day after the last administration of OVA and were prepared for histological examination. H&E stained paraffin sections of a representative animal from each group are shown.

Figure 30:
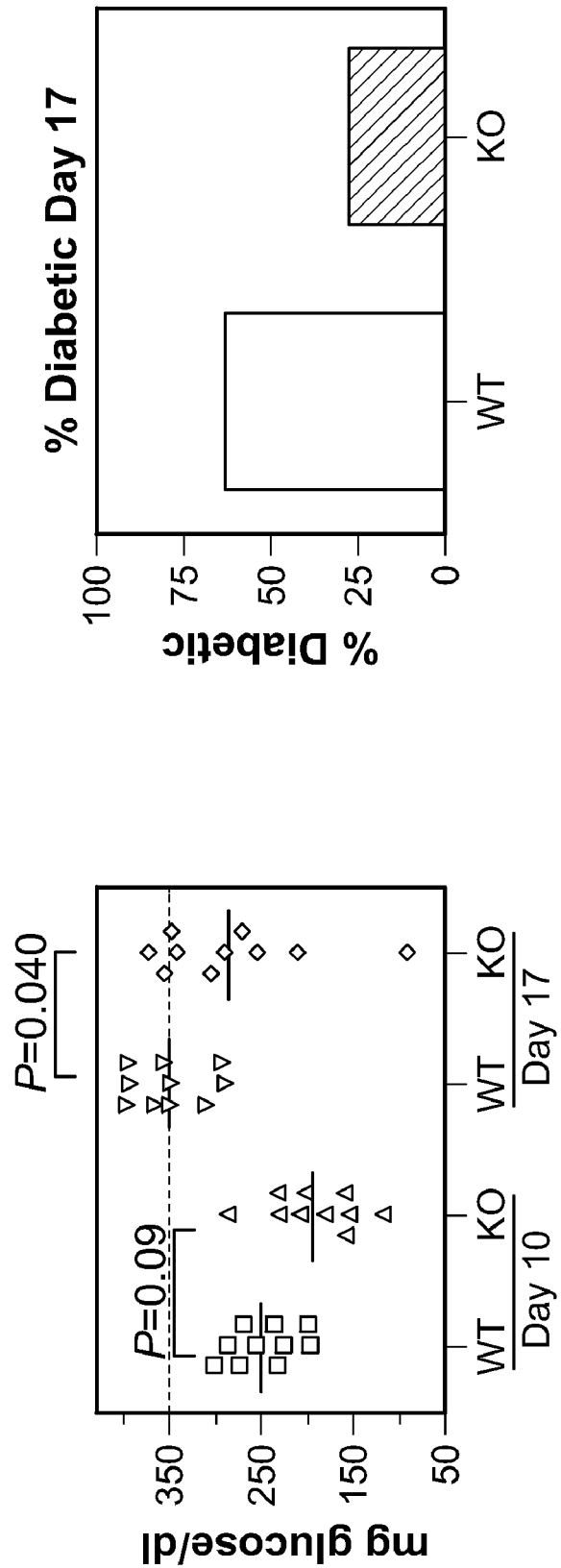

FIG. 30. Diabetes onset is delayed in CD38 deficient mice. CD38 deficient (KO) or normal BALB/c (WT) mice were injected with Streptozotocin. Blood glucose levels were measured 10 and 17 days after the last STZ injection.

5. DETAILED DESCRIPTION OF THE INVENTION

The present invention relates to methods for modulating the migratory activity of cells involving the regulation of CD38 ADP-ribosyl cyclase activity. The invention is based on the discovery that granulocytes such as neutrophils and eosinophils from CD38KO mice cannot be efficiently recruited to sites of inflammation and infection in the body. The invention is based on the discovery that although CD38 ADP-ribosyl cyclase activity is not essential for the initial activation of granulocytes such as neutrophils, it is critically important in regulating neutrophil chemotaxis both in vivo and in vitro. In particular, cADPR, a product of CD38 ADP-ribosyl cyclase activity, is required to induce calcium release from calcium stores present within neutrophils. The release of calcium from this specialized store is necessary for activation and opening of plasma membrane channels resulting in a capacitative influx of calcium that subsequently mediates the direct migration of neutrophils toward chemoattractants and/or inflammatory products.

The present invention encompasses screening assays designed for the identification of modulators, such as agonists and antagonists, of CD38 enzyme activity and/or modulators of cADPR dependent calcium responses and chemotaxis. The invention further relates to the use of such modulators in the treatment of disorders based on the CD38 controlled migratory activity of cells to chemoattractants and inflammatory products. Such disorders include, but are not limited to, inflammation, ischemia, autoimmune disease, asthma, diabetes, arthritis, allergies, infections and organ transplant rejection.

The present invention also relates to the identification, isolation and characterization of the CD38 homologue, SM38, from the parasite S. mansoni. The invention encompasses screening assays to identify related enzymes in other pathogenic micro-organisms, such as helminths, as well as compositions and assays to screen for compounds that modulate the activity and expression of SM38. The invention further relates to the use of such modulators to treat pathogenic disorders in animals and humans infected with organisms expressing SM38 or structurally related molecules.

Various aspects of the invention are described in greater detail in the subsections below.

5.1 The SM38 Gene

The cDNA sequence and deduced amino acid sequence of S mansoni SM38 is shown in FIG. 13A (ATCC Deposit Nos: PTA-3780 (plasmid pCR2.1-TOPO in E. coli: SM38 5-18; PTA-3781 (plasmid SK in E. coli: SM38 LC12). The SM38 cDNA was translated in all reading frames and an open reading frame of 303 amino acids was identified. The initiation codon is located at nucleotide position 71 and the termination codon is found at nucleotide position 981.

The SM38 nucleotide sequences of the invention include: (a) the DNA sequences shown in FIG. 13; (b) a nucleotide sequences that encodes the amino acid sequence shown in FIG. 13; (c) any nucleotide sequence that (i) hybridizes to the nucleotide sequence set forth in (a) or (b) under stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and (ii) encodes a functionally equivalent gene product; and (d) any nucleotide sequence that hybridizes to a DNA sequence that encodes the amino acid sequence shown in FIG. 13 under less stringent conditions, such as moderately stringent conditions, e.g., washing in 0.2×SSC/0.1% SDS at 42° C. (Ausubel et al., 1989 supra), yet which still encodes a functionally equivalent SM38 gene product. Functional equivalents of the SM38 protein include naturally occurring SM38 present in species other than S. mansoni. The invention also includes degenerate variants of sequences (a) through (d). The invention also includes nucleic acid molecules, that may encode or act as SM38 antisense molecules, useful, for example, in SM38 gene regulation (for and/or as antisense primers in amplification reactions of SM38 gene nucleic acid sequences).

In addition to the SM38 nucleotide sequences described above, homologs of the SM38 gene present in other species can be identified and readily isolated, without undue experimentation, by molecular biological techniques well known in the art. For example, cDNA libraries, or genomic DNA libraries derived from the organism of interest can be screened by hybridization using the nucleotides described herein as hybridization or amplification probes.

The invention also encompasses nucleotide sequences that encode mutant SM38s, peptide fragments of the SM38, truncated SM38, and SM38 fusion proteins. These include, but are not limited to nucleotide sequences encoding polypeptides or peptides corresponding to the cyclase domain of SM38 or portions of this domain; truncated SM38s in which the domain is deleted, e.g., a functional SM38 lacking all or a portion of the cyclase region. Certain of these truncated or mutant SM38 proteins may act as dominant-negative inhibitors of the native SM38 protein. Nucleotides encoding fusion proteins may include but are not limited to full length SM38, truncated SM38 or peptide fragments of SM38 fused to an unrelated protein or peptide such as an enzyme, fluorescent protein, luminescent protein, etc., which can be used as a marker.

SM38 nucleotide sequences may be isolated using a variety of different methods known to those skilled in the art. For example, a cDNA library constructed using RNA from cells or tissue known to express SM38 can be screened using a labeled SM38 probe. Alternatively, a genomic library may be screened to derive nucleic acid molecules encoding the SM38 protein. Further, SM38 nucleic acid sequences may be derived by performing PCR using two oligonucleotide primers designed on the basis of the SM38 nucleotide sequences disclosed herein. The template for the reaction may be cDNA obtained by reverse transcription of mRNA prepared from cell lines or tissue known to express SM38.

The invention also encompasses (a) DNA vectors that contain any of the foregoing SM38 sequences and/or their complements (i.e., antisense); (b) DNA expression vectors that contain any of the foregoing SM38 sequences operatively associated with a regulatory element that directs the expression of the SM38 coding sequences; (c) genetically engineered host cells that contain any of the foregoing SM38 sequences operatively associated with a regulatory element that directs the expression of the SM38 coding sequences in the host cell; and (d) transgenic mice or other organisms that contain any of the foregoing SM38 sequences. As used herein, regulatory elements include but are not limited to inducible and non-inducible promoters, enhancers, operators and other elements known to those skilled in the art that drive and regulate expression.

5.1.2. SM38 Proteins and Polypeptides

SM38 protein, polypeptides and peptide fragments, mutated, truncated or deleted forms of the SM38 and/or SM38 fusion proteins can be prepared for a variety of uses, including but not limited to the generation of antibodies, the identification of other cellular gene products involved in the regulation of SM38 activity, and the screening for compounds that can be used to modulate the activity of SM38.

FIG. 13 shows the deduced amino acid sequence of the SM38 protein. The SM38 amino acid sequences of the invention include the amino acid sequence shown in FIG. 13. Further, SM38s of other species are encompassed by the invention. In fact, any SM38 protein encoded by the SM38 nucleotide sequences described above is within the scope of the invention.

The invention also encompasses proteins that are functionally equivalent to the SM38 encoded by the nucleotide sequences described in Section 5.1, as judged by any of a number of criteria, including but not limited to the ability to catalyze the production of the calcium mobilizing second messenger, cADPR and thereby regulate calcium response. Such functionally equivalent SM38 proteins include but are not limited to proteins having additions or substitutions of amino acid residues within the amino acid sequence encoded by the SM38 nucleotide sequences described, above, in Section 5.1, but which result in a silent change, thus producing a functionally equivalent gene product.

Peptides corresponding to one or more domains of SM38 as well as fusion proteins in which the full length SM38, a SM38 peptide or a truncated SM38 is fused to an unrelated protein are also within the scope of the invention and can be designed on the basis of the SM38 nucleotide and SM38 amino acid sequences disclosed herein. Such fusion proteins include fusions to an enzyme, fluorescent protein, or luminescent protein which provide a marker function.

While the SM38 polypeptides and peptides can be chemically synthesized (e.g., see Creighton, 1983, Proteins: Structures and Molecular Principles, W.H. Freeman & Co., N.Y.), large polypeptides derived from SM38 and the full length SM38 itself may be advantageously produced by recombinant DNA technology using techniques well known in the art for expressing a nucleic acid containing SM38 gene sequences and/or coding sequences. Such methods can be used to construct expression vectors containing the SM38 nucleotide sequences described in Section 5.1 and appropriate transcriptional and translational control signals. These methods include, for example, in vitro recombinant DNA techniques, synthetic techniques, and in vivo genetic recombination. (See, for example, the techniques described in Sambrook et al., 1989, supra, and Ausubel et al., 1989, supra).

A variety of host-expression vector systems may be utilized to express the SM38 nucleotide sequences of the invention. Where the SM38 peptide or polypeptide is expressed as a soluble derivative and is not secreted, the peptide or polypeptide can be recovered from the host cell. Alternatively, where the SM38 peptide or polypeptide is secreted the peptide or polypeptides may be recovered from the culture media. Purification or enrichment of the SM38 from such expression systems can be accomplished using appropriate detergents and lipid micelles and methods well known to those skilled in the art. Such engineered host cells themselves may be used in situations where it is important not only to retain the structural and functional characteristics of the SM38, but to assess biological activity, i.e., in drug screening assays.

The expression systems that may be used for purposes of the invention include but are not limited to microorganisms such as bacteria transformed with recombinant bacteriophage, plasmid or cosmid DNA expression vectors containing SM38 nucleotide sequences; yeast transformed with recombinant yeast expression vectors containing SM38 nucleotide sequences or mammalian cell systems harboring recombinant expression constructs containing promoters derived from the genome of mammalian cells or from mammalian viruses.

Appropriate expression systems can be chosen to ensure that the correct modification, processing and sub-cellular localization of the SM38 protein occurs. To this end, host cells which possess the ability to properly modify and process the SM38 protein are preferred. For long-term, high yield production of recombinant SM38 protein, such as that desired for development of cell lines for screening purposes, stable expression is preferred. Rather than using expression vectors which contain origins of replication, host cells can be transformed with DNA controlled by appropriate expression control elements and a selectable marker gene, i.e., tk, hgprt, dhfr, neo, and hygro gene, to name a few. Following the introduction of the foreign DNA, engineered cells may be allowed to grow for 1-2 days in enriched media, and then switched to a selective media. Such engineered cell lines may be particularly useful in screening and evaluation of compounds that modulate the endogenous activity of the SM38 gene product.

5.1.3 Transgenic Animals

The SM38 gene products can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate SM38 transgenic animals.

Any technique known in the art may be used to introduce the SM38 transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, *Proc. Natl. Acad. Sci. USA* 82:6148-6152); gene targeting in embryonic stem cells (Thompson et al., 1989, *Cell*, 56:313-321); electroporation of embryos (Lo, 1983, *Mol. Cell. Biol.* 3:1803-1814); and sperm-mediated gene transfer (Lavitrano et al., 1989, *Cell* 57:717-723); etc. For a review of such techniques, see Gordon, 1989, *Transgenic Animals, Intl. Rev. Cytol.* 115:171-229, which is incorporated by reference herein in its entirety.

The present invention provides for transgenic animals that carry the SM38 transgene in all their cells, as well as animals which carry the transgene in some, but not all their cells, i.e., mosaic animals. The transgene may also be selectively introduced into and activated in a particular cell type by following, for example, the teaching of Lasko et al., (Lasko, M. et al., 1992, *Proc. Natl. Acad. Sci. USA* 89:6232-6236). The regulatory sequences required for such a cell-type specific activation will depend upon the particular cell type of interest, and will be apparent to those of skill in the art. When it is desired that the SM38 transgene be integrated into the chromosomal site of the endogenous SM38 gene, gene targeting is preferred. Briefly, when such a technique is to be utilized, vectors containing some nucleotide sequences homologous to the endogenous SM38 gene are designed for the purpose of integrating, via homologous recombination with chromosomal sequences, into and disrupting the function of the nucleotide sequence of the endogenous SM38 gene.

Once transgenic animals have been generated, the expression of the recombinant SM38 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of SM38 gene-expressing tissue may also be evaluated immunocytochemically using antibodies specific for the SM38 transgene product.

5.1.4. Antibodies to SM38 Proteins

Antibodies that specifically recognize one or more epitopes of SM38, or epitopes of conserved variants of SM38, or peptide fragments of SM38 are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in conjunction with compound screening schemes, as described, below, for the evaluation of the effect of test compounds on expression and/or activity of the SM38 gene product.

For production of antibodies, various host animals maybe immunized by injection with a SM38 protein, or SM38 peptide. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (Bacille Calmette-Guerin) and *Corynebacterium parvum*.

Polyclonal antibodies comprising heterogeneous populations of antibody molecules, may be derived from the sera of the immunized animals. Monoclonal antibodies may be obtained by any technique which provides for the production of antibody molecules by continuous cell lines in culture. These include, but are not limited to, the hybridoma technique of Kohler and Milstein, (1975, *Nature* 256:495-497; and U.S. Pat. No. 4,376,110), the human B-cell hybridoma technique (Kosbor et al., 1983, *Immunology Today* 4:72; Cole et al., 1983, *Proc. Natl. Acad. Sci. USA* 80:2026-2030), and the EBV-hybridoma technique (Cole et al., 1985, *Monoclonal Antibodies And Cancer Therapy*, Alan R. Liss, Inc., pp. 77-96). Such antibodies may be of any immunoglobulin class including IgG, IgM, IgE, IgA, IgD and any subclasses thereof. The hybridoma producing the mAb of this invention may be cultivated in vitro or in vivo. Production of high titres of Mabs in vivo makes this the presently preferred method of production.

In addition, techniques developed for the production of "chimeric antibodies" by splicing the genes from a mouse antibody molecule of appropriate antigen specificity together with genes from a human antibody molecule of appropriate biological activity can be used (Morrison et al., 1984, *Proc Nat'l. Acad. Sci.*, 81:6851-6855; Neuberger et al., 1984, *Nature*, 312: 604-608; Takeda et al. 1985, *Nature* 314: 452-454), Alternatively, techniques developed for the production of humanized antibodies (U.S. Pat. No. 5,585,089) or single chain antibodies (U.S. Pat. No. 4,946,778 Bird, 1988, *Science* 242: 423-426; Huston et al., 1988, *Proc. Nat'l. Acad. Sci. USA*, 85: 5879-5883; and Ward et al., 1989, *Nature* 334: 544-546) may be used to produce antibodies that specifically recognize one or more epitopes of SM38.

5.2. Screening Assays for Compounds Useful in Modulating the Activity of CD38/SM38

The present invention relates to screening assay systems designed to identify compounds or compositions that modulate CD38/SM38 enzyme activity, cADPR mediated signal transduction, or CD38/SM38 gene expression, or that cleave SM38 from a cell membrane, and thus, may be useful for modulation of cell migration or treatment of infection. As used herein, "CD38/SM38" specifies CD38 and/or SM38.

5.2.1. Recombinant Expression of CD38

For purposes of developing screening assays designed to identify compounds or compositions that modulate CD38/

SM38 activity it may be necessary to recombinantly express the CD38/SM38 proteins. The cDNA sequence and deduced amino acid sequence of CD38 has been characterized from several species including human, marine and rat as described in Jackson, D. G. et al., 1990, *J. Immunol.* 151:3111-3118; Koguma, T. et al., 1994, *Biochim Biophys Acta* 1224:160-162 and Harada N et al., 1993, *J Immunol* 151:3111-3118, incorporated herein by reference. In addition, the cDNA and deduced amino acid sequence of *Shistosoma mansoni*, as described herein may be utilized to recombinantly express the CD 38 homologue, SM38, protein.

CD38/SM38 nucleotide sequences may be isolated using a variety of different methods known to those skilled in the art. For example, a cDNA library constructed using RNA from a tissue known to express CD38/SM38 can be screened using a labeled CD38/SM38 probe. Alternatively, a genomic library may be screened to derive nucleic acid molecules encoding the CD38/SM38 protein. Further, CD38/SM38 nucleic acid sequences may be derived by performing a polymerase chain reaction (PCR) using two oligonucleotide primers designed on the basis of known CD38/SM38 nucleotide sequences. The template for the reaction may be cDNA obtained by reverse transcription of mRNA prepared from cell lines or tissue known to express CD38/SM38.

CD38/SM38 protein, polypeptides and peptide fragments, mutated, truncated or deleted forms of CD38/SM38 and/or CD38/SM38 fusion proteins can be prepared for a variety of uses, including but not limited to the generation of antibodies, the identification of other cellular gene products involved in the regulation of CD38/SM38 mediated cell migration, and the screening for compounds that can be used to modulate cell migration. CD38/SM38 fusion proteins include fusions to an enzyme, fluorescent protein, a polypeptide tag or luminescent protein which provide a marker function.

While the CD38/SM38 polypeptides and peptides can be chemically synthesized (e.g., see Creighton, 1983, Proteins: Structures and Molecular Principles, W.H. Freeman & Co., N.Y.), large polypeptides derived from CD38/SM38 and the full length CD38/SM38 itself may be advantageously produced by recombinant DNA technology using techniques well known in the art for expressing a nucleic acid containing CD38/SM38 gene sequences and/or coding sequences. Such methods can be used to construct expression vectors containing the CD38/SM38 nucleotide sequences and appropriate transcriptional and translational control signals. These methods include, for example, in vitro recombinant DNA techniques, synthetic techniques, and in vivo genetic recombination. (See, for example, the techniques described in Sambrook et al., 1989, supra, and Ausubel et al., 1989, supra).

A variety of host-expression vector systems maybe utilized to express the CD38/SM38 nucleotide sequences. Where the CD38/SM38 peptide or polypeptide is expressed as a soluble protein or derivative (e.g., peptides corresponding to the intracellular or extracellular domain) and is not secreted, the peptide or polypeptide can be recovered from the host cell. Alternatively, where the CD38 peptide or polypeptide is secreted the peptide or polypeptides maybe recovered from the culture media. However, the expression systems also include engineered host cells that express CD38/SM38 or functional equivalents, anchored in the cell membrane. Purification or enrichment of the CD38/SM38 from such expression systems can be accomplished using appropriate detergents and lipid micelles and methods well known to those skilled in the art. Such engineered host cells themselves may be used in situations where it is important not only to retain the structural and functional characteristics of the CD38/SM38, but to assess biological activity, i.e., in drug screening assays.

The expression systems that may be used for purposes of the invention include but are not limited to microorganisms such as bacteria transformed with recombinant bacteriophage, plasmid or cosmid DNA expression vectors containing CD38/SM38 nucleotide sequences; yeast transformed with recombinant yeast expression vectors containing CD38/SM38 nucleotide sequences or mammalian, helminth or insect cell systems harboring recombinant expression constructs containing promoters derived from the genome of mammalian, helminth or insect cells or from mammalian or insect viruses.

Appropriate expression systems can be chosen to ensure that the correct modification, processing and sub-cellular localization of the CD38/SM38 protein occurs. To this end, eukaryotic host cells which possess the ability to properly modify and process the CD38/SM38 protein are preferred. For long-term, high yield production of recombinant CD38/SM38 protein, such as that desired for development of cell lines for screening purposes, stable expression is preferred. Rather than using expression vectors which contain origins of replication, host cells can be transformed with DNA controlled by appropriate expression control elements and a selectable marker gene, i.e., tk, hgprt, dhfr, neo, and hygro gene, to name a few. Following the introduction of the foreign DNA, engineered cells may be allowed to grow for 1-2 days in enriched media, and then switched to a selective media. Such engineered cell lines may be particularly useful in screening and evaluation of compounds that modulate the endogenous activity of the CD38/SM38 gene products.

5.2.2. Non-Cell Based Assays

In accordance with the invention, non-cell based assay systems may be used to identify compounds that interact with, i.e., bind to CD38, and regulate the enzymatic activity of CD38. Such compounds may act as antagonists or agonists of CD38 enzyme activity and maybe used to regulate cell migration including but not limited to hematopoietically derived cells. Additionally, such compounds may be used to regulate the growth, muscle contractility, differentiation, maturation and reproduction of pathogenic micro-organisms expressing SM38 or structurally related homologues. Recombinant CD38/SM38, including peptides corresponding to different functional domains or CD38/SM38 fusion proteins may be expressed and used in assays to identify compounds that interact with CD38/SM38.

To this end, soluble CD38/SM38 maybe recombinantly expressed and utilized in non-cell based assays to identify compounds that bind to CD38/SM38. Recombinantly expressed CD38/SM38 polypeptides or fusion proteins containing one or more of the CD38/SM38 functional domains may be prepared as described above, and used in the non-cell based screening assays. For example, the full length CD38/SM38, or a soluble truncated CD38/SM38, e.g., in which the one or more of the cytoplasmic and transmembrane domains is deleted from the molecule, a peptide corresponding to the extracellular domain, or a fusion protein containing the CD38/SM38 extracellular domain fused to a protein or polypeptide that affords advantages in the assay system (e.g., labeling, isolation of the resulting complex, etc.) can be utilized. Where compounds that interact with the cytoplasmic domain are sought to be identified, peptides corresponding to the CD38 cytoplasmic domain and fusion proteins containing the CD38 cytoplasmic domain can be used.

The CD38/SM38 protein may also be one which has been fully or partially isolated from cell membranes or from the cytosol of cells, or which may be present as part of a crude or semi-purified extract. As a non-limiting example, the CD38 protein may be present in a preparation of cell membranes and the SM38 protein may be present in a preparation of cell cytosol. In particular embodiments of the invention, such cell membranes may be prepared using methods known to those of skill in the art.

The principle of the assays used to identify compounds that bind to CD38/SM38 involves preparing a reaction mixture of the CD38/SM38 and the test compound under conditions and for time sufficient to allow the two components to interact and bind, thus forming a complex which can be removed and/or detected in the reaction mixture. The identity of the bound test compound is then determined.

The screening assays are accomplished by any of a variety of commonly known methods. For example, one method to conduct such an assay involves anchoring the CD38/SM38 protein, polypeptide, peptide, fusion protein or the test substance onto a solid phase and detecting CD38/test compound or SM38/test compound complexes anchored on the solid phase at the end of the reaction. In one embodiment of such a method, the CD38/SM38 reactant is anchored onto a solid surface, and the test compound, which is not anchored, may be labeled, either directly or indirectly.

In practice, microtitre plates conveniently can be utilized as the solid phase. The anchored component is immobilized by non-covalent or covalent attachments. The surfaces may be prepared in advance and stored. In order to conduct the assay, the non-immobilized component is added to the coated surfaces containing the anchored component. After the reaction is completed, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the solid surface; e.g., using a labeled antibody specific for the previously non-immobilized component.

Alternatively, a reaction is conducted in a liquid phase, the reaction products separated from unreacted components using an immobilized antibody specific for CD38/SM38 protein, fusion protein or the test compound, and complexes detected using a labeled antibody specific for the other component of the possible complex to detect anchored complexes.

In accordance with the invention, non-cell based assays may also be used to screen for compounds that directly inhibit or activate enzymatic activities associated with CD38/SM38. Such activities include but are not limited to ADP-ribosyl cyclase activity, transglycosidation activity, and NAD+glycohydrolase activity. To this end, a reaction mixture of CD38/SM38 and a test compound is prepared in the presence of substrate and the enzymatic activity of CD38/SM38 is compared to the activity observed in the absence of test compound. Substrates that may be used in the assays for detection of CD38/SM38 enzyme activity include but are not limited to NAD+ and NADP and labeled forms thereof. Additionally, derivatives of NAD such as Nicotinamide guanine dinucleotide (NGD) and Nicotinamide 1, $N^6$-etheno-adenine dinucleotide (1,$N^6$ etheno-NAD) may be used.

In non-limiting embodiments of the invention, a reaction mixture of CD38/SM38, a test compound and substrate is prepared and the activity of CD38/SM38 is compared to the activity observed in the absence of the test compound wherein decrease in the level of CD38/SM38 enzyme activity in the presence of the test compound indicates that a CD38/SM38 antagonist has been identified. Alternatively, a reaction mixture of CD38/SM38, a test compound and substrate is prepared and the activity of CD38/SM38 is compared to the activity observed in the absence of the test compound wherein an increase in the level of CD38/SM38 enzyme activity in the presence of the test compound indicates that a CD38/SM38 agonist has been identified.

The enzymatic activity of CD38/SM38 may be detected in a variety of different ways. For example, levels of cyclic adenosine diphosphate ribose (cADPR) adenosine diphosphate ribose (ADPR) and/or nicotinic acid adenine dinucleotide phosphate (NAADP) can be measured using high performance liquid chromatography (HPLC) or thin layer chromatography (TLC) (Aarhus R et al., 1995, J. Biochem. Chem. 270:30327-30333; Muller-Steffner H M, J. Biol. Chem. 271:23967-23972; and Lund F E et al., 1999, *J. Immunology* 162:2693-2702; Higashida, H. et al., 1997, *J. Biol. Chem.* 272:3127-3177) in conjunction with the use of radio-labeled substrates such as NAD or NADP or NA. Additionally, radioimmunoassays (Takahashi K et al., 1995, *FEBS Lett* 371:204-208; Vu C Q et al., 1997, *Biochem Biophys Res Commun* 236:723-726; Vu et al., *Adv Exp Med Biol* 419:381-388; and Graeff R M et al., 1997, *Methods Enzymol* 280:230-241), bioassays (Aarhus R et al., 1995, *J Biol. Chem.* 270: 30327-30333; Clapper D L et al., *J. Biol. Chem.* 262:9561-9568; and-Lee et al., *J. Biol. Chem.* 264:1608-1615) and/or fluorescent assays (Graeff R M et al., 1996, *Biochem.* 35:379-386; Graeff et al., 1994, *J. Biol. Chem.* 269:30260-30267; and Gadangi P et al., 1996, *J. Immunol.* 156:1937-1941) may be used for measuring cADPR, ADPR or NAADP levels. In yet another embodiment of the invention, derivatives of NAD such as NGD (Nicotinamide guanine dinucleotide) and Nicotinamide 1, $N^6$-etheno-adenine dinucleotide (1,$N^6$ etheno-NAD) may be used to measure CD38/SM38 enzyme activity. When the 1,$N^6$ etheno-NAD is hydrolysed by CD38, one of the resulting products will fluoresce (Muller et al., 1983, *Biochem. J.* 212:459-464; and Cockayne D et al., 1998, *Blood* 92:1324-1333). When the analog NGD is cyclized through the ADP-ribosyl activity of CD38/SM38 the product forms a fluorescent compound that can be detected by fluorimeter (Graeff et al., 1996, *Biochem* 35:379-386; and Graeff et al., 1994, *J. Biol. Chem.* 269:30260-30267).

In another embodiment of the invention, computer modeling and searching technologies will permit identification of potential modulators of CD38/SM38 enzyme activity. For example, based on the knowledge of the *Aplysia* cyclase active site (Munshi C. et al., 199, J. Biol. Chem. 274: 30770-30777) and the CD38 active site (Lund F E et al., 1999, *J. Immunology* 162:2693-2702; Munshi, C et al., 2000, *J. Biol. Chem.* 275:21566-21571; Graeff R et al., 2001, *J. Biol. Chem.* 276:12169-12173) and the study of complexes between CD38/SM38 substrates and substrate anologs, potential modulators of CD38/SM38 activity may be identified.

The three dimensional geometric structure of the active site may be determined using known methods, including x-ray crystallography, which can determine a complete molecular structure (see, for example, Prasad G S et al., *Nature Struc. Biol.* 3:957-964 which describes the crystal structure of *Aplysia* ADP ribosyl cyclase). On the other hand, solid or liquid phase NMR can be used to determine certain intramolecular distances. Any other experimental method of structure determination can be used to obtain the partial or complete geometric structure of the CD38 active site.

Having determined the structure of the CD38/SM38 active site, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential CD38 modulating compounds.

Alternatively, these methods can be used to identify improved modulating compounds from an already known modulating compounds. For example, a number of compounds that modulate the enzyme activity of other enzymes that utilize NADI/NADP as substrates (i.e., PARP family homologues) have already been identified. The composition of the known compound can be modified and the structural effects of modification can be determined using experimental and computer modeling methods applied to the new composition. The altered structure is then compared to the active site structure of the compound to determine if an improved fit or interaction results. In this manner systematic variations in composition, such as by varying side groups, can be quickly evaluated to obtain modified modulating compounds or substrates of improved specificity or activity.

5.2.3. Cell Based Assays

In accordance with the invention, a cell based assay system can be used to screen for compounds that modulate the activity of CD38/SM38. In accordance with the invention, a cell-based assay system can be used to screen for compounds that modulate the activity of CD38 and thereby, modulate the chemoattractant induced $Ca^{2+}$ influx and the migration of cells. Additionally, this cell based system can be used to screen for compounds that modulate the activity of SM38, and thereby, modulate intracellular calcium release and/or muscle contractility in cells. To this end, cells that endogenously express CD38/SM38 can be used to screen for compounds. Such cells include, for example, neutrophils, lymphocytes, eosinophils, macrophages and dendritic cells. In addition, S. mansoni cells that express SM38, may be used to screen for compounds. Alternatively, cell lines, such as 293 cells, COS cells, CHO cells, fibroblasts, and the like, genetically engineered to express CD38/SM38 can be used for screening purposes. For screens utilizing host cells genetically engineered to express a functional CD38 protein, it would be preferred to use host cells that are capable of responding to chemoattractants or inflammatory stimuli. For screens utilizing host cells genetically engineered to express SM38, it would be preferable to use cells of S mansoni origin that are capable of responding to a variety of stimuli such as acetylcholine or high concentrations of K+ to induce muscle contraction. Further, ooyctes or liposomes engineered to express the CD38/SM38 protein may be used in assays developed to identify modulators of CD38/SM38 activity.

The present invention provides methods for identifying compounds that alter one of more of the enzymatic activities of CD38/SM38, including but not limited to, NAD glycohydrolase activity, ADP-ribosyl cyclase activity and/or transglycosidation (exchange) activity. Specifically, compounds may be identified that promote CD38/SM38 enzyme activities, i.e., agonists, or compounds that inhibit CD38/SM38 enzyme activities, i.e., antagonists. Compounds that inhibit CD38 enzyme activities will be inhibitory for chemoattractant induced calcium responses and cell migration (FIG. 2).

Compounds that activate CD38 enzyme activity will enhance chemoattractant induced calcium responses and cell migration. Compounds that either activate or inhibit SM38 enzyme activities will alter the viability or functional activities of pathogenic organisms expressing SM38. Such compounds maybe compounds that interact with the active site of CD38/SM38 thereby modulating enzyme activity, or compounds that compete/facilitate substrate binding to CD38/SM38 or compete/inhibit catalysis of substrate (FIG. 2). Alternatively, compounds may be identified that modulate the activity of proteins that modify the CD38/SM38 protein, i.e., phosphorylate, ribosylate, etc., and thereby regulate the activity of CD38 (FIG. 3). Such proteins include for example, ADP-ribosyl transferases which ribosylate CD38/SM38 and render CD38/SM38 enzymatically inactive. In addition, compounds may be identified that regulate CD38/SM38 expression and thereby regulate the level of enzyme activity within a cell (FIG. 4).

The present invention provides for methods for identifying a compound that activates CD38/SM38 enzyme activity comprising (i) contacting a cell expressing CD38/SM38 and chemoattractant receptors with a test compound in the presence of substrate and measuring the level of CD38/SM38 activity; (ii) in a separate experiment, contacting a cell expressing CD38/SM38 protein and chemoattractant receptors with a vehicle control in the presence of substrate and measuring the level of CD38/SM38 activity where the conditions are essentially the same as in part (i), and then (iii) comparing the level of CD38/SM38 activity measured in part (i) with the level of CD38/SM38 activity in part (ii), wherein an increased level of CD38/SM38 activity in the presence of the test compound indicates that the test compound is a CD38/SM38 activator.

The present invention also provides for methods for identifying a compound that inhibits CD38/SM38 enzyme activity comprising (i) contacting a cell expressing CD38/SM38 and chemoattractant receptors with a test compound in the presence of a chemoattractant and substrate and measuring the level of CD38/SM38 activity; (ii) in a separate experiment, contacting a cell expressing CD38/SM38 and chemoattractant receptors with a chemoattractant and substrate and measuring the level of CD38/SM38 activity, where the conditions are essentially the same as in part (i) and then (iii) comparing the level of CD38/SM38 activity measured in part (i) with the level of CD38/SM38 activity in part (ii), wherein a decrease level of CD38/SM38 activity in the presence of the test compound indicates that the test compound is a CD38/SM38 inhibitor.

Depending on the assays used to detect CD38/SM38 activity, the methods described above for identifying activators and inhibitors of CD38/SM38 may include the presence or absence of a chemoattractant in steps (i) and (ii). For example, when assaying directly for CD38/SM38 ADP-ribosyl cyclase activity or the production of CD38/SM38 metabolites, the presence of a chemoattractant or the expression of a chemoattractant receptor on the test cell may not be required. However, in instances where, for example, chemotaxis or changes in intracellular calcium levels are measured in CD-38-expressing cells it may be necessary to include chemoattractants. Alternatively, when muscle contractility or changes in intracellular calcium levels are measured in SM38-expressing cells, it may be necessary to include stimulants to activate muscle contraction and/or calcium release including, but not limited to, acetylcholine, serotonin (Day et al., 1994, Paristol. 108:425-432), FMRF-amide related peptides (FaRPs) (Day et al., 1994, Paristol. 109:455-459) or high K+ concentrations in the media (Day et al., 1993, Paristol. 106:471-477). Additionally, it will be necessary to perform these experiments with host cells that express the receptors specific for the stimulants utilized. Those skilled in the art will be able to determine operative and optimal assay conditions by employing routine experimentation.

A "chemoattractant", as defined herein, is a compound or molecular complex that induces the migration of cells via a mechanism that is dependent on the production of cADPR by CD38. An example of such a chemoattractant includes, but is not limited to, fMet-leu-Phe (fMLP). Other chemoattractants that may be used include, eotaxin, GRO-1, IP-10, SDF-1, BLC, Rantes, MIP-1A, MCP-3, MIP3a, IL-8, CLS, ELC, Lymphotactin, PAF, Ltb4, complement c5a and histamine.

In utilizing the cell systems described above, such cell systems, the cells expressing the CD38/SM38 protein are exposed to a test compound or to vehicle controls e.g., placebos): After exposure, the cells can be assayed to measure the activity of CD38/SM38 or the activity of the CD38 dependent signal transduction pathway itself can be assayed.

The ability of a test molecule to modulate the activity of CD38/SM38 maybe measured using standard biochemical and physiological techniques. Responses such as activation or suppression of CD38/SM38 ADP-ribosyl cyclase activity or the production of CD38/SM38 metabolites such as cADPR and/or NAADP can be measured. Levels of cADPR, ADPR and/or NAADP can be measured using HPLC or TLC in conjunction with the use of radio-labeled substrates such as NAD or NADP or NA. Additionally, radioimmunoassays, bioassays and/or fluorescent assays, such as those discussed in Section 5.1.1, supra, may be used for measuring cADPR or NAADP levels. In yet another embodiment of the invention, derivatives of NAD such as NGD (Nicotinamide guanine dinucleotide) and Nicotinamide 1, $N^6$-etheno-adenine dinucleotide (1,$N^6$ etheno-NAD) may be used to measure CD38/SM38 activity.

Test compounds may also be assayed utilizing cell based calcium and/or migration assays to identify compounds that are capable of inhibiting or activating chemoattractant induced CD38 dependent calcium responses and cell migration. In non-limiting embodiments of the invention, changes in intracellular $Ca^{2+}$ levels may be monitored by the fluorescence of $Ca^{2+}$ indicator dyes such as Indo, Fluo-3 and Fura-Red, etc. Further, changes in membrane potential resulting from modulation of the CD38/SM38 enzyme activity can be measured using a voltage clamp or patch recording methods. Directed migration of cells may also be monitored by standard chemotaxis assays in modified Boyden chambers or on slides. Such assay systems are described in further detail in the working example of the present specification (See, Example 6). Muscle contractility may also be measured by standard assays described in detail in the literature (for example: (Day et al., 1994 *Parasitology* 109:455-9) and references therein).

After exposure to the test compound, or in the presence of a test compound, cells can be stimulated with a chemoattractant such as fMLP or a muscle activator or constrictor, such as high K+ concentrations, acetylcholine, endothelin, etc., and changes in intracellular calcium levels, cADPR or NAADP levels, muscle, contractility and/or cell migration may be measured. These measurements will be compared to cells treated with the vehicle control. Increased levels of intracellular $Ca^{2+}$, increased production of cADPR, increases in muscle contractility and/or increased migration of cells toward a chemoattractant in the presence of a test compound indicates that the compound acts as an agonists to increase the Ca2+ response increase muscle contractility and increase chemoattractant induced CD38 dependent cell migration.

Decreased levels of intracellular Ca2+, decreased production of cADPR, decreased muscle contractility and/or decreased migration of cells toward a chemoattractant in the presence of a test compound indicates that the compound acts as an antagonist and inhibits the Ca2+ response, decreases muscle contractility and inhibits chemoattractant induced CD38 dependent cell migration (see, for example, FIGS. 2 and 3).

In addition, the assays of the invention may be used to identify compounds that (i) function as substrates of CD38/SM38 enzymatic activity and are converted into agonists or antagonists of cADPR dependent Ca2+ signal transduction pathway (FIG. 5). A compound fitting these specifications is described in further detail in the working example of the present specification (Example 6, FIG. 11). Alternatively, the assays of the invention may be used (ii) to identify compounds that specifically interfere with the cADPR mediated Ca2+ signal transduction pathways (FIG. 6). In a non-limiting embodiment of the invention, test compounds may include chemical derivatives of any known and unknown substrates of CD38/SM38 (for example, the substrate analog 8-Br-βNAD is converted into the modified product 8-Br-cADPR which acts as an antagonist of cADPR mediated Ca2+ signal transduction). The test substrate may be administered to cells expressing CD38/SM38 and the appropriate chemoattractant receptors in the presence of the chemoattractant or muscle stimulant. Conversion of the modified test substrate into a modified product that is capable of modulating the activity of cADPR can be measured utilizing the methods described above. Test substrates may also be assayed to determine their effect on calcium influx, muscle contractility and/or cell migration. Intracellular Ca2+ accumulation and directed migration to a chemoattractant can be measured in cells treated with the test substrate and the chemoattractant and compared to cells receiving the non-modified substrate. i.e., NAD and a chemoattractant. Compounds which are converted into modified products, i.e., 8-Br-cADPR, and competitively or non-competitively inhibit cADPR induced calcium responses, muscle contractility or directed migration will be identified as antagonists of the cADPR $Ca^{2+}$ signaling pathway, while compounds that are converted into modified products that are competitive or non-competitive agonists of the cADPR $Ca^{2+}$ signaling pathway will be defined as agonists or activators.

In yet another embodiment of the invention, compounds that directly alter (i.e., activate or inactivate) the activity of cADPR, i.e., induced calcium release and cell migration, can be tested in assays. Such agonists or antagonists would be expected to modulate the influx of Ca2+ into the cell resulting in changes in the cell's migratory activity or ability to contract. Antagonists would have reduced Ca2+ responses, reduced contractility and/or reduced migration in the presence of a chemoattractant. Examples of antagonists include, but are not limited to 8-NH$_2$-cADPR, 8-Br-cADPR, 8-CH$_3$-cADPR, 8-OCH3-cADPR and 7-Deaza-8-Br-cADPR. A compound fitting these specifications is described in further detail in the working example of the present specification (Example 6, FIG. 10). Agonists would have increased Ca2+ responses, increased contractility and/or increased migration in the presence of chemoattractants. Examples of agonists include but are not limited to 2'-deoxy-cADPR, 3'-deoxy-cADPR and 2'-phospho-cADPR. Assays for direct measurement of cAPDR activity include the bioassays such as those described by Howard et al. (1995, Science 262:1056); Galione et al. (1993, Nature 365:456-459) and Lee and Aarhus (1991, Cell Regulation 2:203-209).

Further, the assays of invention may identify compounds that are capable of activating CD38/SM38 enzyme activity, i.e., agonists, but which desensitize the calcium pathway by depletion of intracellular calcium stores. Such desensitization may, in some instances, lead to inhibition of cell migration or muscle contraction due to the depletion of calcium stores. Thus compounds may be identified that function as agonists in CD38/SM38 enzyme assays but function as antagonists in chemotaxis or muscle contraction assays. Such assays and compounds are within the scope of the present invention.

5.2.4. Assay for Compounds that Regulate the Expression of CD38/SM38

In accordance with the invention, a cell based assay system can be used to screen for compounds that modulate the expression of CD38/SM38 within a cell. Data described herein indicates that expression of SM38 is developmentally regulated in *S. mansoni*. In particular, SM38 is expressed during worm pairing and such expression is maintained in the adult worms. Such an expression pattern provides a target for compounds that modulate SM38 expression. Assays may be designed to screen for compounds that regulate CD38/SM38 expression at either the transcriptional or translational level. In one embodiment, DNA encoding a reporter molecule can be linked to a regulatory element of the CD38/SM38 gene and used in appropriate intact cells, cell extracts or lysates to identify compounds that modulate CD38/SM38 gene expression. Such reporter genes may include but are not limited to chloramphenicol acetyltransferase (CAT), luciferase, β-glucuronidase (GUS), growth hormone, or placental alkaline phosphatase (SEAP). Such constructs are introduced into cells thereby providing a recombinant cell useful for screening assays designed to identify modulators of CD38/SM38 gene expression.

Following exposure of the cells to the test compound; the level of reporter gene expression may be quantitated to determine the test compound's ability to regulate CD38/SM38 expression. Alkaline phosphatase-assays are particularly useful in the practice of the invention as the enzyme is secreted from the cell. Therefore, tissue culture supernatant may be assayed for secreted alkaline phosphatase. In addition, alkaline phosphatase activity may be measured by calorimetric, bioluminescent or chemiluminescent assays such as those described in Bronstein, I. et al. (1994, *Biotechniques* 17: 172-177). Such assays provide a simple, sensitive easily automatable detection system for pharmaceutical screening.

To identify compounds that regulate CD38/SM38 translation, cells or in vitro cell lysates containing CD38/SM38 transcripts maybe tested for modulation of CD38/SM38 mRNA translation. To assay for inhibitors of CD38/SM38 translation, test compounds are assayed for their ability to modulate the translation of CD38/SM38 mRNA in in vitro translation extracts.

In an embodiment of the invention, the level of CD38/SM38 expression can be modulated using antisense, ribozyme, or RNAi approaches to inhibit or prevent translation of CD38/SM38 mRNA transcripts or triple helix approaches to inhibit transcription of the CD38/SM38 gene. Such approaches may be utilized to treat disorders such as inflammation and allergies where inhibition of CD38/SM38 expression is designed to prevent hematopoietically-derived cell migration or inhibition of SM38 is designed to alter *S. mansoni* physiology and pathogenesis.

Antisense and RNAi approaches involve the design of oligonucleotides (either DNA or RNA) that are complementary to CD38/SM38 mRNA. The antisense or RNAi oligonucleotides will be targeted to the complementary mRNA transcripts and prevent translation. Absolute complementarity, although preferred, is not required. One skilled in the art can ascertain a tolerable degree of mismatch by use of standard procedures to determine the melting point of the hybridized complex.

In yet another embodiment of the invention, ribozyme molecules designed to catalytically cleave CD38/SM38 mRNA transcripts can also be used to prevent translation of CD38/SM38 mRNA and expression of CD38/SM38. (See, e.g., PCT International Publication WO90/11364, published Oct. 4, 1990; Sarver et al., 1990, Science 247:1222-1225). Alternatively, endogenous CD38/SM38 gene expression can be reduced by targeting deoxyribonucleotide sequences complementary to the regulatory region of the CD38/SM38 gene (i.e., the CD38 promoter and or enhancers) to form triple helical structures that prevent transcription of the CD38/SM38 gene in targeted hematopoietically-derived cells in the body. (See generally, Helene, C. et al., 1991, Anticancer Drug Des. 6:569-584 and Maher, L J, 1992, Bioassays 14:807-815).

The oligonucleotides of the invention, i.e., antisense, ribozyme and triple helix forming oligonucleotides, may be synthesized by standard methods known in the art, e.g., by use of an automated DNA synthesizer (such as are commercially available from Biosearch, Applied Biosystems, etc.). Alternatively, recombinant expression vectors may be constructed to direct the expression of the oligonucleotides of the invention. Such vectors can be constructed by recombinant DNA technology methods standard in the art. In a specific embodiment, vectors such as viral vectors may be designed for gene therapy applications where the goal is in vivo expression of inhibitory oligonucleotides in targeted cells.

5.2.5. Assay for Compounds that Cleave the GPI-Anchored SM38 Protein

Data described herein (see Example 9) indicate that SM38 is expressed as a GPI-anchored protein on the outer tegument of adult *S. mansoni* worms. Thus, compounds having the ability to cleave SM38 from the outer tegument, or membrane, of *S. mansoni* may be particularly useful in the treatment of schistosomiasis. Assays may be designed to screen for compounds that cleave the SM38 protein from the membrane, and such assays are encompassed by the present invention. In one embodiment, a cell-based assay is used to detect compounds that cleave the SM38 protein from the membrane. By way of non-limiting example, cells expressing SM38 may be incubated in a supernatant containing a test compound for a sufficient period of time for the test compound to cleave the membrane-bound SM38. The supernatant can then be removed. The presence of SM38 in the supernatant can be detected in a number of ways, including but not limited to immunoassays, and would indicate that the test compound has the ability to cleave SM38 from the cell membrane. In a second embodiment, cells expressing SM38 are anchored to a solid surface, and a test compound is applied for a sufficient period of time for the test compound to cleave the membrane-bound SM38. The test compound is then removed, such as by washing. The presence of membrane-bound SM38 may then be detected in a variety of ways, indicating a test compound's inability to cleave SM38 from the cell membrane. SM38 may be detected by such means as contacting an antibody that recognizes SM38 to the anchored cells. The antibody may be labeled for easy detection.

5.2.6. Compounds that can be Screened in Accordance with the Invention

The assays described above can identify compounds which modulate CD38/SM38 activity. For example, compounds that affect CD38/SM38 activity include but are not limited to compounds that bind to CD38/SM38, and either activate enzyme activities (agonists) or block enzyme activities (antagonists). Alternatively, compounds may be identified that do not bind directly to CD38/SM38 but are capable of altering CD38/SM38 enzyme activity by altering the activity of a protein that regulates CD38/SM38 enzyme activity (see, FIG. 3) Compounds that are substrates of CD38/SM38 that are converted into modified products that activate or inhibit the cADPR Ca2+ signal transduction pathway, the ADPR Ca2+ signaling pathway, or the NAADP signaling pathway can also be identified by the screens of the invention. Compounds that directly activate or inhibit the cADPR Ca2+ signal transduction pathway in cells can also be identified. Additionally, compounds that activate CD38/SM38 enzyme activity resulting in desensitization of the calcium pathway maybe identified. Such desensitizing compounds would be expected to inhibit cell migration. Further, compounds that affect CD38/SM38 gene activity (by affecting CD38/SM38 gene expression, including molecules, e.g., proteins or small organic molecules, that affect transcription or interfere with splicing events so that expression of the full length or the truncated form of the CD38/SM38 can be modulated) can be identified using the screens of the invention.

The compounds which may be screened in accordance with the invention include, but are not limited to, small organic or inorganic compounds, peptides, antibodies and fragments thereof, and other organic compounds e.g., peptidomimetics) that bind to CD38/SM38 and either mimic the activity triggered by any of the known or unknown substrates of CD38/SM38 (i.e., agonists) or inhibit the activity triggered by any of the known or unknown substrates of CD38/SM38 (i.e., antagonists). Compounds that bind to CD38/SM38 and either enhance CD38/SM38 enzyme activities (i.e., ADP-ribosyl cyclase activity, NAD glycohydrolase activity, transglycosidation activity), i.e., agonists, or compounds that inhibit CD38/SM38 enzyme activities, i.e., antagonists, in the presence or absence of the chemoattractant or muscle stimulant will be identified. Compounds that bind to proteins that alter/modulate the enzyme activity of CD38/SM38 will be identified. Compounds that mimic natural substrates, i.e., NAD(P) and are converted by CD38/SM38 enzyme activities into products that act as agonists or antagonists of the cADPR induced calcium release pathway can be identified. Compounds that directly activate or inhibit the cADPR Ca2+ signal transduction pathway in cells can be identified.

Compounds may include, but are not limited to, peptides such as, for example, soluble peptides, including but not limited to members of random peptide libraries (see, e.g., Lam, K. S. et al., 1991, Nature 354:82-84; Houghten, R. et al., 1991, Nature 354:84-86); and combinatorial chemistry-derived molecular library made of D- and/or L-configuration amino acids, phosphopeptides (including, but not limited to, members of random or partially degenerate, directed phosphopeptide libraries; (see, e.g., Songyang, Z. et al., 1993, Cell 72:767-778), antibodies (including, but not limited to, polyclonal, monoclonal, humanized, anti-idiotypic, chimeric or single chain antibodies, and FAb, F(ab')$_2$ and FAb expression library fragments, and epitope binding fragments thereof), and small organic or inorganic molecules.

Other compounds which maybe screened in accordance with the invention include but are not limited to small organic molecules that affect the expression of the CD38/SM38 gene or some other gene involved in the CD38/SM38 signal transduction pathway (e.g., by interacting with the regulatory region or transcription factors involved in gene expression); or such compounds that affect the enzyme activities of the CD38/SM38 or the activity of some other factor involved in modulating CD38/SM38 enzyme activity, such as for example, a protein that ribosylates CD38/SM38 and thereby inactivates CD38/SM38 enzyme activities.

5.3. Compositions Containing Modulators of CD38/SM38 and their Uses

The present invention provides for methods of modulating cell migration comprising contacting a cell expressing CD38 with an effective amount of a CD38 modulating compound, such as a CD38 agonist or antagonist identified using the assays as set forth in Section 5.1 supra. Additionally, the present invention provides for methods of modulating calcium responses and/or muscle contractility comprising contacting a cell expressing SM38 with an effective amount of a SM38 modulating compound, such as a SM38 agonist or antagonist identified using the assays as set forth in Section 5.1 supra. An "effective amount" of the CD38/SM38 inhibitor, i.e., antagonist, is an amount that decreases chemoattractant induced cell migration decreases intracellular calcium levels, decreases muscle contraction and/or that is associated with a detectable decrease in CD38/SM38 enzyme activity as measured by one of the above assays. An "effective amount" of the CD38/SM38 activator, i.e., agonist, is an amount that subjectively increases chemoattractant induced cell migration, increases intracellular calcium levels, increases muscle contraction and/or that is associated with a detectable increase in CD38/SM38 enzyme activity as measured by one of the above assays. Compositions of the invention also include modified CD38/SM38 substrates, modulators of CD38/SM38 expression and agonists/antagonists of cADPR.

The present invention further provides methods of modulating cell migration in a subject, comprising administering to the subject, a composition comprising a compound that modulates CD38 enzyme activity identified as set forth in Section 5.1 supra. The composition may comprise an amount of CD38 enzyme activator or inhibitor, modulators of CD38 expression, modified CD38 substrates, or direct agonists/antagonists of cADPR controlled Ca2+ responses. Accordingly, the present invention provides for compositions comprising CD38 activators and inhibitors.

The present invention provides for compositions comprising an effective amount of a compound capable of modulating the activity of CD38, the expression of CD38 and/or the activity of cADPR thereby regulating the migratory activity of cells, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

The invention provides for treatment or prevention of various diseases and disorders associated with cell migration by administration of a compound that regulates the expression or activity of CD38. Such compounds include but are not limited to CD38 antibodies; CD38 antisense nucleic acids, CD38 agonists and antagonists (see, FIGS. 2-3), modified CD38 substrates (see, FIG. 5) and cADPR agonists and antagonists (see, FIG. 6). In a non-limiting embodiment of the invention, disorders associated with hematopoietic derived cell migration are treated or prevented by administration of a compound that regulates CD38 activity. Such disorders include but are not limited to inflammation, ischemia, asthma, auto-immune disease, diabetes, allergies, infections, arthritis and organ transplant rejections.

The compounds of the invention are preferably tested in vitro, and then in vivo for a desired therapeutic or prophylactic activity, prior to use in humans. For example, in vitro assays which can be used to determine whether administration of a specific therapeutic is indicated, include in vitro cell culture assays in which cells expressing CD38 are exposed to or otherwise administered a therapeutic compound and the effect of such a therapeutic upon CD38 activity is observed. In a specific embodiment of the invention the ability of a compound to regulate, i.e., activate or inhibit cell migration may be assayed.

The present invention further provides methods of modulating the muscle contraction or other physiologic parameters in helminths such as *S. mansoni* by administering to helminth infected subject, a composition comprising a compound that modulates SM38 enzyme activity identified as set forth in Section 5.1 supra. The composition may comprise an amount of SM38 enzyme activator or inhibitor, modulators of SM38 expression, modified SM38 substrates, or direct agonists/antagonists of cADPR controlled Ca2+ responses. Accordingly, the present invention provides for compositions comprising SM38 activators and inhibitors.

The present invention provides for compositions comprising an effective amount of a compound capable of modulating the activity of SM38, the expression of SM38 and/or the activity of cADPR thereby regulating the activity and viability of the parasite, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

The invention provides for treatment or prevention of various diseases and disorders associated with helminth infections. Such compounds include but are not limited to SM38 antibodies; SM38 antisense nucleic acids, SM38 RNAi molecules, SM38 agonists and antagonists (see, FIGS. 2-3), modified SM38 substrates (see, FIG. 5) and cADPR agonists and antagonists (see, FIG. 6). In a non-limiting embodiment of the invention, disorders associated with helminth infection are treated or prevented by administration of a compound that regulates SM38 activity. Such disorders include but are not limited to granuloma formation and fibrosis in the liver and lung.

The compounds of the invention are preferably tested in vitro, and then in vivo for a desired therapeutic or prophylactic activity, prior to use in humans. For example, in vitro assays which can be used to determine whether administration of a specific therapeutic is indicated, include in vitro cell culture assays in which cells expressing SM38 are exposed to or otherwise administered a therapeutic compound and the effect of such a therapeutic upon SM38 activity is observed. In a specific embodiment of the invention the ability of a compound to regulate, i.e., activate or inhibit muscle contractility or intracellular calcium accumulation. Additionally, the compounds of the invention may be assayed for their effect on *S. mansoni* pathogenesis, growth, differentiation, and reproduction in a mouse model for *S. mansoni* infection. Such assays would include the testing for effects on proliferation of parasites, maturation of female worms, quantity of granulomas in liver and lung, quantity of eggs in liver, lung bladder and intestines, quantity of worms in lung and liver and quantity of miracidia detected in urine and feces.

Additionally, the compounds of the invention may be assayed for their effect on *S. mansoni* pathogenesis, growth, differentiation, and reproduction. Such compounds could be tested in a mouse model for *S. mansoni* infection. Such assays would include the testing for effects on proliferation of parasites, quantity of granulomas in liver and lung, quantity of eggs in liver, lung bladder and intestines and quantity of miracidia detected in urine and feces.

The invention provides methods of treatment and/or prophylaxis by administration to a subject of an effective amount of a compound of the invention. In a preferred aspect, the compound is substantially purified. The subject is preferably an animal, and is preferably a mammal, and most preferably human.

Various delivery systems are known and can be used to administer a compound capable of regulating CD38 activity, cADPR, or CD38 expression, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429-4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, by use of an inhaler or nebulizer, and formulation with an aerosolizing agent.

In a specific embodiment, it may be desirable to administer the compositions of the invention locally to a specific area of the body; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non porous, or gelatinous material, including membranes, such as sialastic membranes, or fibers.

The present invention also provides pharmaceutical compositions. Such compositions comprise a therapeutically effective amount of a compound capable of regulating CD38 activity, cADPR activity or CD38 expression and a pharmaceutically acceptable carrier. In a specific embodiment, the term "pharmaceutically acceptable" means approved by a regulatory agency of the Federal or a state government or listed in the U.S. Pharmacopeia or other Generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. The composition can be formulated as a suppository, with traditional binders and carriers such as triglycerides. Oral formulation can include standard carvers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical sciences" by E. W. Martin. Such compositions will contain a therapeutically effective amount of the therapeutic compound, preferably in purified form, together with a suitable amount of carrier so as to provide the form for proper administration to the patient. The formulation should suit the mode of administration.

The amount of the compound of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses maybe extrapolated from dose response curves derived from in vitro or animal model test systems. Additionally, the administration of the compound could be combined with other known efficacious drugs if the in vitro and in vivo studies indicate a synergistic or additive therapeutic effect when administered in combination.

The invention also provides a pharmaceutical pack or kit comprising one or more containers filled with one or more of the ingredients of the pharmaceutical compositions of the invention, optionally associated with such container(s) can be a notice in the form prescribed by a governmental agency regulating the manufacture, use or sale of pharmaceuticals or biological products, which notice reflects approval by the agency of manufacture, use or sale for human administration.

5.4. Vaccine Directed to SM38

The SM38 protein, as well as polypeptide components, may be used in vaccines against *S. mansoni*. The vaccines comprise an immunologically effective amount of the immunogen, i.e., SM38, in a pharmaceutically acceptable carrier. The combined immunogen and carrier may be an aqueous solution, emulsion, or suspension. An immunologically effective amount is determinable by means known in the art without undue experimentation, given the teachings contained herein. The carriers are known to those skilled in the art and include stabilizers, diluents, and buffers. Suitable stabilizers include carbohydrates, such as sorbitol, lactose, manitol, starch, sucrose, dextran, and glucose and proteins, such as albumin or casein. Suitable diluents include saline, Hanks Balanced Salts, and Ringers solution. Suitable buffers include an alkali metal phosphate, an alkali metal carbonate, or an alkaline earth metal carbonate. The vaccine may also contain one or more adjuvants to improve immunogenicity. Suitable adjuvants include aluminum hydroxide, aluminum phosphate, or aluminum oxide or a composition that consists of a mineral oil, such as Marcol 52, or a vegetable oil and one or more emulsifying agents.

The vaccines of the invention are prepared by techniques known to those skilled in the art, given the teachings contained herein. Generally, the immunogens are mixed with the carrier to form a solution, suspension, or emulsion. One or more of the additives discussed above may be in the carrier or may be added subsequently. The vaccine preparations may be dessicated, for example, by freeze drying for storage purposes. If so, they may be subsequently reconstituted into liquid vaccines by the addition of an appropriate liquid carrier.

The vaccines are administered to humans or other mammals susceptible to *S. mansoni* infection, or related worm infections. They can be administered in one or more doses. The vaccines may be administered by known routes of administration for this type of vaccine. The preferred routes are intramuscular or subcutaneous injection. Accordingly, the invention also comprises a method for inducing an immune response to SM38 in a mammal in order to protect the mammal against infection by *S. mansoni*. The method comprises administering an immunologically effective amount of the immunogens of the invention to the host and, preferably, administering the vaccines of the invention to the host.

6. EXAMPLE

Neutrophils Require CD38 for Chemotaxis, Capacitative $Ca^+$ Entry and Bacterial Clearance The subsection below describes data demonstrating that calcium entry in chemoattractant activated neutrophils is controlled by cADPR, a product of the CD38 enzyme reaction. The capacitative calcium influx, controlled by the cADPR produced by CD38, is required for neutrophils to migrate efficiently to chemoattractants.

6.1. Materials and Methods

6.1.1. Mice

C57BL/6J×129 CD38KO F2 animals (Cockayne et al., 1998 *Blood* 92:1324-1333) were backcrossed 6 generations (N6) to C57BL/6J and then inbred to produce homozygous congenic C57BL/6J.129 CD38KO mice. CD38-Rag-2 double KO (dKO) mice were produced by crossing C57BL/6J.129 (N6) CD38KO mice with C57BL/6J.129 (N8) Rag-2 KO mice (Shin Kai et al., 1992 *Cell* 68:855-867) and then mating the offspring to obtain homozygous double KO animals. Bone marrow chimeric mice were produced by transplanting $1 \times 10^7$ whole bone marrow cells isolated from WT or CD38KO mice into lethally irradiated (950 rad) WT hosts. All mice were bred and maintained in the Trudeau Institute Animal Breeding Facility.

6.1.2. cADPR Content Measurements

Mouse tissues were isolated from whole-body perfused WT or CD38KO mice and were flash frozen in liquid nitrogen. Bone marrow myeloid cells were flushed from the tibias, and femurs of Rag-2KO or Rag-2-CD38 dKO mice. cADPR content in mouse tissues and bone marrow myeloid cells was then measured as previously described (Vu et al., 1997 *Biochem Biophys Res Commun* 236:723-726).

*S. pneumoniae* infection. Mice were infected intra-tracheally with 100 or 1000 CFU *S. pneumoniae* type 4 (Klein Strain) from American Type Tissue Culture (Rockville, Md.). Blood, bronchial-aveolar lavage fluid (BAL) and lung tissue were collected from infected mice (Garvy et al., 1996 *Inflammation* 20:499-512). Bacterial titers in lung homogenate and blood were calculated on a per lung basis or per ml of blood. BAL cells were enumerated from cyto-centrifuge preparations.

6.1.3. In Vitro Chemotaxis Assays

Bone marrow neutrophils were purified (95% purity) by positive selection using biotinylated GR-1 (PharMingen) and MACS Streptavidin Microbeads (Miltenyi Biotec, Auburn Calif.). Chemotaxis assays (Falk et al., 1980 *J. Immuno. Methods* 33:239-247) were performed using 24-well transwell plates with a 3 µm pore size polycarbonate filter (Costar, Cambridge, Mass.). Medium (HBSS+Ca2++Mg2+), fMLP (1 µM, Sigma, St. Louis, Mo.), or IL-8 (100 nM, Sigma) was placed in the lower and/or upper chamber in a checkerboard format. 1×105 neutrophils were loaded in the upper chamber and the plates were incubated at 37° C. for 45 min. The transmigrated cells were collected from the lower chamber, fixed and counted on the flow cytometer (FACS Calibur, Becton Dickinson, San Jose Calif.). To determine the absolute number of cells in each sample, a standard number of 20 µM size fluorescent microspheres (Polysciences, Inc. Warrington, Pa.) was added to each tube and counted along with the cells. The total number of transmigrated cells=the number of counted neutrophils×total number of beads/beads counted. In some experiments, neutrophils were incubated in EGTA (2 mM) or pre-treated for 20 min with 8-Br-cADPR (25-100 µM, Sigma) or N(8-Br-A)D+(1.0 mM).

6.1.4. CD38 Expression

Bone marrow, blood or peritoneal cavity cells were isolated from WT or CD38KO mice and stained with anti-mouse GR-0.1 FITC, anti-mouse MAC-1 PE and anti-mouse CD38 APC (PharMingen, San Diego Calif.). Human peripheral blood neutrophils were isolated on a ficoll gradient and then stained with anti-hCD15-FITC (Becton Dickinson, San Jose Calif.) and anti-hCD38-Biotin (Caltag Laboratories, Burlingame Calif.). Mouse and human neutrophils were analyzed by flow cytometry, gating on the MAC-1+ GR-1+ for mouse neutrophils and CD 15+ for human neutrophils. To induce an inflammatory response, mice were injected with 1 ml 3% thioglycollate medium intra-peritoneally (Becton Dickinson, Cockeysville Md.). The animals were sacrificed 12 hrs post-injection, and the cells infiltrating the peritoneal cavity were collected.

6.1.4. Measurement of CD38 Cyclase Activity

Measurement of CD38 cyclase activity. 1×10$^6$ purified bone marrow neutrophils were incubated for 20 min at 37° C. in 100 µl HBSS in a 96 well microplate. NGD (40 µM) (Sigma) was added and the enzymatic conversion of NGD+ to cGDPR was measured fluorometrically (Graeff et al., 1994 *J. biol. Chem.* 269:30260-30267) over the next 10 minutes (415 nm emission and 300 nm excitation).

6.1.5. RyR.-3 MRNA Expression in Neutrophils cDNA was prepared from RNA isolated from purified bone marrow neutrophils or brain tissue. 30 cycles (annealing temperature 61° C.) RT-PCR was performed with 0.03-2 µg input cDNA and RyR-3 specific primers (Guse et al., 1999 *Nature* 398:70-73).

Synthesis of N(S-Br-A)D+. N(8-Br-A)D+ was synthesized as previously described (Abdallah et al. 1975 *Eur. J Biochem* 50:475-481).

6.1.6. Intracellular Calcium Measurements

Purified bone marrow neutrophils were resuspended in cell loading media (HBSS with Ca$^{2+}$ and Mg$^{2+}$+1% FBS+4 mM probenecid) at 1×10$^7$ cells/ml. The cells were incubated at 37° C. for 30 min with the fluorescent dyes Fluo-3 AM (4 µg/ml) and Fura Red AM (10 µg/ml) (Molecular Probes, Eugene OR) and then washed twice and resuspended in cell loading medium or calcium-free medium at 1×10$^6$ cells/ml. In some experiments, cells were permeabilized in 5 µM digitonin in calcium-free media. In other experiments, cells were preincubated with EGTA (2 mM), 8-Br-cADPR (10-100 µM), ruthenium red (Sigma) or N(8-Br-A)D+ (1 mM) and then stimulated with the carrier control (DMSO 0.01%), fMLP (1 µM), IL-8 (100 nM), ryanodine (1 µM), cADPR (100 µM) or thapsigargin (1 µM). The accumulation of [Ca$^2$+]i in individual cells was assessed by flow cytometry measuring the fluorescence emission of Fluo-3 in the FL-1 channel and Fura-Red in the FL-3 channel. Data was analyzed using FlowJo 3.2 (Tree Star, Inc. San Carlos, Calif.). The relative [Ca2+]i was expressed as the ratio between Fluo-3 and Fura Red mean fluorescence intensity over time.

6.2. Results

CD38 is the primary ADP-ribosyl cyclase expressed in lymphoid tissues. To directly test the requirement for CD38 and cADPR in calcium-sensitive immunologic responses in vivo, CD38 knockout (CD38KO) mice where generated (Cockkayne et al. 1998 *Blood* 92:1324-1333), To determine whether CD38 is the primary cyclase expressed in mice, the cADPR content in tissues and cells isolated from CD38KO and C57BL/6J wild-type (WT) mice were compared (Table 1).

TABLE 1

Comparison of cADPR content in tissues isolated from CD38KO and WT animals.

| Tissue | cADPR content WT tissue (pmol/mg protein) | cADPR content CD38KO tissue (pmol/mg protein) |
|---|---|---|
| Spleen | 2.108 ± 0.334 | (0.298 ± 0.091* |
| Thymus | 0.769 ± 0.182 | 0.335 ± 0.088** |
| BM myeloid | 0.633 ± 0.111 | 0.257 ± 0.032* |
| Lung | 0.847 ± 0.213 | 0.480 ± 0.069 |
| Kidney | 0.488 ± 0.119 | 0.418 ± 0.070 |
| Heart | 1.249 ± 0.324 | 1.014 ± 0.237 |
| Brain | 3.865 ± 0.866 | 3.127 ± 0.316 |

Extracts were prepared from tissues isolated from 8-12 wk old CD38KO or WT mice or from bone marrow (BM) myeloid cells isolated from Rag-2KO or Rag-2-CD38 double KO mice and were analyzed for cADPR content. Three separate purifications and analyses were performed on tissues isolated from 3 mice/analysis.
*P-0.01,
**P = 0.07;
Anova analysis.
Limit of detection, 0.2 pmol/mg protein.

WT tissues containing primarily lymphoid or myeloid cells, such as spleen, thymus and lymphoid deficient bone marrow (myeloid cells), had easily detectable levels of cADPR. In contrast, cADPR was not detected in lymphoid or myeloid tissues isolated from CD38KO mice. However, the cADPR content of CD38KO tissues such as brain, kidney and heart was nearly equivalent to the cADPR content of the same WT tissues. Thus, other unknown cyclases must be responsible for cADPR production in organs such as brain and heart, however, CD38 is the predominant ADP-ribosyl-cyclase expressed by myeloid and lymphoid cells.

CD38 deficient mice are more susceptible to bacterial infection. To test the requirement for CD38 and cADPR in innate inflammatory immune responses, CD38KO and WT mice were infected with *Streptococcus pneumoniae* and assessed survival (FIG. 7A). It was observed that the LD50 for CD38 KO animals is at least 10-fold lower than for WT mice, as 100 colony forming units (CFU) killed 50% of the CD38KO mice within 2.5 days of infection, while 1000 CFU were required to kill 50% of the WT animals in the same time period.

Since CD38 is expressed by the responding immunocytes and the bronchial epithelium (Fernandez J E et al., J. biol Reg Homeost Agents 12:81-91), WT or CD38KO bone marrow was transplanted into irradiated WT hosts to test whether CD38 expression in the lung and/or immune system was necessary for protection. The reconstituted chimeric animals possessed either CD38+ or CD38-deficient bone-marrow derived cells, while all other cell types, including the bronchial epithelium, were of WT origin in both groups of animals. The reconstituted mice were then infected with S pneumoniae and survival was monitored (FIG. 7B). Reconstituted animals receiving CD38KO bone marrow were much more susceptible to infection compared to mice receiving WT bone marrow, indicating that the increased susceptibility of CD38KO mice to S pneumoniae infection is due to the loss of CD38 on bone marrow-derived lymphoid and/or myeloid cells.

To determine whether the increased susceptibility of CD38KO animals to S pneumoniae was due to an inability to restrain bacterial growth and spreading to systemic sites, CD38KO and WT mice were infected with 1000 CFU of S. pneumoniae and bacterial titers were assessed in lung and blood 12 hours post-infection (FIG. 7C). The bacterial titer in the lungs of CD38KO mice was increased five-fold compared to WT controls. However, the bacterial burden in the blood of the CD38KO mice was 200-500 times greater than in WT mice, indicating that the bacteria rapidly disseminate in CD38KO mice.

To determine whether myeloid or lymphoid cells were responsible for the increased bacterial spreading, Rag-2 KO mice (Shin Kai, et al., 1992 Cell 68:855-867) (which lack lymphocytes but can express CD38 on all myeloid cells) and CD38-Rag-2 double knockout mice (which lack lymphocytes and cannot express CD38 on their myeloid cells) were infected with 1000 CFU S. pneumoniae and then bacterial titers were determined in lung and blood 12 hours later (FIG. 7C). The bacterial titers in the lungs and blood of the lymphoid-deficient CD38-Rag-2 double KO mice were as high as those seen in the CD38KO mice and were significantly increased when compared to Rag-2 KO or WT mice. Thus, CD38 deficient myeloid cells are responsible for the increased susceptibility of CD38KO mice to S. pneumoniae.

Figure 8A:
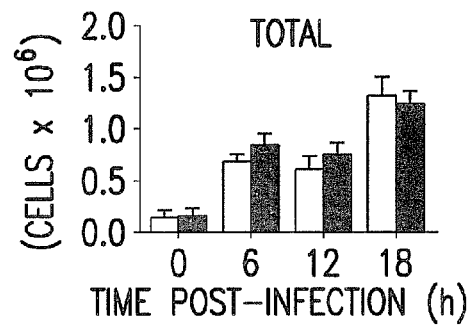
Figure 8C:
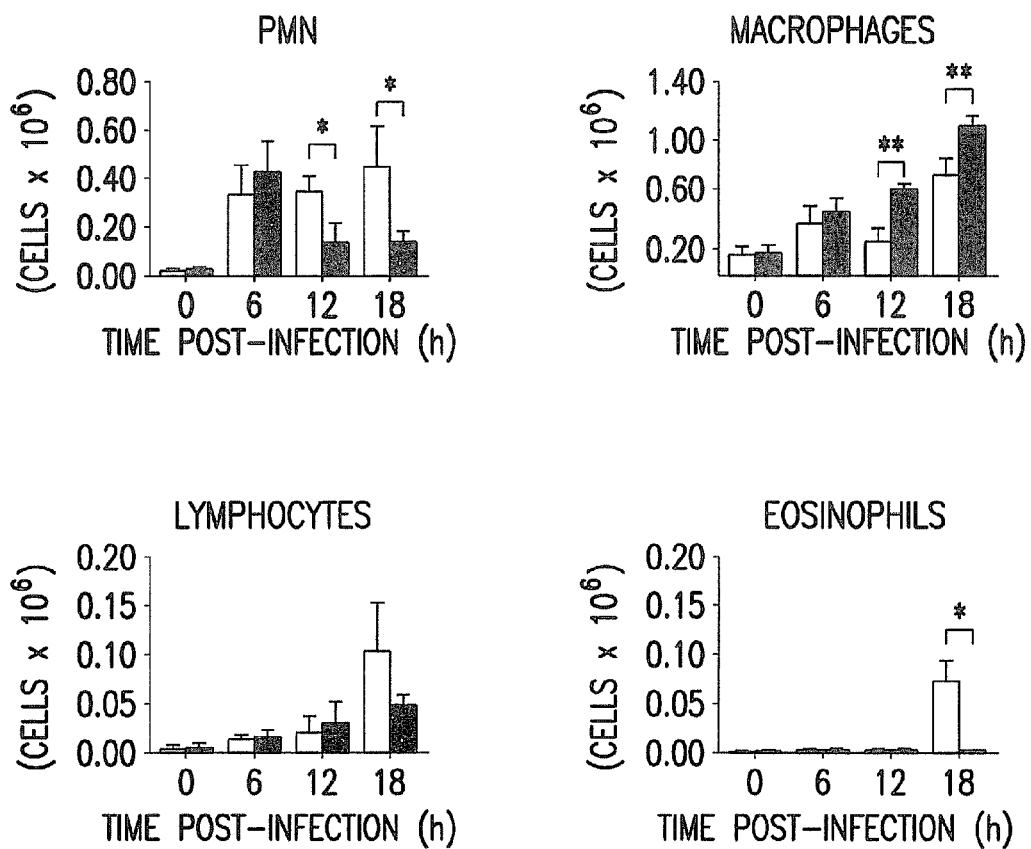
Figure 8B:
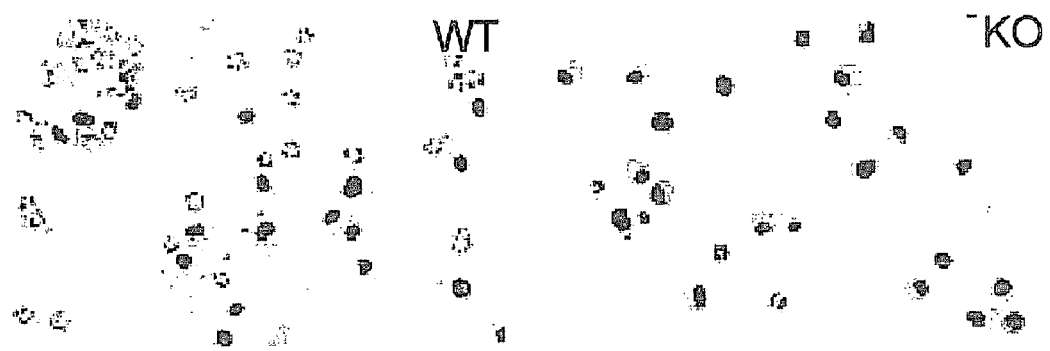

CD38 deficient neutrophils do not accumulate at sites of infection and inflammation. To test whether myeloid cells were appropriately recruited to the lungs of S. pneumoniae-infected CD38KO animals, CD38KO and WT mice were infected and then the cells that were recruited to the lung airways after infection were enumerated. The total number of cells in the airways of CD38KO and WT animals increased equivalently from 6 to 18 hours post-infection (FIG. 8A). However, neutrophils were the predominant cell type found in the lungs of WT animals 12-18 hours post-infection, while the cellular infiltrate in the lungs of the CD38KO animals was composed primarily of macrophages (FIG. 8B-C). Thus, CD38 appears to be required for sustained recruitment of neutrophils to the site of infection and inflammation.

Figure 8D:
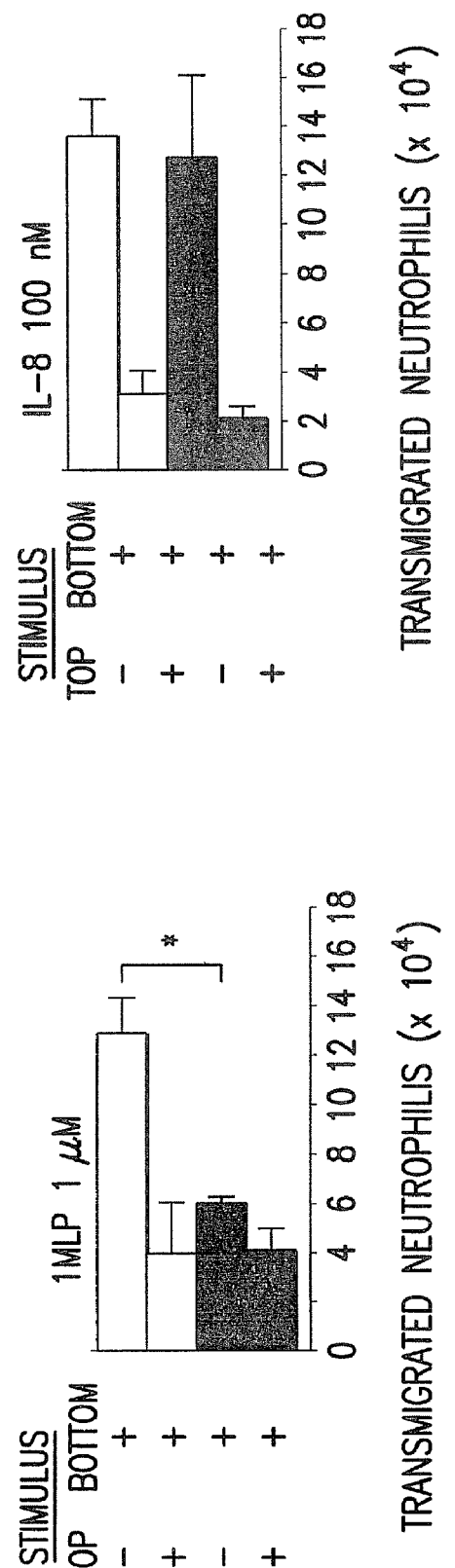

CD38 deficient neutrophils make a defective chemotactic response to the chemoattractant fMLP. Neutrophils migrate to sites of infection in response to gradients of chemokines and chemoattractants that are produced by the local cells and by the invading pathogen (Hub et al. 1996 Chemoattractant Ligands and Their Receptors (ed. Horuk) 301-325 (CRC Press, Boca Raton, Fla.); Servant G. et al., 2000 Science 287:1037-1040; Gao, J. L., 1999 J. Exp. Med. 189:657-662). Chemoattractants rapidly activate neutrophils and induce random migration (chemokinesis). If a chemotactic gradient exists, the activated neutrophils polarize their leading edge toward the highest concentration of the gradient and migrate directionally 16 (chemotaxis). It has been previously demonstrated that neutrophils home to sites of infection upon stimulation of their N-formylpeptide receptor (FPR) by bacterially-derived formylated such as formyl-methionyl-leucyl-phenylalanine (fMLP). To test whether CD38KO neutrophils were defective in their ability to chemotax to fMLP, the ability of CD38KO and WT neutrophils to migrate by chemokinesis and chemotaxis in a transwell checkerboard assay was determined (Falk et al., 1980 J. Immunol. Methods 33:239-247) (FIG. 8D). When fMLP was absent from the top and bottom chamber, or when fMLP was placed only in the top chamber, few (<2300 cells), but equivalent numbers, of the CD38KO and WT neutrophils migrated to the bottom chamber. When an equal concentration of t1VILP was present in the top and bottom chamber (chemokinesis conditions), increased, but similar, numbers of WT and CD38KO neutrophils migrated to the bottom chamber, indicating that activation-induced chemokinesis to fMLP was equivalent between CD38KO and WT neutrophils. When fMLP was present in the bottom chamber only (chemotaxis conditions), the migration of WT neutrophils to the bottom chamber was further increased. However, CD38KO neutrophils migrated only marginally better in the presence of a chemotactic gradient than in the absence of a fMLP gradient, indicating that CD38KO neutrophils can be activated to migrate by bacterial chemoattractants but are unable to follow the chemotactic gradient. To determine if this was a general property of CD38KO neutrophils, the same experiments were performed using the chemokine IL-8, which is a potent activator of neutrophils (Baggiolini et al., 1989 J. Clin. Invest 84:1045-1049). In contrast to what was observed with fMLP, the IL-8-induced chemotaxis of CD38KO and WT neutrophils was equivalent (FIG. 8D). Thus, these data indicate that CD38KO neutrophils make defective chemotactic responses to some, but not all, chemoattractants.

Figure 9A:
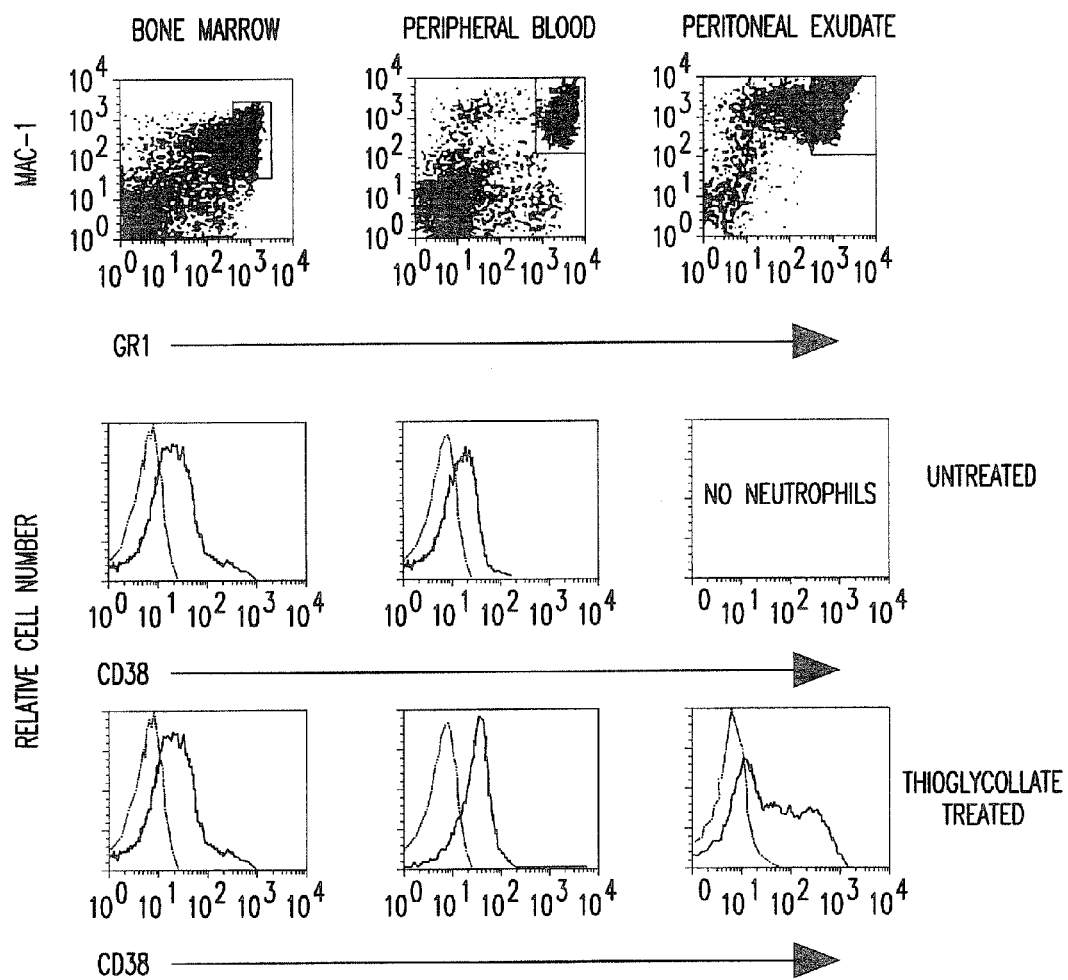
Figure 9B:
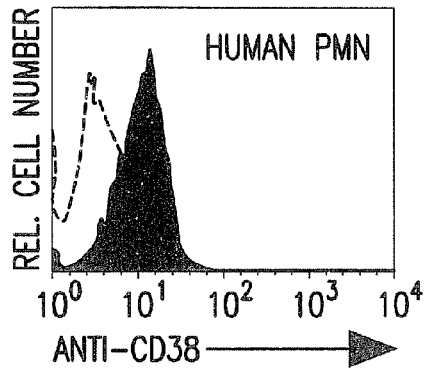
Figure 9C:
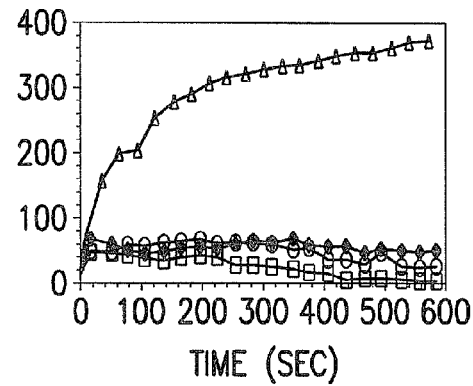
Figure 9E:
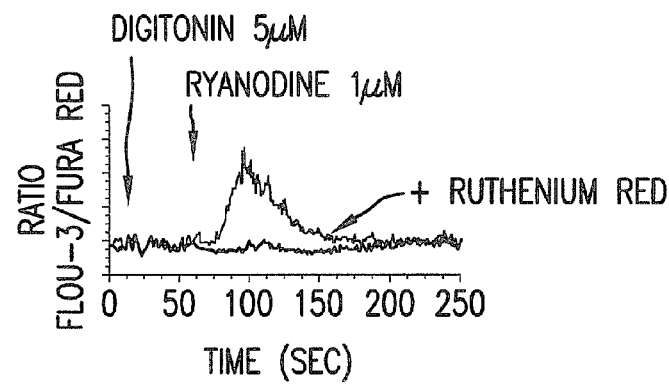
Figure 9F:
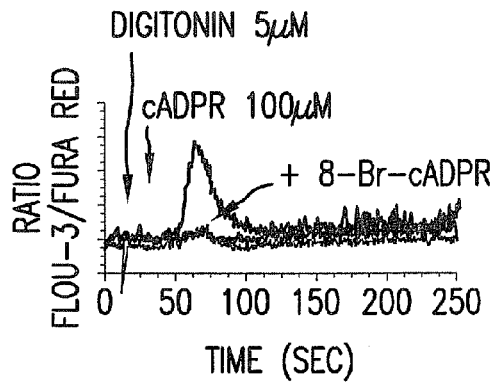
Figure 9G:
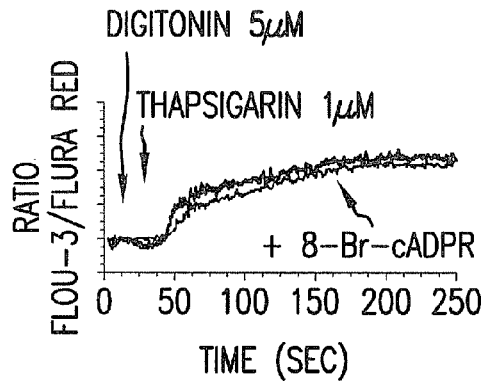
Figure 9D:
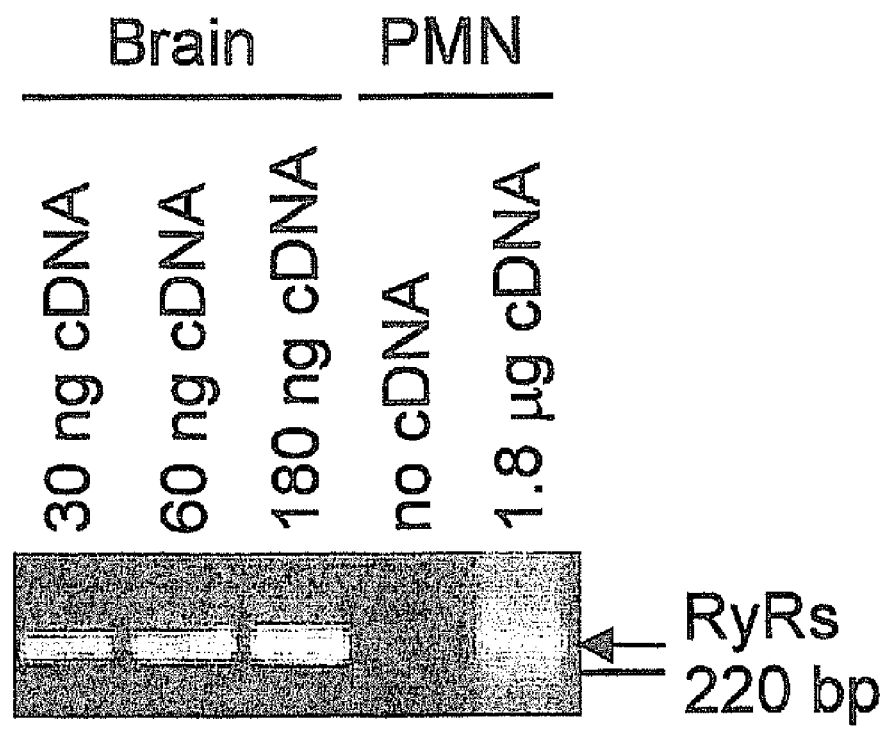

CD38 is expressed and enzymatically active on neutrophils. Since CD38KO neutrophils appear to have an intrinsic defect in chemotaxis, CD38 expression and enzyme activity on mouse and human neutrophils was determined. Neutrophils isolated from the bone marrow and blood of WT mice clearly expressed CD38 (FIG. 9A), and likewise, human peripheral blood neutrophils also expressed CD38 (FIG. 9B). Interestingly, when WT mice were injected intraperitoneally with the inflammatory agent, thioglycollate, CD38 expression increased significantly on the neutrophils isolated from the blood and peritoneal cavity (FIG. 9D). Next, to test whether CD38-expressing neutrophils can catalyze the cyclase reaction, WT and CD38KO neutrophils were incubated with the NAD+analogue, nicotinamide guanine dinucleotide (NGD), and then measured the cyclization of NGD into the fluorescent compound cyclic GDP-ribose (Graeff et al., 1994 J. Biol. Chem. 269:30260-30267) (cGDPR). As shown in FIG. 9C, WT neutrophils, but not CD38KO neutrophils, produced cGDPR rapidly upon incubation with NGD, indicating that CD38-expressing neutrophils are competent to produce cyclic nucleotides.

cADPR and ryanodine induce intracellular calcium release in neutrophils. Since cADPR induces intracellular calcium release through ryanodine receptor (RyR) gated stores (Galione et al. 1991 Science 253:1143-1146), it was tested whether the RyR/cADPR calcium signaling pathway was functional in neutrophils. RT-PCR analysis showed that neutrophils express mRNA for RyR3 (Sorrentino, V. et al., 1993 TIPS 14:98-103; Hakamata Y. et al., 1992 FEBS Lett 312: 229-235), although at levels much lower than seen in the brain (FIG. 9D). To test whether the RyRs expressed by neutrophils were functional, intracellular calcium levels ($[Ca^{2+}]i$) were measured in neutrophils that were permeabilized in calcium-free buffer and then stimulated with ryanodine (FIG. 9E). A small, but reproducible, increase in $[Ca^{2+}]$ in ryanodine-stimulated neutrophils that could be blocked by the RyR inhibitor, ruthenium red was observed (Galione et al. 1991 *Science* 253:1143-1146). Next, to test whether cADPR could induce intracellular calcium release in neutrophils, neutrophils were permalized in calcium-free buffer and then stimulated the cells with purified cADPR (FIG. 9F). A small, but easily detectable, rise in intracellular free calcium was observed. No calcium release was observed when the cADPR was first hydrolyzed by heat inactivation (Lee et al., 1989 *J. Biol. Chem.* 264:1608-1615) or when the cells were pre-treated with 8-Br-cADPR, an inactive analogue of cADPR that competitively antagonizes cADPR binding to RyRs (Guse et al., 1994 *Annu. Rev. Immunol* 12:593-633). The specificity of the antagonist, 8-Br-cADPR, for cADPR mediated calcium release was further demonstrated by showing that 8-Br-cADPR was unable to block the accumulation of intracellular free calcium mediated by thapsigargin (FIG. 9G). Together, the data demonstrate that intracellular calcium can be released through RyR and cADPR-mediated mechanism in neutrophils.

Figure 10A:
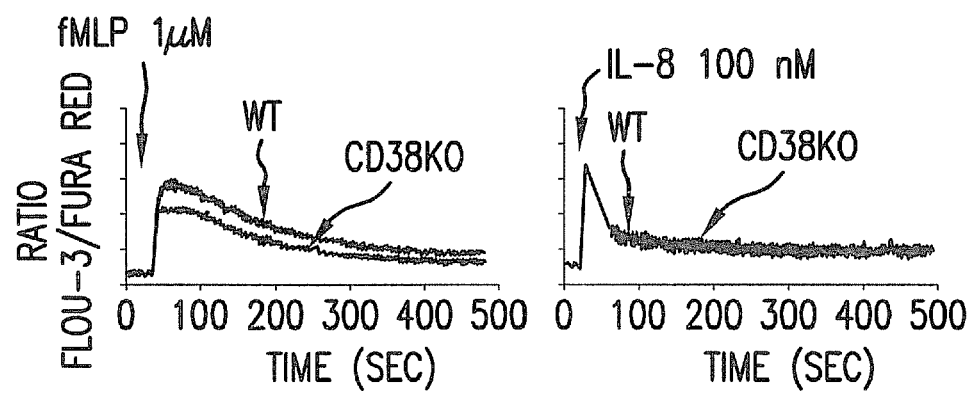

CD38 catalyzed cADPR is required for extracellular calcium influx in fMLP-activated neutrophils. Signaling through chemokine/chemoattractant G-protein coupled receptors such as FPR and the IL-8 receptors results in increased $[Ca^{2+}]i$ due to a combination of intracellular calcium release and extracellular calcium influx (Murphy, P. M., 1994 *Annu. Rev. Immunol* 12:593-633; Demaurex N. et al., 1994 *Biochem J.* 297:595-601; Schorr W. et al., 1999 *Eur. J. Immunol.* 29:897-904: Lew et al., 1989 *Eur. J. Clin. Invest.* 19:338-346). Since CD38KO neutrophils were defective in chemotaxis assays to fMLP and lacked the ability to produce the calcium mobilizing metabolite, cADPR, it was hypothesized that calcium mobilization in response to fMLP would be deficient in CD38KO neutrophils. To test this, CD38KO or WT neutrophils were stimulated with fMLP or IT-8 in calcium-free media and intracellular calcium release was measured (FIG. 10A). An immediate sharp rise in intracellular calcium was observed that gradually declined over next 5 minutes in fMLP-stimulated WT neutrophils. In contrast, in fMLP-stimulated CD38KO cells, the magnitude of $[Ca^{2+}]i$ after fMLP stimulation was reduced by approximately 20% and the $[Ca^{2+}]i$ declined to baseline at least 2 minutes earlier. Unlike the reduced $[Ca^{2+}]i$ found in fMLP-stimulated CD38KO neutrophils, the $[Ca^{2+}]I$ of IL-8 stimulated CD38KO and WT neutrophils was identical. Thus, these data suggested that CD38 may be necessary for optimal intracellular calcium release after fMLP, but not IL-8, stimulation.

Figure 10B:
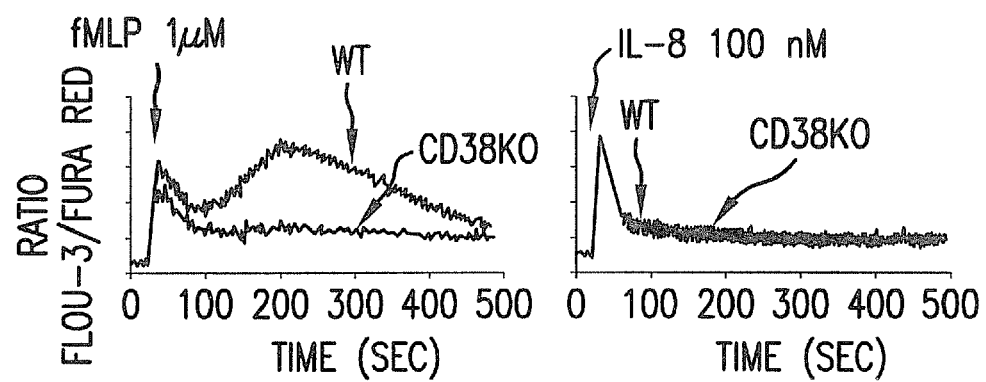

Next, to assess whether CD38 was required for extracellular calcium influx, stimulated CD38KO or WT neutrophils were stimulated with fMLP or IL-8 in calcium-containing media (FIG. 10B). When we added fMLP to WT neutrophils, a rapid increase in $[Ca^{2+}]i$, due to intracellular calcium release was observed, as well as a second extended, increase in $[Ca^{2+}]i$, due to extracellular calcium influx. In striking contrast, the calcium influx phase of the response was essentially ablated in the fMLP-stimulated CD38KO neutrophils. Interestingly, when WT and CD38KO neutrophils were stimulated with IL-8 in calcium containing media, it was found that IL-8 induced a equivalent immediate increase in $[Ca^{2+}]i$ that rapidly declined to baseline levels in both WT and CD38KO neutrophils, indicating that IL-8 did not induce extracellular calcium influx in either WT or CD38KO neutrophils.

Figure 10C:
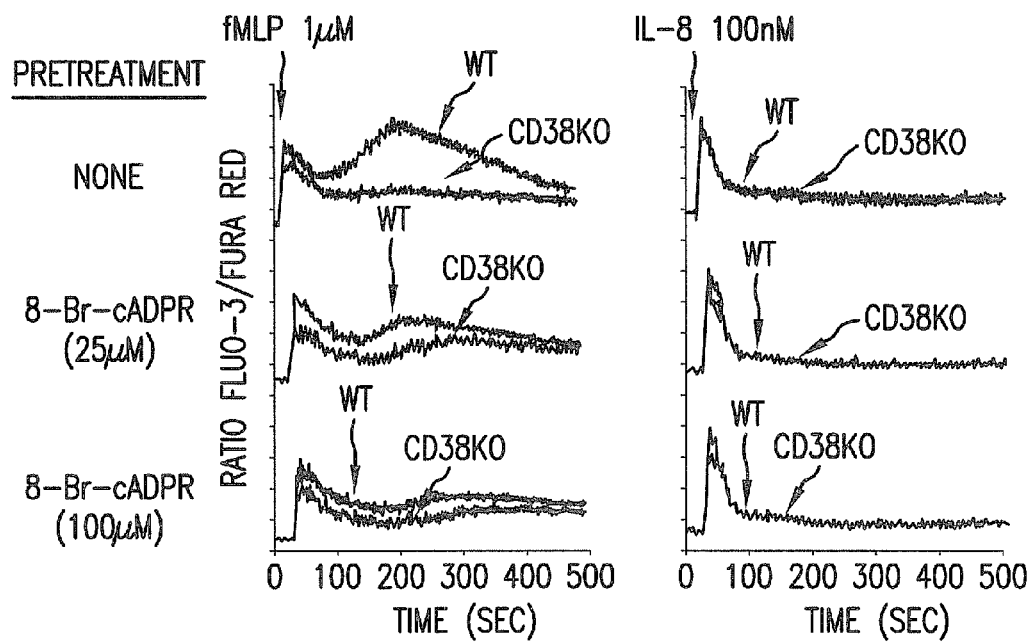

To determine whether cADPR regulates calcium mobilization in fMLP stimulated neutrophils, CD38KO and WT neutrophils were preincubated with increasing concentrations of the cADPR antagonist, 8-Br-cADPR, and then stimulated with fMLP or IL-8 (FIG. 10C). When 8-Br-cADPR-treated WT cells were stimulated with fMLP, the release of intracellular calcium as well as the influx of extracellular calcium was reduced in a dose-dependent fashion to the levels seen in CD38KO cells. In contrast, addition of 8-Br-cADPR to IL-8 stimulated neutrophils had absolutely no effect on the $[Ca^{2+}]i$ of either WT or CD38KO neutrophils. Together, these data indicate that CD38-produced cADPR regulates intracellular calcium release and extracellular calcium influx in response to fMLP, and that neither CD38 nor cADPR are necessary for calcium mobilization in IL-8 stimulated neutrophils.

Figure 10D:
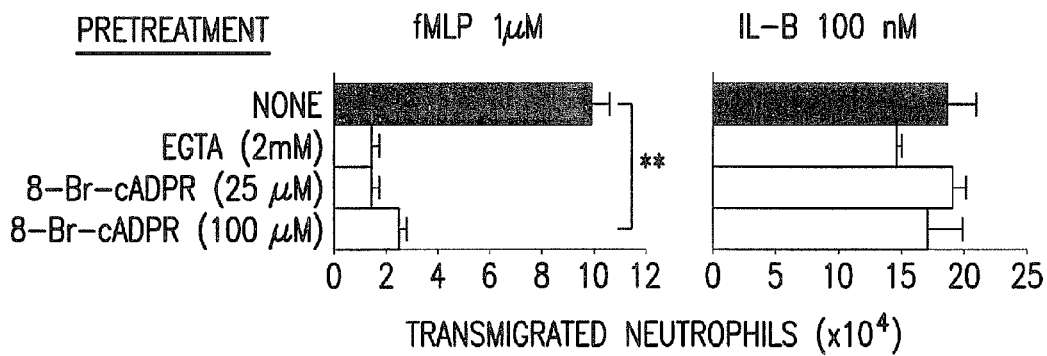

CD38 catalyzed cADPR is required for neutrophil chemotaxis to fMLP but not IL-8. To test whether cADPR-mediated calcium mobilization is required for chemotaxis to AMP, WT neutrophils were preincubated with either EGTA or 8-Br-cADPR and then chemotaxis to fMLP or IL-8 in a checkerboard chemotaxis assay was measured (FIG. 10D). When WT neutrophils (no pre-treatment) were incubated with media in the top chamber and fMLP or IL-8 in the bottom chamber, the cells efficiently migrated to the bottom chamber. However, if the extracellular calcium was chelated with EGTA or if the cells were pre-treated with the cADPR antagonist, 8-Br-cADPR, chemotaxis of the WT neutrophils to fMLP was reduced by more than 80%. Importantly, EGTA or 8-Br-cADPR treatment had absolutely no effect on the ability of neutrophils to chemotax to IL-8. Thus, extracellular calcium influx, regulated by cADPR-mediated intracellular calcium release, is necessary for EMLP-induced chemotaxis of neutrophils.

An analogue of NAD+inhibits neutrophil chemotaxis to fMLP, but not IL-8, in a CD38-dependent fashion. Since CD38 catalyzed cADPR appeared necessary for neutrophil chemotaxis to fMLP, it was predicted that chemotaxis could be inhibited by treating neutrophils with $NAD^+$ analogies that could be converted by CD38 into antagonists of the cADPR signaling pathway. To test this prediction, neutrophils with pretreated with nicotinamide 8-bromoadenine dinucleotide ($N(S-Br-A)D^+$), a substrate that can be converted by CD38 into 8-Br-cADPR, the cADPR antagonist that was used in our earlier experiments. To first test whether $N(8-Br-A)D^+$ altered extracellular calcium influx in flVILP-activated neutrophils, WT neutrophils were pretreated with $N(8-Br-A)D^+$, the cells were stimulated with AMP and then $[Ca^{2+}]i$ was measured (FIG. 11A). $N(8-Br-A)D^+$ pre-treatment inhibited the entry of extracellular calcium in fMLP-treated neutrophils. Next, WT and CD38KO neutrophils were pretreated with $N(8-Br-A)D^+$ or left in media alone, followed by testing for their ability to chemotax to fMLP (FIG. 11B) or IL-8 (FIG. 11C). Untreated WT neutrophils chemotaxed to both fMLP and IL-8, while untreated CD38KO neutrophils could not chemotax to fMLP, but could chemotax to IL-8. Interestingly, pre-treatment of WT neutrophils with $N(8-Br-A)D^+$ severely reduced neutrophil chemotaxis to fMLP but had no effect on their ability to chemotax to IL-8. Pre-treatment of the CD38KO neutrophils with $N(8-Br-A)D^+$ had no effect on the chemotaxis of the CD38KO neutrophils to either flVILP or IL-8, indicating that the $N(8-Br-A)D^+$ induced inhibition of fMLP-mediated chemotaxis was CD38 dependent. Together, the data demonstrate that $NAD^+$ analogues can regulate calcium responses and chemotaxis of neutrophils in a CD38-dependent fashion.

7. EXAMPLE

Mouse Model of Allergic Lung Disease and Role of CD38

The subsection below describes data demonstrating that CD38-deficient eosinophils are unable to be recruited to the site of airway inflammation induced by allergens.

7.1. Materials and Methods

OVA priming and sensitization. C57BL/6 WT mice were immunized intraperitoneally with 20 µg chicken ovalbutnin (OVA) adsorbed to alum. Immunized mice were sacrificed 30 days post-immunization and the OVA-primed CD4 T cells were purified from the spleen using MACS magnetic beads that were directly conjugated with anti-CD4. Naive CD4 T cells were purified using anti-CD4 conjugated MACS beads from unimmunized C57BL/6 WT mice. Naive or OVA-primed T cells were injected intravenously into either C57BL/6 WT or CD38KO recipients at $1 \times 10^7$ CD4 T cells per mouse to generate 4 groups of 10 mice each indicated in FIGS. 11A and B. Recipient mice were then sensitized intratracheally with 10 µg OVA in PBS on each of 7 consecutive days immediately following T cell transfer. Mice were sacrificed on the eighth day after T cell transfer, and infiltrating cells were removed from the airways and alveoli of the lungs by broncheoalveolar lavage as described in Section 6.2.2, supra. Total cells were then enumerated by counting on a hemocytometer and differential cell counts were performed by centrifuging cells on to a glass slide, staining with Diff-Quick and identifying at least 200 cells per slide at 400×.

7.2. Results

To determine if CD38 controls the recruitment of cells other than neutrophils to the lung, a mouse model of allergic lung disease that mimics many of the properties of human asthma was used (Lloyd C M et al., 2001, Adv. Immunol. 77:263-295). An important component a asthma is airway inflammation, which is thought to be induced or exacerbated by the activities of eosinophils that have been recruited to the lung. Although eosinophils are primarily responsible for the pathology of asthma (Broide, D H et al., 1991, J. Allergy Clin. Immunol. 88:637-648), their recruitment and function appears to be controlled by T cells that have been primed to allergenic antigens (Gavett et al., 1994, Respir. Cell Mol. Biol. 10:587-593). Such T cells often produce type 2 cytokines, such as IL-4, IL-5 and IL-13, as well as chemokines like eotaxin (Cohn, L. et al., 1988, J. Immunol. 161:3813-3816; Drazen J M et al., 1996, J. Exper Med. 183:1-5). To examine the ability of CD38 to regulate eosinophil recruitment independently of any effects of CD38 on T cell activation, WT mice were immunized with the antigen OVA. After 30 days, CD4 T cells from these OVA-primed mice were transferred to either WT or CD38KO recipients. As a control, naive CD4 T cells were transferred from unimmunized WT mice to either WT or CD38KO recipients. Recipient mice were then sensitized intratracheally with 10 µg of OVA in PBS on each of eight consecutive days immediately following T cell transfer. Mice were sacrificed on the ninth day after T cell transfer and the cells in the airways of the lungs were enumerated.

As seen in FIG. 12A, substantial numbers of neutrophils were recruited to the airways of WT mice regardless of whether they received naive or primed CD4 T cells. In contrast, although CD38KO trice that received primed T cells did have significantly more neutrophils in the airways than CD38KO mice that received naive T cells, relatively few neutrophils were recruited to the airways of CD38KO mice compared to the airways of WT mice. Thus, neutrophil recruitment to the lung in a model of allergic airway disease is also dependent on the expression of CD38.

Strikingly, the recruitment of eosinophils to the airways of OVA-sensitized mice was dependent on the presence of both primed CD4 T cells and the expression of CD38. As seen in FIG. 12B there was a 30-fold reduction in the numbers of eosinophils recruited to the lungs of CD38 K0 mice that had received primed CD4 T cells relative to that in WT mice that had received primed CD4 T cells and a 10-fold reduction in the numbers of eosinophils recruited to the airways of CD38KO mice that received naive CD4 T cells relative to that in WT mice that had received naive CD4 T cells. Therefore, the recruitment of eosinophils to the lung in a model of allergic airway disease is also dependent on CD38.

8. EXAMPLE

Cloning of S. mansoni CD38 Homologue

The subsection below describes the cloning and sequencing of a S. mansoni CD38 homologue referred to as SM38. Helminths, such as S. mansoni, are broadly defined as worm parasites that infect and can cause pathogenesis in most invertebrates, vertebrates and plant species. The genus Schistosoma consists of parasitic flatworms whose definitive habitat is the bloodstream of warm-blooded vertebrates. Four species of Schistosoma, including S. mansoni cause disease in 200-400 million humans per year and kill up to 1 million people each year (WHO, 1996). Additionally, at least two Schistosoma species infect domesticated cattle and sheep causing serious economic losses. Thus, it would be beneficial to develop effective antibiotic drugs that could be used to treat infected humans and/or animals. The pathogenesis of Schistosoma infection is caused mainly by the deposition of eggs by the mature worm into various tissues and organs of humans and animals where granulomas then form leading to fibrosis and tissue damage. However, the cercariae (immature worm) and fully mature worm also release a number of proteins and lipid mediators that can also induce an immune inflammatory response (Fusco, A C et al., 1991, J. Paristol. 77:649-657). The treatment of choice in schistosomaisis is the drug praziquantel which appears to induce calcium influx across the tegument of the worm causing immediate muscle contraction and paralysis (Kohn, A B et al., 2001, J. Biol. Chem 276: 36873-36876). Thus, drugs that modulate schistosome calcium responses, particularly within the muscle, might be effective in the treatment of this disease.

8.1. Materials and Methods

8.1.1. Cloning of Shistosoma mansoni CD38 Homologue

Primers were made corresponding to the EST sequence found in Genbank accession #AW017229. (5' primer: acatctttgtggtactgaatggctcgg and 3' primer: tgagtaatgtctcgacgtttgacctcg). S. mansoni cDNA libraries were obtained from Dr. Philip LoVerde (SUNY, Buffalo), and were subjected to PCR using the primers indicated above. The library (1-20 µl) and dH20 were heated to 70° C. for 10 minutes and were then combined with the remainder of the PCR reagents and cycled. The cycles were: 95° C. 5 minutes, 1 'cycle, followed by 95° C. 1 minute, 65° C. 1 minute and 72° C. 2 minutes for 35 cycles followed by 1 cycle at 72° C. for 5 minutes. The expected 330 by band corresponding to EST AW017229 was isolated, TOPO cloned, and then used as a probe to screen 250,000 plaques from the S. mansoni cDNA library. Five positives were isolated and then subjected to 3 more rounds of screening in order to produce plaque pure clones. All five clones were fully sequenced on both strands. The nucleotide sequence and amino acid translation of four of the clones were identical (referred to as SM38). The stop codon and polyadenylation sites were identified in all of the SM38 clones, but the initiation methionine was not present in any of the clones. To obtain the 5' end of the SM38 gene, a single primer extension approach (NAR, 1994, vol 22, No. 16, p 3427-3428) was utilized. A first round of PCR was performed using an external SM38 primer (5' catcgaataaccct-gatttcataacac) and the universal reverse primer for Bluescript. Two μL of this reaction was then subjected to PCR using an internal nested SM38 primer (5' gataaagtaagaactcgtgcc) and the universal reverse primer. A 200 and a 300 by band were identified from this reaction and were directly sequenced. The sequence obtained overlapped 124 by with the 5' end of the SM38 clones and included an additional 153 by of sequence, however the no stop codon was detected, indicating that we still did not have the 5' end of the gene. Therefore, classic 5"RACE (PNAS vol 85 pp 8998-9002, December 1998) was performed using cDNA prepared from RNA isolated from adult S. mansoni worms (RNA provided by Dr. P. LoVerde, SUNY Buffalo). 10× Taq buffer, dNTP's, cDNA and Expand High Fidelity Taq were combined with the dT-AP primer (see ref. For details) and cycled for 5 minutes at 95° C. followed by 2 minutes at 50° C. and 40 minutes at 72° C. After this 40 minute incubation the 5' external SM38 primer (see above) and AP primers were added and cycled for 35 cycles under the conditions: 95° C. for 15 sec, 47° C. for 30 sec, 72° C. for 2 minutes followed by a 5 minute extension at 720C. The reactions were run on a 1.5% agarose gel and a 300 by band was isolated using Qiagen Gel Kit. The 5' RACE product was directly sequenced with the AP and 5' external SM38 primer. Two potential initiation methionines were identified in the sequence and two stop codons were found 13-19 amino acids upstream of the methionine residues. The RACE product was subsequently cloned. All three clones containing SM38 sequence (Two PCR generated clones and one clone from the S. mansoni cDNA library) were contiguous and overlapping. When assembled, the SM38 sequence included 1049 by of sequence including 5' untranslated sequence, two potential initiation methionines, an open reading frame encoding a 303 amino acid protein, a stop codon, 3' untranslated sequence and a poly-adenylation site.

8.2. Results

Since drugs that modulate calcium responses in the muscle fibers of Schistosomes appear to be effective anti-helminth reagents (Kohn et al, 2001, J. Biol. Chem. 276:36873-36876), we set out to identify specific calcium modulating targets of Schistosomes. It has been recently shown that Schistosomes express Ryanodine Receptors (RyR) within their muscle fibers (Day et al., 2000, Parasitol. 120:417-420; Silva et al., 1998, Biochem. Pharmacol. 56:997-1003). Agonists of RyRs expressed in vertebrate smooth and skeletal muscle are known to regulate intracellular calcium release, voltage gated calcium influx and muscle contractility. Interestingly, S. mansoni muscle fibers treated with RyR agonists such as caffeine induced the release of intracellular calcium and induced contraction of the muscle fiber. Although drugs such as caffeine can modulate RyR-dependent calcium responses, the physiological modulator of RyRs, at least in vertebrate muscle fibers is cyclic ADP-ribose (cADPR). cADPR is a known calcium mobilizing metabolite that is produced by ADP-ribosyl cyclase enzymes such as the mammalian CD38 protein and the invertebrate Aplysia cyclase enzyme. To determine whether Schistosomes express an enzyme capable of producing the calcium mobilizing second messenger, cADPR, a search was performed of the publicly available EST sequences looking for Schistosome sequences that when translated would have homology to the mammalian CD38 and Aplysia enzymes. Three EST sequences (EST A1067047, EST AW017229 and EST N20756) were identified that could be assembled into a contiguous and overlapping sequence (FIG. 13). This assembled sequence shared limited but significant homology with both CD38 and the Aplysia cyclase enzymes.

To determine whether the assembled ESTs actually represented an authentic cDNA, primers were prepared from the sequence of EST AW017229 and performed PCR on a S. mansoni cDNA library. A 330 base pair fragment was isolated from the PCR reaction and was sequenced. As expected the sequence of the fragment matched that of the EST. The fragment was then used as a probe to screen 250,000 plaques from the S. mansoni cDNA library. Five independent plaques which hybridized to the EST probe were isolated, plaque purified and sequenced on both DNA strands. The sequence information was then used to design additional primers to isolate the 5' end of the cDNA (see methods). The complete cDNA sequence isolated from the S. mansoni library was then assemble and compared to the ESTs. The alignment, shown in FIG. 13, indicates that the contiguous assembly of the EST sequences was correct and that the cloned cDNA (referred to as SM38) included at least an additional 421 base pairs of sequence not found in any EST. Translation of the DNA sequence gave rise to a 299 amino acid sequence (FIG. 13) containing structural motifs typical of cyclase enzymes (Prasad, G S, 1996 Nature Struct. biol. 3:957-964). In particular, the SM38 protein contains conserved amino acid residues that align with critical catalytic and active site residues found in the Aplysia cyclase enzyme (Munshi C, et al., 1999, J. Biol. Chem. 274:30770-30777) and in mammalian CD38 (Munshi C, et al., 2000, J. Biol. Chem. 275:21566-21571; Graeff R., 2001, J. Biol. Chem. 276:12169-12173) (FIG. 15A-B). Additionally, cysteine residues that are critical for the assembly of the tertiary structure of the cyclase enzymes (Prasad G S, et al., 1996, NAture Struct. biol. 3:957-964) are also conserved in SM38; (FIG. 14A-B). Importantly, the SM38 cDNA sequence encodes for a complete cyclase enzyme domain.

Based on these results, we have shown that Schistosomes such as S. mansoni encode a protein (SM38) that is highly homologous at the structural level to enzymes that are capable of catalyzing the production of the calcium mobilizing second messenger, cADPR. Since Schistosomes also express RyRs which release intracellular calcium in response to cADPR, it is predicted that SM38 will be able to regulate calcium response in Schistosomes. Furthermore, since regulation of calcium influx, particularly in Schistosome muscle fibers can result in paralysis and clearance of the worm, we predict that agonists/antagonists of the SM38 and RyR pathways in Schistosomes may be effective as anti-helminth drugs.

9. EXAMPLE

Characterization of SM38

The subsection below demonstrates that Schistosoma SM38 is structurally similar to all of the other cyclase family members and is able to catalyze NAD⁺ glycohydrolase, ADP-ribosyl cyclase, cADPR hydrolase and transglycosidation reactions. The subsection also demonstrates that SM38 is expressed as a GPI-anchored protein on the outer tegument of adult worms, and is therefore an ideal vaccine target candidate as well as a potential target for small molecule enzyme antagonists.

9.1. Materials and Methods

9.1.1. SM38 Cloning

A blast search using the consensus amino acid sequence for cyclase family members (Prasad, et al., 1996, *Nature Struc. Biol.*, 3:957-964) was performed and an EST isolated from *Schistosoma mansoni* (Accession # AW017229) was identified. Primers specific for the EST (see FIG. 13) were synthesized (Sigma/Genosys), and the 330 bp cDNA was cloned by PCR amplification from a Lambda ZAP II cDNA library constructed from polyA⁺ mRNA isolated from adult worm pairs (47). The sequence of the cDNA clone was verified and the PCR product was used as a probe to isolate multiple independent overlapping clones from the cDNA library. A full length clone containing the entire coding sequence was identified (SM38-native; Accession # AY826981). The nucleotide and amino acid sequence for the *S. mansoni* SM38 was used in a BLAST search to identify the *S. japonicum* SM38 orthologue (Accession # AY222890, ref. Hu et al., 2003, *Nat Genet.* 35:139-147).

9.1.2. SM38 Sequence Comparisons and Structural Modeling

The amino acid sequence of *S. mansoni* SM38 was aligned with the reported sequences for members of the cyclase family (Accession numbers: NM_007646 (mouse CD38), NM_013127 (rat CD38), AF272974 (rabbit CD38), NM_001775 (human CD38), AF117714 (canine CD38), NM_175798 (bovine CD38), NM_009763 (mouse CD157), NM_030848 (rat CD157), NM_004334 (human CD157), AY222890 (*S. japonicum* SM38), D38536 (*A. kurodai* cyclase) and M85206 (*A. californica* cyclase) using the CLUSTAL W multiple sequence alignment program (http://www.ebi.ac.uk/clustalw/) (Higgins et al., 1996, *Methods Enzymol* 266:383-402). The phylogram analysis comparing the relatedness of *S. mansoni* SM38 with all other known cyclase family members was performed with an evolutionary relationship program (http://www.ebi.ac.uk/clustalw/). The three dimensional structure of SM38 was obtained by homology modeling based on the crystallographic coordinates of both *Aplysia* ADP-ribosyl cyclase (PDB entry 1lbe) and human BST1/CD157 (PDB entry 1isf) using Modeller (Marti-Renom, et al., 2000, *Annu Rev Biophys Biomol Struct* 29: 291-325) and energy minimization using AMBER5.

9.1.3. SM38 Constructs

The primary nucleotide sequence of *S. mansoni* SM38 (SM38-native) was optimized for mammalian codon usage, resynthesized (GENEART, Regensburg, Germany) and then cloned into the mammalian expression vector pcDNA3.1 (referred to as SM38-opt). To facilitate immunoprecipitation and immunofluorescence analysis of SM38-opt, the 5' leader sequence of SM38-native (see FIG. 15 for sequence), identified by the SignalP (http://www.cbs.dtu.dk/services/SignalP/) (Bendtsen, et al., 2004, *J Mol Biol*, 340:783-795) and Phobius programs (http://pobius.binf.ku.dk/) (Kall et al., 2004, *J. Mol. Biol*, 338:1027-1036) was replaced with the mammalian CD8α leader sequence and a FLAG tag (ref. (Howard et al., 1993, *Science*, 262:1056-1059); construct referred to as CD8L/FLAG-SM38). To produce recombinant soluble SM38 in COS-7 cells, the GPI-anchor sequence, identified by the consensus sequence for the ω site (site of GPI attachment, see FIG. 15 for sequence; ref. Eisenhaber et al., 1998, *Protein Eng*, 11:1155-1161) was removed from CD8L/FLAG-SM38 (construct referred to as CD8L/FLAG-SM38ΔGPI). To produce soluble recombinant SM38 in yeast, the 5' leader sequence and the 3' GPI-anchor sequences were eliminated from SM38-opt and the remaining core ecto-domain sequence was cloned into the *Pichia pastoris* expression vector pPICZα A (Invitrogen, construct referred to as solSM38-Y). All constructs were sequenced to ensure that the insertions and truncations were present and that no artifacts had been introduced to the rest of the SM38 coding region during the cloning process.

9.1.4. Generation and Purification of Polyclonal Antiserum to SM38

C57BL/6J mice were bred and maintained in the Trudeau Institute Animal Breeding facility. All procedures involving animals were approved by the Trudeau Institute Institutional Animal Care and Use Committee and were conducted according to the principles outlined by the National Research Council. Mice were vaccinated on days 0, 28 and 56 using a Helios Gene Gun (Bio Rad) with 2.1 μm diameter gold bullets that were coated with the CD8L/FLAG-SM38 vector (1 μg/bullet) and the adjuvant vector, pBOOST-mIL-4/IL1β (0.25 μg/bullet, Invivogen). Serum was collected from vaccinated mice between days 10-14, 32-38 and 60-70. The antiserum was pooled and the IgG-containing fraction was enriched using Melon Gel IgG Spin Purification kit (Pierce).

9.1.5. SM38 Expression

To express SM38 in mammalian cells, COS-7 cells were transiently transfected with 30 μg of SM38-native, CD8L/FLAG-SM38 or CD8L/FLAG-SM38ΔGPI DNA per 10 cm plate using Lipofectamine 2000 (Gibco). At 72 h the conditioned media and/or cells were harvested from the plates and analyzed as described below. To express recombinant soluble SM38 in yeast, *Pichia pastoris* strain GS115 (Invitrogen) was electroporated (1.8 kV) with the linearized solSM38-Y construct and plated in medium containing zeocin (200 μg/ml). The selected transformants were grown in a shaking incubator in 100 ml BMGY (1% yeast extract, 2% peptone, 100 mM potassium phosphate buffer p 16.0, 1.34% yeast nitrogen base without aminoacids, 4×10⁻⁵% biotin, 1% glycerol) containing 1% Bacto casamino acids (Becton Dickinson) to inhibit the protease activity (54) at 30° C. until culture reached an $OD_{600}$=20. The cells were harvested by centrifugation at 1500×g for 5 min and resuspended in 50 ml induction medium BMMY (same composition as BMGY except that glycerol is replaced by 0.5% methanol). The induction was maintained for 48 h at 30° C. (100% methanol is added to 0.5% after 24 h). A high-expressing clone was selected and used for large-scale production.

9.1.5. Purification of Soluble Recombinant SM38

To purify soluble recombinant SM38 from CD8L/FLAG-SM38ΔGPI transfected COS-7 cells, the conditioned media was collected 72 h post-transfection, adjusted to a final concentration of 150 mM NaCl and then filtered through a 0.45 micron filter. The media was passed over an ANTI-FLAG M2-Agarose Affinity Gel column (Sigma, 0.25 ml final packed bed volume). The column was washed and FLAG-tagged SM38 was eluted with 200 µg/ml FLAG Peptide (Sigma) in 250 fractions. The fractions were pooled and concentrated using a 10K MWCO filter (Millipore). Protein concentration was determined with the Nano Drop ND-1000 Spectrophotometer (Nano Drop Technologies, Wilmington Del.) using BSA as a standard.

Recombinant SM38, secreted as a soluble protein in the supernatant of methanol-induced *Pichia pastoris*, was purified in a single step on a 1.2×4-cm Blue Sepharose 6 Fast Flow CL-6B column (Amersham Biosciences). After dialysis against 10 mM potassium phosphate buffer (pH 7.4), the media was loaded at 2 ml/min and the enzyme was eluted with a linear 0-1 M gradient of NaCl in the same buffer. This pseudo-affinity chromatography step is performed to ensure that a correctly folded enzyme is obtained. The protein concentration was determined by the BCA protein assay (Pierce) using BSA as a standard.

9.1.6. Silver Stain and Western Blot Analysis

Proteins were separated by electrophoresis under reducing conditions on 10% SDS-PAGE gels with a 4% stacking gel. Gels were either transferred to PVDF-Plus (Osmonics) for western blot analysis or were fixed, washed and stained with GelCode SilverSNAP Silver Stain Kit (Pierce). Western blot membranes were blocked with 5% BSA, incubated with biotinylated anti-FLAG (Sigma, 0.5 µg/ml) or anti-SM38 antiserum (1:2000 dilution) at 4° C. for 1.5 h, washed and then incubated with either strepAvidin-HRP (Southern Biotechnology) or anti-mouse Ig (Jackson Immunoresearch) for 1.5 h. Blots were developed using either fast or slow-developing chemiluminescence kits (Amersham).

9.1.7. Immunoflourescence Analysis

COS-7 cells were transiently transfected in Lab Tek slide chambers (Nunc) with CD8L/FLAG-SM38 or an empty vector control. At 72 h post-transfection, the cells were fixed with 4% paraformaldehyde for 5 min and then washed and blocked in dPBS containing 5% BSA. To detect SM38 using the mouse anti-SM38 antiserum, slides were stained with anti-SM38 (1:750 dilution) or normal mouse serum (1:750), washed and then stained with donkey anti-mouse IgG-Alexa-594 (Molecular Probes). To detect the FLAG tag of CD8L/FLAG-SM38, slides were incubated with avidin/biotin block (Vector), stained with biotinylated mouse anti-FLAG Ab (Sigma), washed and then developed with strepavidin-Alexa-594 (Molecular Probes). All slides were counterstained with DAPI mount (Molecular Probes) and viewed with a Zeiss Axioplan 2 microscope (Oberkochen, Germany) under brightfield and fluorescence using a 560/40 bandpass filter to view Alexa-594 and 330/80 bandpass filter to view DAPI. Images were captured at 40× original magnification with a Zeiss AxioCam digital camera and were overlayed using the Zeiss proprietary software, Axiovision 3.0.6.0.

9.1.8. Localization of SM38 in *S. mansoni* Parasites

Cryosections of adult worms were stained with affinity-purified IgGs isolated from anti-SM38 mouse serum (5 µg/ml) or purified normal mouse IgG. After washing, the sections were then stained with biotinylated secondary anti-mouse IgG (5 µg/ml; Jackson Immunoresearch) washed and then stained with the far-red fluorophore, AlexaFluor 647-conjugated streptavidin (5 µg/ml; Molecular Probes). Live and acetone-fixed parasites (adult worms and mechanically transformed schistosomules; 3 h old) were whole-mounted and stained with anti-SM38 IgG as described for the cryosections. Cyrosections and whole mount parasites were examined using a Bio-Rad MRC-1024 confocal microscope equipped with Krypton-Argon laser and 522 nm and 650 nm filters. SM38 was visualized with AlexaFluor 647 which emits at a maximum wavelength of 647 nm, where autofluorescence produced by phenolic compounds in schistosome sections is not detected. The fluorescent three-dimensional structures of whole mount adult worms were reassembled from the sub-micron laser sections using a voxel-based three-dimensional (3-D) imaging program (Voxx, v. 2, 55).

9.1.9. Flourometric Enzyme Assays $NAD^+$ glycohydrolase activity was assayed fluorometrically using $1,N^6$-etheno-$NAD^+$ (s-$NAD^+$, Sigma) as previously described (Muller, et al., 1983, *Biochem. J.*, 212:459-464). Briefly, aliquots of cell lysates, conditioned media, purified SM38 protein (25-200 ng), SM38 immunoprecipitated on sepharose beads (25 µl beads) or live *S. mansoni* worms (10 worms/assay) were suspended in HBSS in 96 well black microplates (Corning) in the presence of 40-400 µM ε-$NAD^+$ (100 µl final volume) at 37° C. in a SpectraMAX GeminiXS fluorescence plate reader (Molecular Devices, Sunnyvale Calif.). The fluorescence emission at 410 nm (excitation at 300 nm) of the fluorescent product s-ADPR was then followed for the next 30 min. Data is represented in relative fluorescence units (RFU) after blanking at time 0. The GDP-ribosyl cyclase activity was assayed similarly using $NGD^+$ (Sigma, 80-800 µM) as the substrate (Graeff, et al., 1994, *J. Biol. Chem.*, 269:30260-30267) and following the appearance of the fluorescent product cyclic GDP-ribose (emission 410 nm, excitation 310 nm).

The ADP-ribosyl cyclase activity was measured essentially as previously described (Graeff, et al., 2002, *Biochem J* 361:379-384) using a cycling assay. The enzyme was incubated with $NAD^+$ (200 µM) in buffer A (1 ml final volume) until the reaction reached 50% completion. The enzyme was eliminated by centrifugation for 10 min at 5000×g on ultra-filtration units (Vivaspin 2, Vivascience). The contaminating nucleotides were removed (overnight incubation at 37° C. in the presence of nucleotide pyrophosphatase, alkaline phosphatase and $NAD^+$ glycohydrolase followed by elimination of the three enzymes on ultrafiltration units) and the quantity of cADPR formed was then estimated using the cycling assay. Briefly, the conversion of the cADPR present in the samples into $NAD^+$ was performed by incubating the sample 1 h at room temperature with 0.1 µg/ml *Aplysia californica* ADP-ribosyl cyclase and 10 mM nicotinamide in 100 mM sodium phosphate buffer, pH 8.0. The cycling reaction was then allowed to proceed in the same buffer in the presence of 0.8% ethanol, 10 mM nicotinamide, 40 µg/ml BSA, 20 µg/ml diaphorase (treated with charcoal), 20 µg/ml alcohol dehydrogenase, 10 µM FMN and 20 µM resazurin. The increase in resorufin fluorescence (excitation at 544 nm and emission at 590 nm) was measured every minute for 2 h using a fluorescence plate reader (FluoStar from BMG Labtechnologies Inc).

9.1.10. Non-Flourometric Enzyme Assays

All three activities of SM38 were measured using recombinant enzyme purified from *Pichia pastoris*. The $NAD^+$ glycohydrolase activity was measured under saturating (420 μM) or limiting (25 μM) amounts of $NAD^+$ in the presence of [adenosine-U-$^{14}$C]$NAD^+$ (2.5×10$^5$ dpm) as previously described (Lund, et al., 1999, *J. Immunol.*, 162:2693-2702). The enzyme was suspended in 10 mM potassium phosphate buffer, pH 7.4 (buffer A) and incubated at 37° C. with substrate (200 μl final volume). At selected times, aliquots (50 μl) were removed and enzyme activity was stopped by adding ice-cold perchloric acid (2% final concentration). After neutralization with 3.5 M $K_2CO_3$, precipitated proteins were removed by centrifugation. Product formation was then monitored by HPLC as described below. The same experimental conditions were used with $NGD^+$ to assay both $NGD^+$ glycohydrolase and GDP-ribosyl cyclase activities. Product formation was then monitored by HPLC on a $C_{18}$ column as described below.

The cADPR hydrolase activity was measured by incubating cADPR (20 μM) at 37° C. in buffer A in the presence of enzyme (200 μl reaction volume). Aliquots were removed at different time points, treated as described above and analyzed by HPLC on a $C_{18}$ column.

The transglycosidation of $NADP^+$ was measured by incubating recombinant soluble SM38 with 1 mM $NADP^+$ and 20 to 40 mM nicotinic acid at 37° C. for 20 min in a 10 mM potassium phosphate buffer, pH 6.0 or 7.4 (final volume 500 μl). The reaction mixture was analyzed by HPLC on an ion-exchange column (see below). HPLC analysis of the reaction products were performed on aliquots on a $C_{18}$ column (see below).

9.1.11. Analysis Of Reaction Products by HPLC

Product analysis was performed by HPLC on 300×3.9 mm μBondapack $C_{18}$ column (Waters Assoc., Milford Mass.). The compounds were eluted isocratically at a flow rate of 1 ml/min with a 10 mM ammonium phosphate buffer, pH 5.5, containing 0.8-1.2% (v/v) acetonitrile and detected by radio-detection (Flo-one, Packard Radiometric Instruments, Meriden Conn.) when using [$^{14}$C]$NAD^+$ or by absorbance recordings at 260 nm. The formation of $NAADP^+$ was assessed by analysis on 150×4.6 mm AG MP-1 column (Interchrom) using a Shimadzu HPLC system. The elution was performed at a flow rate of 1 ml/min with a non-linear gradient starting with 100% solvent A (water). The percentage of solvent B (1.5% TFA) was linearly increased to 1% in 2 min, 2% in 4 min, 4% in 9 min, 8% in 13 min, 16% in 17 min, 32% in 21 min, 100% in 25 min and maintained at 100% for 10 min. Peaks were identified by comparison with authentic samples and areas obtained from UV recordings were normalized using the molar extinction coefficients of the reaction products.

9.1.12. Enzyme Kinetics

The assays were conducted at 37° C. in buffer A in the presence of soluble recombinant enzyme using eight different substrate concentrations. Reaction progress was obtained either by HPLC analysis of aliquots removed at given times or, alternatively, in the case of $NGD^+$, by monitoring the change of fluorescence at 410 nm ($\lambda_{exc}$=310 nm). Kinetic parameters were determined from the plots of the initial rates as a function of substrate concentration, according to Michaelis-Menten kinetics, using a non-linear regression program (GraphPad, Prism).

9.1.13. Preparation of Cell and Worm Lysates and Membrane Microsomes

COS-7 cells were transiently transfected with CD8L/FLAG-SM38, CD8L/FLAG-SM38ΔGPI or empty vector for 72 h. Cells were collected, washed in dPBS and frozen until used. Adult *S. mansoni* worm pairs were collected from the portal vein of 45 day infected golden hamsters, washed in dPBS and frozen. COS-7 cell pellets and worm pellets were lysed in 10 mM Tris/HCl (pH 7.3), 0.4 mM EDTA, protease inhibitors and 1% Triton X-100 (v/v) and detergent-soluble proteins were collected. In some experiments, the total lysates were used to analyze SM38 enzyme activity while in other experiments, SM38 was immunoprecipitated from the lysates using either Anti-FLAG sepharose beads or protein G beads coated with anti-SM38 antiserum.

To prepare membrane fractions from adult *S. mansoni* worms, 2 g of worms were disrupted at 4° C. with a potter in 10 mM potassium phosphate buffer (pH 7.4) containing 1 mM EDTA and 0.1 mM phenylmethylsulfonyl fluoride (PMSF) as protease inhibitors. The homogenate was centrifuged at 10,000×g for 15 min and the post-mitochondrial supernatant was centrifuged at 100,000×g for 60 min to obtain the membrane microsomal fraction. The membrane fraction was resuspended in 2 ml 10 mM potassium phosphate buffer (pH 7.4).

9.1.14. Phospholipase C Treatment

To cleave GPI-anchored proteins from transiently transfected COS-7 cells, the cells were washed with HBSS at 48 h post-transfection and then resuspended in HBSS in the presence or absence of 0.2 U phosphatidylinositol-specific phospholipase C (PI-PLC from *Bacillus cereus*, Sigma) at 37° C. for 2 h. The media was removed and assayed for $NAD^+$ glycohydrolase activity using ε-$NAD^+$ as a substrate. To cleave GPI-anchored proteins from *S. mansoni* membrane microsome fractions, 200 μl of the microsomes were incubated in the presence or absence of 1 U of PI-PLC for 2 h at 30° C. The fractions were then centrifuged at 100,000×g for 60 min and the supernatant and microsomes were tested for $NAD^+$ glycohydrolase and $NGD^+$ cyclase activity as described above. To cleave GM-anchored proteins from *S. mansoni* adult worms, 10 live worms were suspended in 200 μl HBSS in the presence or absence of 0.4 U PI-PLC at 37° C. for 2 h. The media was collected and assayed for $NAD^+$ glycohydrolase activity, GDP-ribosyl cyclase activity and pyrophosphatase activity as described above. Alternatively, the media was electrophoresed on an SDS-PAGE gel and analyzed by silver staining or western blot with the anti-SM38 Ab as described above.

9.1.15. Endoglycosidase Treatment

CD8L/FLAG-SM38 (70 ng) was incubated in 50 mM $NaH_2PO_4$ (pH 5.5) in the presence or absence of 0.05 U Endoglycosidase F1 (Sigma) for 1.5 h. The treated and untreated protein samples were then analyzed by SDS-PAGE and silver staining.

9.1.16. SM38 mRNA Transcription Analysis

Analysis of SM38 mRNA levels in different developmental stages was performed by semi-quantitative RT-PCR as previously described (Osman et al., 2004, *J. Biol. Chem.*, 269:6474-6486). Briefly, total RNA was extracted from different developmental stages, representing growth in both mammalian and molluscan hosts, using TRIzol reagent (Invitrogen). All RNA samples were reverse transcribed using a random decamer, and SuperScript Reverse Transcriptase II (SSRTaseII; Invitrogen) following vendor's recommended conditions. Complementary DNA (cDNA) samples were then used as templates in PCR reactions using specific primers for SM38 (fwd primer corresponding to by 536-562; rev primer complementary sequence of by 836-862 of the SM38 cDNA, yielding 327 by PCR product). PCR reactions were separated by electrophoresis in 2% agarose gels, ethidium bromide-stained and analyzed using gel-documentation system (GelDoc 1000; Bio-Rad) and quantified using Quantity One software (version 4.2.3; Bio-Rad). A negative control reaction consisting of reverse transcription reaction mix of adult worm pair total RNA but lacking SSRTaseII (—RT control) was also included. Specific primers for S. mansoni α-tublin gene (GenBank Accession #: M80214; by 424-444 and the complementary sequence of by 777-801 as forward and reverse primers, respectively, yielding 378 by PCR product) were used to amplify a PCR product that served as a constitutively transcribed control and was used to adjust the input amounts of cDNA templates in PCR reactions of different developmental stages. In order to ensure that the amplification products were analyzed in the exponential phase and below saturation limits (PCR plateau), the number of PCR cycles was also varied. Twenty-four cycles were used for α-tubulin while 26 cycles were used to amplify SM38 PCR products. All variables were considered and compensated for in data analysis.

9.2. Results

9.2.1. Platyhelminthes Express a Novel Member of the ADP-Ribosyl Cyclase Family The mammalian cyclase, CD38, plays an important functional role in regulating $Ca^{2+}$ signaling in a variety of cell types (Lee, H. C., 2004, *Curr. Mol. Med.*, 4:227-237). To identify other members of the cyclase family, the published consensus sequence for ADP-ribosyl cyclases (Prasad, et al., 1996, *Nature Struc. Biol.*, 3:957-964) was used to search the public DNA and protein data-bases. A single 330 by EST (Accession # AW017229) that was 27% similar at the amino acid level to the consensus cyclase sequence (Prasad, et al., 1996, *Nature Struc. Biol.*, 3:957-964) was identified. The EST identified was isolated from *Schistosoma mansoni*, a member of the phylum Platyhelminthes. To obtain the complete cDNA, PCR primers within the EST were designed and were used to amplify the sequence from a *S. mansoni* cDNA library. The PCR fragment was then used to probe the *S. mansoni* cDNA library and identify a full-length clone of 1034 bp containing a 303 amino acid open reading frame giving rise to a protein with a predicted molecular weight of 36 kDa (FIG. 13A). As shown in FIG. 13B, the open reading frame for the novel *S. mansoni* gene encoded a protein that is 21% identical to the human cyclases CD38 and CD157 (37% and 38% similarity respectively), and 24% identical to the *A. californica* cyclase (39% similarity). The critical cysteine residues necessary for the 5 conserved intra-disulfide bonds found in most cyclases (Prasad, et al., 1996, *Nature Struc. Biol.*, 3:957-964) are present in the novel *S. mansoni* sequence (FIG. 13B). Likewise, the crucial catalytic glutamate (E202) found deep within the nicotinamide binding pocket of all known cyclases (Munshi et al., 2000, *J. Biol. Chem.* 275:21566-21571) as well as a substrate-binding tryptophan residue (W165) that lines the rim of the nicotinamide-binding pocket of cyclases (Munshi et al., 2000, *J. Biol. Chem.* 275:21566-21571) are both conserved in the novel *S. mansoni* protein (FIG. 13B). Finally, the novel *S. mansoni* protein has a high degree of similarity (47%) to the other cyclase family members within the "TLED signature domain" (Munshi et al., 2000, *J. Biol. Chem.* 275:21566-21571) that contains residues which localize to the active site pocket (FIG. 13B).

The nucleotide and amino acid sequence from SM38 was then used to search the public data-bases to identify any potential SM38 orthologues. During the time between our two data-base searches, a transcriptosome analysis for the related trematode, *Schistosoma japonicum*, was published and a clone with significant homology to SM38 and the mammalian cyclase CD38 was reported (Accession # AY222890, ref. Hu, et al., 2003, *Nat Genet*, 35:139-147). In fact, the degree of identity between the amino acid sequence of *S. mansoni* SM38 and *S. japonicum* SM38 was greater than 56% and the sequences were 74% similar (FIG. 15), suggesting that this protein likely represents the *S. japonicum* SM38 orthologue. Next, two SM38 sequences were compared to all of the other cyclase family members in order to generate a phylogram. As shown in FIG. 13A, SM38 is most closely related to the *Aplysia* cyclases and then to the mammalian cyclase CD157. Since the three dimensional structures for both the *Aplysia* cyclase and CD157 have been previously published (Prasad, et al., 1996, *Nature Struc. Biol.*, 3:957-964, Yamamoto-Katayama, et al., 2002, *J. Mol. Biol.*, 316: 711-723), these structures were used to model, by homology, the structure of SM38 and its putative active site. As shown in FIG. 13B, the modeled structure for SM38 was very similar to that of CD157, particularly within substrate-binding groove. The model also demonstrates that the highly conserved residues found within the active site of all of the known cyclases, including the catalytic $Glu^{202}$), the $Glu^{124}$ of the "signature domain" that regulates hydrolase activity (Graeff, et al., 2001, *J Biol. Chem.* 276:12169-12173), and the $Trp^{165}$ that influences substrate positioning (Munshi et al., 2000, *J. Biol. Chem.* 275:21566-21571) are localized within the active site pocket of SM38 (FIG. 13C). At odds with the other cyclases, *S. mansoni* SM38 has a histidine residue at position 103, while the equivalent position in all other known cyclases is invariably occupied by tryptophan, a residue that plays a role in substrate binding within the active site (Munshi et al., 2000, *J. Biol. Chem.* 275:21566-21571). Interestingly, the histidine residue in *S. mansoni* SM38 is also located within the active site groove of our model (FIG. 13C) and is conserved in *S. japonicum* SM38 (FIG. 15). Taken together, the data indicate that SM38 is found in at least two members of the Platyhelminthes phylum, that the amino acid sequence of SM38 shares a significant degree of homology with other cyclase family members and that the predicted structure of the SM38 protein is strikingly similar to the other cyclase family members.

9.2.2. Recombinant SM38 is a GPI-Anchored Membrane $NAD^+$ Glycohydrolase

To determine whether SM38 is a functional enzyme, a heterologous (mammalian) in vitro expression system for SM38 was developed. Since preferred codon usage between Platyhelminthes and mammals is quite different, the *S. mansoni* SM38 cDNA was re-synthesized to facilitate translation in mammalian cells (SM38-opt). SM38-opt was then transiently expressed in COS-7 cells and the $NAD^+$ glycohydrolase (NADase) activity in the supernatant or cell lysates was determined by measuring the hydrolysis of $1,N^6$-etheno-$NAD^+$ ($\epsilon$-$NAD^+$). Hydrolysis of $\epsilon$-$NAD^+$ by cyclase family members results in the generation of fluorescent $\epsilon$-ADPR that can easily be detected using a spectrofluorimeter (Muller et al., 1983, *Biochem. J.*, 212:459-464). NADase activity was measured in the supernatant of the transfected cells since analysis of the SM38 sequence using different protein structure prediction programs (Bendtsen, et al., 2004, *J. Mol. Biol.*, 340:783-795; Kall et al., 2004, *J. Mol. Biol.*, 338:1027-1036) indicated that SM38 had a signal sequence (FIG. 15) but no obvious transmembrane domain and would therefore be secreted. However, NADase activity in the transfected cell supernatants was not detected (FIG. 19A). to determine whether SM38 was secreted, transiently transfected cells were lysed in 1% Triton X-100 and then NADase activity in the cell lysate was measured. Interestingly, abundant NADase activity in the lysate of COS-7 cells transfected with SM38-opt was detected (FIG. 19A), but no activity in cells transfected with the empty expression vector was observed (data not shown). These results strongly indicate that SM38 is expressed as either a transmembrane or cytosolic protein.

To determine the subcellular localization of SM38, it was necessary to directly visualize SM38 within cells. To facilitate this, the 5' signal sequence of SM38-opt was replaced with a mammalian signal sequence (CD8α leader) followed by a FLAG tag (CD8/FLAG-SM38). To assess whether the FLAG-tagged recombinant protein could be detected and purified with anti-FLAG reagents, COS-7 cells were transiently transfected with the CD8L/FLAG-SM38 construct. The cells were lysed in detergent and SM38 was purified over an anti-FLAG affinity column. The FLAG-tagged SM38 was eluted, the purified protein was separated on SDS-PAGE, and then a western blot was performed using an anti-FLAG antibody. A protein of approximately 48 kD was detected in transfected cell lysates (FIG. 19B). Next, to determine where SM38 was localized in the transfected cells, COS-7 cells were transiently transfected with the CD8L/FLAG-SM38 construct and then a biotinylated anti-FLAG antibody was used to perform immunofluorescence analysis. As shown in FIG. 2C, the plasma membrane of COS-7 cells that were transfected with CD8L/FLAG-SM38 specifically stained with the anti-FLAG antibody, while no staining was observed in cells that were transfected with an empty expression vector (FIG. 19D). Therefore, these data indicate that SM38, at least when expressed in mammalian cells, is membrane-associated.

SM38 was not predicted to have a transmembrane domain by any of the commonly used protein structure prediction programs. However, CD157, the closest mammalian relative of SM38, is a membrane-associated GPI-anchored protein. Therefore, the 3' amino acid sequence of SM38 was re-examined to see if a GPI anchor motif could be identified. Although the SM38 3' sequence did not conform with most of the motifs that have been described for mammalian GPI anchors (Eisenhaber, et al., 2003 *Bioessays* 25; 367-385), a potential GPI-anchor site was identified (ω-site, see FIG. 15) with the help of an algorithm written by Eisenhaber et. al. (Eisenhaber, et al., 1998 *Protein Eng.* 11; 1155-1161). To determine whether SM38 is GPI anchored, it was tested whether SM38 can be cleaved from the membrane of CD8L/FLAG-SM38 transfected COS-7 cells by Phosphotidyl inositol-specific Phospholipase C (PI-PLC), a GPI-anchor lipase. The media from transfected and non-transfected COS-7 cells was removed, the cells were washed, and then the cells were incubated in the presence or absence of PI-PLC. The supernatant was collected 2 hours later and NADase activity was measured using ε-NAD⁺ as a substrate. As expected, NADase activity was not detected in the supernatant of cells transfected with the empty vector, regardless of whether PI-PLC was added (FIG. 19E). Likewise, no activity in the supernatant of cells transfected with CD8L/FLAG-SM38 and incubated in media alone was detected (FIG. 19E). In contrast, abundant NADase activity was observed in the supernatant collected from the CD8L/FLAG-SM38 transfected cells that were incubated with PI-PLC (FIG. 19E). Identical results were observed when the experiment was performed using COS-7 cells transfected with the original native form of SM38. Thus, SM38, like CD157, is expressed as a GPI-anchored membrane-associated protein in mammalian cells.

9.2.3. SM38 is a Multifunctional Enzyme

Cyclases are multi-functional enzymes that catalyze several reactions including the hydrolysis of NAD⁺ to produce ADPR (NAD⁺ glycohydrolase activity), the cyclization of NAD⁺ into cADPR (ADP-ribosyl cyclase activity), the hydrolytic conversion of cADPR into ADPR (cADPR hydrolase activity) and the transglycosidation of NADP⁺ (Eisenhaber, et al., 2003 *Bioessays* 25; 367-385). To better characterize the enzymatic properties of SM38, a secreted soluble form of the SM38 ecto-domain by deleting the GPI-anchor motif was produced (see FIG. 15) in a FLAG-tagged SM38 construct (CD8L/FLAG-SM38ΔGPI). COS-7 cells were transiently transfected with the new construct, and the supernatant was collected after 72 h. NADase activity in the supernatant and in the cell lysate was measured using ε-NAD⁺ as a substrate. As expected, the enzyme activity was now highly enriched in the supernatant fraction and was found at only very low levels in the cell lysates (FIG. 20A). Next, the secreted SM38 protein was purified from the supernatant on an anti-FLAG column and, as expected, affinity purification of SM38 resulted in significant enrichment of the NADase activity (FIG. 20A, inset). The affinity purified soluble SM38 was then analyzed by SDS-PAGE and silver-staining and two protein species of 43 and 46 kD were observed (FIG. 20B). To ensure that both of the eluted proteins were bona fide SM38, western blot analysis using an anti-FLAG antibody was performed. As shown in FIG. 20B, both protein species were recognized by the anti-FLAG antibody.

Since two protein forms for SM38 were identified and both forms were considerably larger than the predicted molecular weight of soluble SM38 (~30 kDa) the possibility that SM38 might be glycosylated was considered, particularly since the SM38 sequence contained 4 potential N-linked glycosylation sites (FIG. 15). Therefore, the purified recombinant SM38 was treated with Endoglycosidase F1 (Endo-F) to cleave N-linked sugars and the molecular weight of the treated proteins was then determined. Treatment of SM38 with Endo-F reduced the size of both forms of SM38 by about 2 kD to 44 and 41 kD (FIG. 20B). Thus, soluble recombinant SM38 is expressed in two isoforms, both of which are glycosylated.

Although SM38-specific NADase activity was easily detected using ε-NAD⁺ as a substrate and measuring product formation fluorimetrically (i.e., FIG. 20A), larger quantities of soluble SM38 were needed to better characterize the catalytic properties of SM38. Therefore, the production and purification of soluble SM38 was scaled up using a *Pichia pastoris* expression system and an affinity gel purification scheme routinely employed to purify other cyclases and NAD⁺ glycohydrolases (Cakir-Keifer, et al., 2000 *Biochem. J.* 349; 203-210). Similar to what was observed using the mammalian expression system (FIG. 20B), it was found that soluble SM38 is expressed in *Pichia* in two isoforms of 43 and 44 kD (FIG. 20C). The NAD⁺ glycohydrolase activity of the purified SM38 was then determined by incubating the recombinant enzyme with saturating amounts of radio-labeled NAD⁺ and analyzing product formation by HPLC (FIG. 20D). As indicated in Table II, the specific activity of SM38 was calculated to be 13.2 μmol/min/mg of SM38 protein; a value that is in the same range as that reported for mammalian cyclases such as CD38 (Howard, et al., 1993 *Science* 262; 1056-1059; Cakir-Keifer, et al., 2000 *Biochem. J.* 349; 203-210).

TABLE II

Kinetic parameters for the transformation of substrates by SM38[a]

| Substrate | $K_m$ µM | $V_{max}$ µmol/min/mg | $k_{cat}$ s$^{-1}$ | $k_{cat}/K_m$ M$^{-1}$s$^{-1}$ |
|---|---|---|---|---|
| NAD$^+$ | 38.5 ± 6.8 | 13.2 ± 2.6 | 6.51 ± 1.28 | 1.69 × 10$^5$ |
| NGD$^+$ | 23.4 ± 1.1 | 4.8 ± 0.1 | 2.37 ± 0.05 | 1.01 × 10$^5$ |
| NADP$^+$ | 13.7 ± 2.9 | 39.2 ± 1.6 | 19.34 ± 0.79 | 14.12 × 10$^5$ |

[a]All reactions were performed at 37° C. in 10 mM potassium phosphate buffer (pH 7.4) in the presence of purified recombinant SM38 produced in *Pichia pastoris*.

Interestingly, using HPLC to measure product formation, ADPR was easily visualized but measurable cADPR was not detected (FIG. 21D), despite varying the pH of the assay between 5.0-8.0 (data not shown). Since the amount of cADPR produced by SM38 was less than the limit of detection by HPLC, (i.e. <1% of the radio-labeled reaction products), a very sensitive cycling assay (Graeff, et al., 2002 *Biochem. J.* 361; 379-38) was next used to measure cADPR production by recombinant soluble SM38. Although cADPR was detect rf by this method, the amount produced under steady-state conditions was very small and represented only 0.016% of the total reaction product ADPR.

These data indicate that SM38 is either a much more efficient NAD$^+$ glycohydrolase than ADP-ribosyl cyclase or that the produced cADPR is rapidly hydrolyzed by SM38 to ADPR (cADPR hydrolase activity). To distinguish between these possibilities, the cADPR hydrolase activity of SM38 was measured. It was found that SM38 is a very poor cADPR hydrolase with an activity of less than 6 nmol/min/mg protein, which is 3 orders of magnitude less than the NAD$^+$ glycohydrolase activity of SM38 (Table II). Therefore, it seemed unlikely that SM38 was degrading the cADPR as rapidly as it produced it and more likely that SM38 produces very lithe cADPR under steady-state conditions. To specifically test whether SM38 is competent to catalyze a cyclase reaction, the purified enzyme was incubated with NGD$^+$, an analogue of NAD$^+$, which is efficiently converted to cyclic GDP-ribose (cGDPR) by many of the mammalian cyclase family members and is easily detected fluorometrically (Graeff, et al., 1994 *J. Biol. Chem.* 269; 30260-30267). NGD$^+$ proved to be an excellent substrate for SM38 ($K_m$=23.4 µM, Table II) and as shown in FIG. 20E was quite efficiently cyclized. The cyclization/hydrolysis ratio was approximately 6.0 (FIG. 20E), and the specific activity under steady state conditions was 4.8 µmol/min/mg protein (FIG. 20F, Table II); all of which are quite comparable to that reported for mammalian cyclases such as CD38 (Berthelier, et al., 1998 *Biochem J.* 330; 1383-1390). Thus, these data show that, while SM38 is a very inefficient ADP-ribosyl cyclase, this enzyme is mechanistically competent to catalyze the production of cyclic compounds such as cGDPR.

Next, whether SM38 was able to use NADP$^+$ as substrate and to catalyze a transglycosidation reaction in the presence of nicotinic acid was tested. As indicated in Table II, NADP$^+$ proved to be an excellent substrate of SM38 and, in terms of catalytic efficiency ($k_{cat}/K_m$), NADP$^+$ was an even better substrate than NAD$^+$ (8-fold better, see Table II). This is contrast with human CD38 for which NAD$^+$ was the favored substrate (Berthelier, et al., 1998 *Biochem J.* 330; 1383-1390). As shown by HPLC (FIG. 20G), the pyridine-base exchange reaction was readily catalyzed by SM38, at pH 6.0, indicating that this enzyme, like CD38 and the *Aplysia* cyclase, is able to synthesize the Ca$^{2+}$-mobilizing messenger NAADP$^+$. As noted before for the other members of the cyclase family, the formation of NAADP$^+$ was less efficient under neutral pH conditions compared to more acidic pH conditions (3-fold reduction in NAADP$^+$ formation at pH 7.4, compared to pH 6.0, data not shown).

In addition to catalyzing a base-exchange reaction using NADP$^+$ as the substrate, it was also found that SM38 can catalyze a base-exchange reaction using NAD$^+$ as the substrate in the presence of isoniazid (INH, not shown). This pyridine has been widely used to classify the mammalian NAD$^+$ glycohydrolases (Table III) into either 'INH-sensitive' (e.g. bovine CD38) or 'INH-insensitive' (e.g. human CD38) NADases (Zatman, et al., 1954 *J. Biol. Chem.* 209; 453-466) and SM38 appears to be a member of the latter category of NADases.

Finally, like the other members of the cyclase family, SM38 can catalyze the methanolysis of NAD$^+$ leading to the formation of β-methyl ADP-ribose (Table III). On a molar basis, methanol was found to react about 5-fold faster than water (H. M-S. and F. S. unpublished). Moreover, the presence of 1-3 M methanol did not affect the overall turnover rate of the NAD$^+$ solvolysis reactions (hydrolysis and methanolysis). These data are consistent with the cleavage of the nicotinamide-ribose bond being the rate-limiting step of the kinetic mechanism of SM38, again similar to what has been previously shown for other cyclase family members such as CD38 (Schuber, et al., 2004 *Curr. Mol. Med.* 4; 249-261; Cakir-Kiefer, et al., 2001 *Biochem J* 358; 399-406; Muller-Steffner, et al., 1994 *Bioch-Biophys. Res. Commun.* 204; 1279-1285). Taken altogether, the data indicate that the enzymatic properties of SM38 are similar to other members of the cyclase family, and that SM38, can catalyze the production of ADPR, NAADP$^+$, and to a lesser extent, cADPR.

TABLE III

Comparison of SM38 enzyme properties with cyclase family members

| Properties | SM38 | Mammalian cyclases | Aplysia cyclase |
|---|---|---|---|
| Hydrolysis of NAD$^+$ | yes | yes | very low |
| Formation of cADPR | very low | low | yes |
| Hydrolysis of cADPR | very low | yes | very low |
| Formation of cGDPR | yes | yes | yes |
| Transglycosidation | yes | yes | yes |
| Sensitivity to INH | no | yes/no | ND |
| Methanolysis of NAD$^+$ | yes | yes | very low |
| Inhibition by araF-NAD$^+$ | weak (IC$_{50}$ > 10 µM) | Ki nM range | weak (IC$_{50}$ > 10 µM) |

9.2.4. SM38 Expression is Developmentally Regulated in *S. mansoni*

To determine when and where SM38 is expressed during the life-cycle of *S. mansoni*, a semi-quantitative PCR approach with SM38-specific and *S. mansoni* α-tubulin specific primers was used to determine when SM38 mRNA transcripts are expressed during schistosome development. SM38 transcripts were not detectable in *S. mansoni* eggs or in uninfected *Biomphalaria glabrata* snails (intermediate hosts) but were easily observed in the *S. mansoni*-infected snails (FIG. 21A). SM38 expression then declined to undetectable levels in the *S. mansoni* cercariae, schistosomules and in immature day 21 worm pairs (FIG. 21A-B). In contrast, SM38 expression was dramatically increased in day 28 and day 35 worm pairs, coinciding with male-female worm pairing, and was then maintained in both male and female mature adult worm pairs (FIG. 21A-B). Together, these data indicate that SM38 plays a developmentally regulated signaling function in *S. mansoni* in both intermediate and definitive hosts.

9.2.5. SM38 is Expressed as a Constitutively Active Ecto-Enzyme in the Tegument Membrane of Adult *S. mansoni*

To evaluate whether SM38 protein is expressed and functional in adult *S. mansoni* worms membrane and cytosolic fractions from homogenized adult worms was purified and NAD$^+$ glycohydrolase activity was assessed using radio-labeled NAD$^+$ as a substrate. Identical to our results using the heterologous mammalian expression system, NAD$^+$ glycohydrolase activity was observed exclusively in the membrane microsome fraction of the adult *S. mansoni* worms. In addition, despite using radio-labeled NAD$^+$ as the substrate, only the formation of ADPR was detected, while cADPR was not detected (FIG. 22A), indicating that the native enzyme, like the recombinant version, is a very inefficient ADP-ribosyl cyclase. To test whether the native SM38 could catalyze a cyclase reaction, membrane microsomes were incubated with NGD$^+$ and the cGDPR accumulation was measured fluorimetrically and by HPLC. As expected, the *S. mansoni* membrane fraction very efficiently catalyzed a cyclase reaction with a cGDPR/GDPR ratio of 12 (FIG. 22B). Next, to determine whether the membrane-associated NAD$^+$ glycohydrolase/NGD$^+$ cyclase expressed by adult *S. mansoni* worms was GPI-anchored, the microsomal fraction was incubated in the presence and absence of PI-PLC and then NAD$^+$ glycohydrolase activity released into the supernatant was measured. As expected, the Schistosome NAD$^+$ glycohydrolase was sensitive to PI-PLC (FIG. 22C). Together, these data indicate that the *Schistosoma* NAD$^+$ glycohydrolase is a membrane-associated GPI-anchored protein.

Schistosomes, like all flatworms, have an outer membrane, referred to as the tegument (66). The tegument is composed of a syncytium having a heptalaminar apical membrane and a basal membrane separated by 9 nM of cytoplasm connecting via a cytoplasmic bridge to subtegumental cytons. To assess whether the *Schistosoma* NAD$^+$ glycohydrolase is associated with the outer tegument membrane of the adult worm, live *Schistosoma* parasites were directly incubated with the membrane impermeant substrate $\epsilon$-NAD$^+$ and accumulation of fluorescent $\epsilon$-ADPR was measured. As shown in FIG. 22D, as few as 10 live *S. mansoni* adult worms were able to efficiently catalyze the NAD$^+$ glycohydrolase reactions, indicating that adult *S. mansoni* parasites express an enzyme(s) with the properties of SM38 on the outer tegument. To determine whether the NADase associated with the outer tegument of *S. mansoni* adult worms is GPI-anchored, 10 live parasites were incubated in the presence or absence of PI-PLC, the supernatant was collected after two hours and NAD$^+$ glycohydrolase activity was measured using $\epsilon$-NAD$^+$ as the substrate (FIG. 22E). Culture media from the worms that were incubated without PI-PLC was devoid of NADase activity, however NADase activity in the medium from the worms that were treated with PI-PLC was easily detected (FIG. 22E). Finally, to ensure that an authentic NAD$^+$ glycohydrolase on the outer tegument was being and not a pyrophosphatase (which can also utilize NAD$^+$ as a substrate), the PI-PLC treated supernatant was incubated with 1,N$^6$-etheno-PyAD$^+$, a substrate that is transformed by nucleotide pyrophosphatases into the fluorescent 1,N$^6$-etheno-AMP, but cannot be utilized by members of the cyclase family (Muller, et al., 1984 *Biochem J* 223; 715-721). No pyrophosphatase activity was detected (data not shown), thus the enzyme present on the outer tegument of adult worms is an authentic GPI-anchored NAD$^+$ glycohydrolase.

The data indicate that SM38 or a SM38-like enzyme is expressed as an outer tegument protein by adult *S. mansoni* worms. In order to directly test this hypothesis, SM38 specific antibodies were generated by immunizing and boosting mice with the CD8LFLAG-SM38ΔGPI expression construct. Serum was collected from the immunized mice and the specificity of the antiserum was assessed by western blot, immunofluorescence and immunoprecipitation. As shown in FIG. 23A, the anti-serum raised in response to the SM38 cDNA vaccine specifically recognized soluble recombinant SM38 protein by western blot but did not react with other purified proteins including ovalbumin and BSA (not shown). Next, to determine whether the anti-SM38 antiserum would specifically recognize membrane-associated SM38 protein, COS-7 cells were transiently transfected with CD8L/FLAG-SM38 or the empty expression vector and then the cells were stained with the anti-SM38 antiserum followed by a fluorochrome-conjugated anti-mouse immunoglobulin antibody. As expected, the anti-SM38 antiserum did not stain the empty vector-transfected cells (FIG. 23B) nor did normal mouse serum stain SM38-transfected cells (FIG. 23C). However, identical to what was observed when the SM38 transfected cells were stained with anti-FLAG antibody (see FIG. 19C), the anti-SM38 antiserum stained the plasma membrane of COS-7 cells transfected with CD8L/FLAG-SM38 (FIG. 23D).

To demonstrate that the anti-SM38 antiserum could be used to immunoprecipitate enzymatically active SM38 protein, COS-7 cells were transiently transfected with CD8L/FLAG-SM38 or the empty expression vector, the transfected cells were lysed in Triton X-100 and the detergent soluble proteins were collected. Immunoprecipitations were performed using the anti-SM38 antiserum or normal mouse serum coupled to protein G beads and then whether the immunoprecipitated proteins were able to catalyze the hydrolysis of $\epsilon$-NAD$^+$ was analyzed. No enzyme activity was observed in immunoprecipitates from control transfected cells regardless of whether normal mouse serum or anti-SM38 antiserum was used as the immunoprecipitating antibody (FIG. 23E). Likewise, no enzyme activity was detected in the immunoprecipitates using the normal mouse serum and lysates from the SM38-transfected cells (FIG. 23E). However, abundant NAD$^+$ hydrolase activity was detected in the immunoprecipitated proteins isolated from the SM38-transfected cells using the anti-SM38 antiserum (FIG. 23E). Together, these data indicate that the antiserum raised against the SM38 cDNA is specific for SM38 and recognizes enzymatically active membrane-anchored SM38 as well as denatured SM38.

To determine whether enzymatically active SM38 protein is expressed by adult *S. mansoni* worms, adult worms were lysed in Triton X-100, the proteins were collected and immunoprecipitations were performed using our anti-SM38 antiserum or normal mouse serum as a control. Whether the proteins precipitated from the adult worms were able to hydrolyze $\epsilon$-NAD$^+$ was then determined. As shown in FIG. 23F, the anti-SM38 immunoprecipitated proteins catalyzed a NAD$^+$ glycohydrolase reaction while the proteins that were immunoprecipitated with normal mouse serum had no detectable enzyme activity. Finally, to visualize the native SM38 protein expressed by adult *S. mansoni* worms, live worms were incubated in HBSS in the presence of PI-PLC. The proteins released into the culture media were collected and concentrated and then the proteins were analyzed by silver staining and western blot. As shown in FIG. 23G, a large number of proteins were either secreted or shed by the PI-PLC-treated adult worms. However, upon western blot analysis using our anti-SM38 antiserum, a single protein of approximately 43 kDa was detected (FIG. 23O). Interestingly, the native SM38 protein expressed by the adult *S. mansoni* worms was very similar in size to the soluble recombinant SM38 secreted by transfected COS-7 cells (FIG. 23G). Native SM38 was also detected a two similar-sized protein forms using anti-SM38 antibodies to probe western blots of extracts isolated from live worms treated with NP-40 to enrich for surface-associated proteins (FIG. 16). Taken together these data show that an antiserum raised against SM38, a novel protein encoded by a cDNA isolated from *S. mansoni* which shows significant homology to the $NAD^+$ glycohydrolase/ADP ribosyl cyclase family of enzymes, specifically recognizes a surface-associated GPI-anchored protein in adult *S. mansoni* worms that is capable of catalyzing $NAD^+$ glycohydrolase and $NGD^+$ cyclase reactions.

RT-PCR data and western blot experiments using anti-SM38 antibodies strongly indicated that SM38 is developmentally expressed as a membrane and tegument-associated protein in adult *S. mansoni* parasites. To confirm these findings, the IgG fraction of the anti-SM38 antiserum was used to detect the native SM38 protein in adult worm cryosections, whole mount worms and mechanically transformed schistosomules (3 h-old). SM38 protein was not detected in either live or acetone-fixed 3 h schistosomules (data not shown). Similarly, no specific fluorescence was observed in adult worm cryosections (FIG. 24C) or whole worms (FIG. 24G) when probed with pre-immune normal mouse IgG. In contrast, strong surface staining along the male gynecophoric canal (arrow; FIG. 24F) as well as fluorescence of the epithelial tissues surrounding the gut (not shown) could be seen in adult worm cryosections probed with anti-SM38 antibody. In addition, surface fluorescence was also detected in acetone-fixed (FIG. 24H) or live (FIG. 24I) whole worms probed with anti-SM38 antibodies. Specific staining was observed on the surface (tubercles, FIG. 24H), male gynecophoric canal (FIG. 24H) and oral and ventral suckers of male and female worms (FIG. 24H-I). Thus, these data indicate that in adult schistosomes SM38 is localized to the outer surface of the parasite. The implications of these results for potential SM38 vaccination and small molecule antagonist studies is discussed.

10. EXAMPLE

CD38 Deficient T Cells do not Induce Lung Inflammation after Allergen Challenge The subsection below demonstrates that CD38 expression on allergen-specific T cells (or autoimmune T cells) is required for either their maturation into differentiated effector cells or for their migration to sites of inflammation. The subsection also demonstrates that inflammatory responses in the lungs of allergen-challenged mice is dependent on CD38-expressing T cells.

10.1. Materials and Methods

Naïve T cell receptor (TCR) transgenic T cells specific for ovalbumin (OVA) were purified from the spleens and lymph nodes of normal transgenic mice (WT T cells) and CD38 deficient transgenic mice (KO T cells). Either KO or WT OVA-specific T cells (CD45.2$^+$) were then injected into congenic normal hosts (CD45.1$^+$) and the host animals were then sensitized with 10 μg NP-OVA (n=7 mice/group) or PBS administered (n=3 mice/group) intranasally once/day for the next 7 days. On day 8, the cells from the draining lymph node and the lung airways (Bronchial alveolar lavage, BAL) were collected, counted and analyzed by FACS.

10.2. Results

The number of donor OVA-specific T cells with an activated phenotype) (CD45.2$^+$ CD4$^+$ CD62L$^{lo}$) present in the lymph node and BAL of the sham and allergen-challenged host is depicted in FIG. 25. The number of infiltrating inflammatory cells to the lungs of the mice is indicated in FIG. 26. The CD38 deficient OVA-specific T cells are reduced in number in both the lymph node and in the lung at the site of inflammation. Similarly, the allergen-induced inflammatory response is suppressed in the lungs of the mice receiving CD38 deficient T cells. This deficiency in maturation/migration of T cells which lack CD38 results in a reduced inflammatory response in the lungs of allergen-challenged animals. Therefore, the data suggest that CD38 inhibitors will reduce T cell-mediated pathology at sites of inflammation such as the lung in asthma as well as inflamed tissues/joints etc. of patients suffering from autoimmune disease.

11. EXAMPLE

Priming Of Inflammatory Allergen Specific T Cells is Reduced in CD38 Deficient Mice, Even when the T Cells are from Normal Animals The subsection below demonstrates that CD38 expression on antigen-presenting cells is required for the expansion of allergen-specific T cells. The subsection also demonstrates that expression of CD38 on antigen-presenting cells promotes cellular inflammation in the airways and lung tissue of allergen challenged mice.

11.1. Materials and Methods

Naïve T cell receptor (TCR) transgenic T cells specific for ovalbumin (OVA) were purified from the spleens and lymph nodes of normal transgenic mice. The normal OVA-specific T cells (CD45.1$^+$) were then injected into congenic normal hosts (WT, CD45.2$^+$) or CD38 deficient hosts (KO, CD45.2$^+$). The host animals were then sensitized with 10 μg NP-OVA (n=7 mice/group) or PBS administered (n=3 mice/group) intranasally once/day for the next 7 days. On day 8, the cells from the draining lymph node and the lung airways (Bronchial alveolar lavage, BAL) were collected, counted and analyzed by FACS.

11.2. Results

The number of donor OVA-specific T cells (CD45.2$^+$ CD4$^+$) present in the lymph node and BAL of the sham and allergen-challenged host is depicted in FIG. 27. The number of activated CD62Llo donor T cells present in the lymph nodes is also shown in FIG. 27. The number of infiltrating inflammatory cells to the lungs of the mice is indicated in FIG. 28. A representative H&E section of the lungs of OVA challenged WT or CD38 KO mice is also depicted in FIG. 28. Expression of CD38 on antigen-presenting cells is required for the efficient priming, expansion and differentiation of allergen-specific T cells (even when the T cells are CD38 sufficient). The reduction in T cell priming observed in the CD38 deficient mice leads to reduced numbers of allergen-specific T cells that can induce an inflammatory response in the lung. Therefore, the data suggest that CD38 inhibitors will reduce the expansion of allergen-specific or autoreactive T cells, resulting in reduced T cell mediated pathology at sites of inflammation such as the lung in asthma as well as inflamed tissues/joints etc. of patients suffering from autoimmune disease.

12. EXAMPLE

Allergen-Induced Inflammatory Responses in the Lungs are Reduced in CD38 Deficient Mice The subsection below demonstrates that CD38 deficient mice are more resistant to allergen-induced inflammation in the lung.

12.1. Materials and Methods

CD38 deficient (KO) or normal C57BL/6 (WT) mice were primed with ovalbumin (OVA) in alum on day 0 (10 ug/mouse administered i.p.) or were inoculated with PBS. On day 42 post-immunization, animals were either left untreated (prime only) or were challenged with 10 μg OVA administered intranasally 1 time/day for the next 7 days (prime+challenge group and challenge only group). The lungs were isolated from all groups of mice one day after the last administration of OVA and were prepared for histological examination. H&E stained paraffin sections of a representative animal from each group are shown.

12.2. Results

The inflammatory cell infiltrate is significantly reduced in the lungs of the CD38 deficient mice that were primed and then challenged with OVA. Expression of CD38 on either hematopoietic cells or resident lung cells (epithelial, stromal or fibroblast) is required for the induction of an inflammatory response in the lungs of mice that have been primed and then sensitized with an allergen administered into the lung airways. Therefore, these data suggest that CD38 inhibitors will block the induction of allergic responses in patients and/or the chronic inflammation in the lungs of allergic or asthmatic patients.

13. EXAMPLE

Diabetes Onset is Delayed in CD38 Deficient Mice

13.1. Materials and Methods

CD38 deficient (KO) or normal BALB/c (WT) mice were injected with Streptozotocin (STZ; 50 mg/kg/mouse) 1 time/day for 5 consecutive days. Blood glucose levels were measured 10 and 17 days after the last STZ injection.

13.2. Results

The multi-low dose STZ treatment resulted in increased blood glucose levels in both WT and KO animals within 10 days of treatment. However, the hyperglycemia was significantly higher in the WT animals. By day 17, the majority of WT mice were diabetic (7/11 animals with blood glucose>350 mg/dl) while only a small fraction of the KO mice were diabetic (3/11 animals). CD38 expressing cells facilitate destruction of the pancreas in response to STZ treatment indicating that CD38 regulates immune-mediated inflammatory responses that cause the destruction of the pancreatic β-cells. Therefore, these data suggest that CD38 inhibitors could be used to either prevent or delay the onset of autoimmune mediated diabetes.

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Various publications are cited herein, the contents of which are hereby incorporated, by reference, in their entireties.

We claim:

1. An isolated SM38 polypeptide encoded by a nucleic acid molecule that binds over the full length to the complement nucleotide sequence of a nucleotide sequence that encodes:
   (i) the SM38 amino acid sequence of FIG. 13A (SEQ ID NO: 5);
   (ii) the SM38 amino acid sequence of FIG. 13A (SEQ ID NO: 5) having a deletion of one or more amino acids between 1-19;
   (iii) the SM38 amino acid sequence of FIG. 13A (SEQ ID NO: 5) having a deletion of one or more amino acids between 276-303; or
   (iv) the SM38 amino acid sequence of FIG. 13A (SEQ ID NO: 5) having a deletion of one or more amino acids between 1-19 and 276-303
wherein said binding takes place in 0.5 M NaHPO$_4$, 7% sodium dodecyl sulfate (SDS), 1 mM EDTA at 65° C., and washing in 0.1×SSC/0.1% SDS at 68° C.

2. The isolated SM38 polypeptide of claim 1 comprising:
   (i) the amino acid sequence of FIG. 13A (SEQ ID NO: 5);
   (ii) the amino acid sequence of FIG. 13A (SEQ ID NO: 5) having a deletion of one or more amino acids between 1-19;
   (iii) the amino acid sequence of FIG. 13A (SEQ ID NO: 5) having a deletion of one or more amino acids between 276-303; or
   (iv) the amino acid sequence of FIG. 13A (SEQ ID NO: 5) having a deletion of one or more amino acids between 1-19 and 276-303.

3. A pharmaceutical composition comprising the SM38polypeptide of claim 1, or polypeptide fragment thereof, and a pharmaceutically acceptable carrier.

4. The pharmaceutical composition of claim 3, further comprising an adjuvant, wherein the SM38 polypeptide, or polypeptide fragment thereof, stimulates an immune response.

5. A method for identifying a compound that inhibits the enzymatic activity of the SM38 polypeptide of claim 1 comprising (i) contacting SM38 with a test compound and substrate and measuring the level of SM38 activity, (ii) in a separate experiment, contacting SM38 and substrate and measuring the level of SM38 activity, where the conditions are essentially the same as in part (i) and then (iii) comparing the level of SM38 activity measured in part (i) with the level of SM38 activity in part (ii), wherein a decrease level of SM38 activity in the presence of the test compound indicates that the test compound is a SM38 inhibitor.

6. The method of claim 5 wherein the SM38 is a polypeptide expressed in a cell.

7. The method of claim 5 wherein the SM38 is a purified SM38polypeptide.

8. The method of claim 5 wherein the SM38 enzyme activity is selected from the group of enzyme activities consisting of NAD+ glycohydrolase, ADP-ribosyl cyclase and transglycosidation activity.

9. The method of claim 5 wherein the SM38 enzyme activity is measured by monitoring the rate of formation of nicotinamide, ADP-ribose (ADPR), cyclic-ADPR (cADPR), or nicotinic acid adenine dinucleotide phosphate (NAADP).

10. The method of claim 5 wherein the SM38 to be contacted in step (i) and (ii) with a test compound or vehicle control is provided in an array of locations.

11. An SM38 fusion polypeptide comprising the SM38polypeptide of claim 1.

12. The SM38 fusion polypeptide of claim 11, wherein the SM38 polypeptide of claim 1 is fused to (i) a polypeptide having enzymatic activity, (ii) a fluorescent protein, (iii) a polypeptide tag, or (iv) a luminescent protein.

13. A recombinantly expressed SM38 polypeptide encoded by a nucleic acid molecule that binds over the full length to the complement nucleotide sequence of a nucleotide sequence that encodes:
  (i) the SM38 amino acid sequence of FIG. 13A (SEQ ID NO: 5);
  (ii) the SM38 amino acid sequence of FIG. 13A (SEQ ID NO: 5) having a deletion of one or more amino acids between 1-19;
  (iii) the SM38 amino acid sequence of FIG. 13A (SEQ ID NO: 5) having a deletion of one or more amino acids between 276-303; or
  (iv) the SM38 amino acid sequence of FIG. 13A (SEQ ID NO: 5) having a deletion of one or more amino acids between 1-19 and 276-303 wherein said binding takes place in 0.5 M $NaHPO_4$, 7% sodium dodecyl sulfate (SDS), 1 mM EDTA at 65° C., and washing in 0.1×SSC/0.1% SDS at 68° C.

14. The recombinantly expressed SM38 polypeptide of claim 13 comprising:
  (i) the amino acid sequence of FIG. 13A (SEQ ID NO: 5);
  (ii) the amino acid sequence of FIG. 13A (SEQ ID NO: 5) having a deletion of one or more amino acids between 1-19;
  (iii) the amino acid sequence of FIG. 13A (SEQ ID NO: 5) having a deletion of one or more amino acids between 276-303; or
  (iv) the amino acid sequence of FIG. 13A (SEQ ID NO: 5) having a deletion of one or more amino acids between 1-19 and 276-303.

* * * * *

UNITED STATES PATENT AND TRADEMARK OFFICE
CERTIFICATE OF CORRECTION

PATENT NO. : 8,084,035 B2
APPLICATION NO. : 12/703062
DATED : December 27, 2011
INVENTOR(S) : Frances E. Lund et al.

Page 1 of 1

It is certified that error appears in the above-identified patent and that said Letters Patent is hereby corrected as shown below:

In the Specification:

Column 1, after the title, please insert:

--FEDERAL FUNDING--

--This invention was made with government support under grant/contract number AI043629 awarded by the National Institutes of Health. The government has certain rights to the invention.--

Signed and Sealed this
First Day of October, 2013

Teresa Stanek Rea
*Deputy Director of the United States Patent and Trademark Office*

SEQUENCE LISTING

```
<160> NUMBER OF SEQ ID NOS: 15

<210> SEQ ID NO 1
<211> LENGTH: 1034
<212> TYPE: DNA
<213> ORGANISM: S. mansoni

<400> SEQUENCE: 1
ggcacgaggt tattttttcac aatcttttaa ttcaaataat gatgaacgta atattgtttc      60
ttactttatc aaatattttt gtctttaact ctgcacaaca tcaaataaac ttacttagtg     120
aaatagtaca atcacgatgt actcagtgga aggttgaaca tggagctact aatataagtt     180
gtagtgagat ctggaattca tttgaaagca ttttactttc aactcatact aaatcagcat     240
gtgttatgaa atcagggtta ttcgatgatt ttgtttatca attgtttgaa ttggaacaac     300
aacaacaaca gcgacaccac acaattcaaa cggaacaata cttccattct caagtgatga     360
acatcattcg tggaatgtgt aaacgtcttg gagtatgtcg ttctctagaa actacatttc     420
caggatatct gtttgatgaa ttgaattggt gtaatggcag tttaacaggc aacacaaaat     480
acgggactgt atgtggatgc gattataaaa gtaatgttgt tcatgcgttc tggcaaagtg     540
```

-continued

```
cttcggctga gtatgccagg agagcatctg gtaacatctt tgtggtactg aatggctcgg     600
tcaaagctcc atttaatgaa ataaaactt  ttggaaaaat agaactacca ttgttaaaac     660
atcctcgagt acaacaatta acagtgaaat tagttcatag tttggaagat gtaaataacc     720
gacaaacatg tgaatcgtgg agtctgcaag aacttgcaaa caagctgaac tctgtacata     780
ttccttttcg ttgcattgac gatcctttag agttcagaca ttatcaatgc attgaaaatc     840
ctggcaaaca actatgtcag ttttcagctt cgacgaggtc aaacgtcgag acattactca     900 tacttttttcc gctagtcatt tgtttaactt tttatacttc catgaattga ataactttt     960 cagaactaaa ctttgaacag agaaagagaa caatgataat aaaggaatag acattaaaa    1020 aaaaaaaaaa aaaa                                                     1034
```

<210> SEQ ID NO 2
<211> LENGTH: 316
<212> TYPE: PRT
<213> ORGANISM: S. mansoni

<400> SEQUENCE: 2

```
Arg His Glu Val Ile Phe His Asn Leu Leu Ile Gln Ile Met Met Asn
1               5                   10                  15

Val Ile Leu Phe Leu Thr Leu Ser Asn Ile Phe Val Phe Asn Ser Ala
            20                  25                  30

Gln His Gln Ile Asn Leu Leu Ser Glu Ile Val Gln Ser Arg Cys Thr
        35                  40                  45

Gln Trp Lys Val Glu His Gly Ala Thr Asn Ile Ser Cys Ser Glu Ile
    50                  55                  60

Trp Asn Ser Phe Glu Ser Ile Leu Leu Ser Thr His Thr Lys Ser Ala
65                  70                  75                  80

Cys Val Met Lys Ser Gly Leu Phe Asp Asp Phe Val Tyr Gln Leu Phe
                85                  90                  95

Glu Leu Glu Gln Gln Gln Gln Arg His His Thr Ile Gln Thr Glu
            100                 105                 110

Gln Tyr Phe His Ser Gln Val Met Asn Ile Ile Arg Gly Met Cys Lys
        115                 120                 125

Arg Leu Gly Val Cys Arg Ser Leu Glu Thr Thr Phe Pro Gly Tyr Leu
    130                 135                 140

Phe Asp Glu Leu Asn Trp Cys Asn Gly Ser Leu Thr Gly Asn Thr Lys
145                 150                 155                 160

Tyr Gly Thr Val Cys Gly Cys Asp Tyr Lys Ser Asn Val Val His Ala
                165                 170                 175

Phe Trp Gln Ser Ala Ser Ala Glu Tyr Ala Arg Arg Ala Ser Gly Asn
            180                 185                 190

Ile Phe Val Val Leu Asn Gly Ser Val Lys Ala Pro Phe Asn Glu Asn
        195                 200                 205

Lys Thr Phe Gly Lys Ile Glu Leu Pro Leu Leu Lys His Pro Arg Val
    210                 215                 220

Gln Gln Leu Thr Val Lys Leu Val His Ser Leu Glu Asp Val Asn Asn
225                 230                 235                 240

Arg Gln Thr Cys Glu Ser Trp Ser Leu Gln Glu Leu Ala Asn Lys Leu
                245                 250                 255

Asn Ser Val His Ile Pro Phe Arg Cys Ile Asp Asp Pro Leu Glu Phe
            260                 265                 270

Arg His Tyr Gln Cys Ile Glu Asn Pro Gly Lys Gln Leu Cys Gln Phe
        275                 280                 285
```

```
Ser Ala Ser Thr Arg Ser Asn Val Glu Thr Leu Leu Ile Leu Phe Pro
    290                 295                 300

Leu Val Ile Cys Leu Thr Phe Tyr Thr Ser Met Asn
305                 310                 315

<210> SEQ ID NO 3
<211> LENGTH: 19
<212> TYPE: PRT
<213> ORGANISM: S. mansoni

<400> SEQUENCE: 3

Asn Asn Phe Ser Glu Leu Asn Phe Glu Gln Arg Lys Arg Thr Met Ile
1               5                   10                  15

Ile Lys Glu

<210> SEQ ID NO 4
<211> LENGTH: 8
<212> TYPE: PRT
<213> ORGANISM: S. mansoni

<400> SEQUENCE: 4

Asp Ile Lys Lys Lys Lys Lys Lys
1               5

<210> SEQ ID NO 5
<211> LENGTH: 303
<212> TYPE: PRT
<213> ORGANISM: S. mansoni

<400> SEQUENCE: 5

Met Met Asn Val Ile Leu Phe Leu Thr Leu Ser Asn Ile Phe Val Phe
1               5                   10                  15

Asn Ser Ala Gln His Gln Ile Asn Leu Leu Ser Glu Ile Val Gln Ser
            20                  25                  30

Arg Cys Thr Gln Trp Lys Val Glu His Gly Ala Thr Asn Ile Ser Cys
        35                  40                  45

Ser Glu Ile Trp Asn Ser Phe Glu Ser Ile Leu Leu Ser Thr His Thr
    50                  55                  60

Lys Ser Ala Cys Val Met Lys Ser Gly Leu Phe Asp Asp Phe Val Tyr
65                  70                  75                  80

Gln Leu Phe Glu Leu Glu Gln Gln Gln Gln Arg His His Thr Ile
                85                  90                  95

Gln Thr Glu Gln Tyr Phe His Ser Gln Val Met Asn Ile Ile Arg Gly
            100                 105                 110

Met Cys Lys Arg Leu Gly Val Cys Arg Ser Leu Glu Thr Thr Phe Pro
        115                 120                 125

Gly Tyr Leu Phe Asp Glu Leu Asn Trp Cys Asn Gly Ser Leu Thr Gly
    130                 135                 140

Asn Thr Lys Tyr Gly Thr Val Cys Gly Cys Asp Tyr Lys Ser Asn Val
145                 150                 155                 160

Val His Ala Phe Trp Gln Ser Ala Ser Ala Glu Tyr Ala Arg Arg Ala
                165                 170                 175

Ser Gly Asn Ile Phe Val Val Leu Asn Gly Ser Val Lys Ala Pro Phe
            180                 185                 190

Asn Glu Asn Lys Thr Phe Gly Lys Ile Glu Leu Pro Leu Leu Lys His
        195                 200                 205

Pro Arg Val Gln Gln Leu Thr Val Lys Leu Val His Ser Leu Glu Asp
    210                 215                 220
```

Val Asn Asn Arg Gln Thr Cys Glu Ser Trp Ser Leu Gln Glu Leu Ala
225                 230                 235                 240

Asn Lys Leu Asn Ser Val His Ile Pro Phe Arg Cys Ile Asp Asp Pro
            245                 250                 255

Leu Glu Phe Arg His Tyr Gln Cys Ile Glu Asn Pro Gly Lys Gln Leu
        260                 265                 270

Cys Gln Phe Ser Ala Ser Thr Arg Ser Asn Val Glu Thr Leu Leu Ile
    275                 280                 285

Leu Phe Pro Leu Val Ile Cys Leu Thr Phe Tyr Thr Ser Met Asn
    290                 295                 300

<210> SEQ ID NO 6
<211> LENGTH: 258
<212> TYPE: PRT
<213> ORGANISM: A. californica

<400> SEQUENCE: 6

Ile Val Pro Thr Arg Glu Leu Glu Asn Val Phe Leu Gly Arg Cys Lys
1               5                   10                  15

Asp Tyr Glu Ile Thr Arg Tyr Leu Asp Ile Leu Pro Arg Val Arg Ser
            20                  25                  30

Asp Cys Ser Ala Leu Trp Lys Asp Phe Phe Lys Ala Phe Ser Phe Lys
        35                  40                  45

Asn Pro Cys Asp Leu Asp Leu Gly Ser Tyr Lys Asp Phe Phe Thr Ser
    50                  55                  60

Ala Gln Gln Gln Leu Pro Lys Asn Lys Val Met Phe Trp Ser Gly Val
65                  70                  75                  80

Tyr Asp Glu Ala His Asp Tyr Ala Asn Thr Gly Arg Lys Tyr Ile Thr
            85                  90                  95

Leu Glu Asp Thr Leu Pro Gly Tyr Met Leu Asn Ser Leu Val Trp Cys
        100                 105                 110

Gly Gln Arg Ala Asn Pro Gly Phe Asn Glu Lys Val Cys Pro Asp Phe
    115                 120                 125

Lys Thr Cys Pro Val Gln Ala Arg Glu Ser Phe Trp Gly Met Ala Ser
    130                 135                 140

Ser Ser Tyr Ala His Ser Ala Glu Gly Glu Val Thr Tyr Met Val Asp
145                 150                 155                 160

Gly Ser Asn Pro Lys Val Pro Ala Tyr Arg Pro Asp Ser Phe Phe Gly
            165                 170                 175

Lys Tyr Glu Leu Pro Asn Leu Thr Asn Lys Val Thr Arg Val Lys Val
        180                 185                 190

Ile Val Leu His Arg Leu Gly Lys Ile Ile Glu Lys Cys Gly Ala
        195                 200                 205

Gly Ser Leu Leu Asp Leu Glu Lys Leu Val Lys Ala Lys His Phe Ala
    210                 215                 220

Phe Asp Cys Val Glu Asn Pro Arg Ala Val Leu Phe Leu Leu Cys Ser
225                 230                 235                 240

Asp Asn Pro Asn Ala Arg Glu Cys Arg Leu Ala Lys Arg Phe Tyr Arg
            245                 250                 255

Ile Ala

<210> SEQ ID NO 7
<211> LENGTH: 300
<212> TYPE: PRT
<213> ORGANISM: Homo sapiens

<400> SEQUENCE: 7

```
Met Ala Asn Cys Glu Phe Ser Pro Val Ser Gly Asp Lys Pro Cys Cys
1               5                   10                  15
Arg Leu Ser Arg Arg Ala Gln Leu Cys Leu Gly Val Ser Ile Leu Val
            20                  25                  30
Leu Ile Leu Val Val Val Leu Ala Val Val Pro Arg Trp Arg Gln
        35                  40                  45
Thr Trp Ser Gly Pro Gly Thr Thr Lys Arg Phe Pro Glu Thr Val Leu
 50                  55                  60
Ala Arg Cys Val Lys Tyr Thr Glu Ile His Pro Glu Met Arg His Val
65                  70                  75                  80
Asp Cys Gln Ser Val Trp Asp Ala Phe Lys Gly Ala Phe Ile Ser Lys
                85                  90                  95
His Pro Cys Asn Ile Thr Glu Glu Asp Tyr Gln Pro Leu Met Lys Leu
            100                 105                 110
Gly Thr Gln Thr Val Pro Cys Asn Lys Ile Leu Leu Trp Ser Arg Ile
        115                 120                 125
Lys Asp Leu Ala His Gln Phe Thr Gln Val Gln Arg Asp Met Phe Thr
130                 135                 140
Leu Glu Asp Thr Leu Leu Gly Tyr Leu Ala Asp Asp Leu Thr Trp Cys
145                 150                 155                 160
Gly Glu Phe Asn Thr Ser Lys Ile Asn Tyr Gln Ser Cys Pro Asp Trp
                165                 170                 175
Arg Lys Asp Cys Ser Asn Asn Pro Val Ser Val Phe Trp Lys Thr Val
            180                 185                 190
Ser Arg Arg Phe Ala Glu Ala Ala Cys Asp Val Val His Val Met Leu
        195                 200                 205
Asn Gly Ser Arg Ser Lys Ile Phe Asp Lys Asn Ser Thr Phe Gly Ser
210                 215                 220
Val Glu Val His Asn Leu Gln Pro Glu Lys Val Gln Thr Leu Glu Ala
225                 230                 235                 240
Trp Val Ile His Gly Gly Arg Glu Asp Ser Arg Asp Leu Cys Gln Asp
                245                 250                 255
Pro Thr Ile Lys Glu Leu Glu Ser Ile Ser Lys Arg Asn Ile Gln
            260                 265                 270
Phe Ser Cys Lys Asn Ile Tyr Arg Pro Asp Lys Phe Leu Gln Cys Val
        275                 280                 285
Lys Asn Pro Glu Asp Ser Ser Cys Thr Ser Glu Ile
290                 295                 300
```

<210> SEQ ID NO 8
<211> LENGTH: 318
<212> TYPE: PRT
<213> ORGANISM: Homo sapiens

<400> SEQUENCE: 8

```
Met Ala Ala Gln Gly Cys Ala Ala Ser Arg Leu Leu Gln Leu Leu Leu
1               5                   10                  15
Gln Leu Leu Leu Leu Leu Leu Leu Ala Ala Gly Gly Ala Arg Ala
            20                  25                  30
Arg Trp Arg Ala Glu Gly Thr Ser Ala His Leu Arg Asp Ile Phe Leu
        35                  40                  45
Gly Arg Cys Ala Glu Tyr Arg Ala Leu Leu Ser Pro Glu Gln Arg Asn
50                  55                  60
Lys Asn Cys Thr Ala Ile Trp Glu Ala Phe Lys Val Ala Leu Asp Lys
```

```
                65                  70                  75                  80
Asp Pro Cys Ser Val Leu Pro Ser Asp Tyr Asp Leu Phe Ile Asn Leu
                    85                  90                  95

Ser Arg His Ser Ile Pro Arg Asp Lys Ser Leu Phe Trp Glu Asn Ser
                100                 105                 110

His Leu Leu Val Asn Ser Phe Ala Asp Asn Thr Arg Phe Met Pro
            115                 120                 125

Leu Ser Asp Val Leu Tyr Gly Arg Val Ala Asp Phe Leu Ser Trp Cys
        130                 135                 140

Arg Gln Lys Asn Asp Ser Gly Leu Asp Tyr Gln Ser Cys Pro Thr Ser
145                 150                 155                 160

Glu Asp Cys Glu Asn Asn Pro Val Asp Ser Phe Trp Lys Arg Ala Ser
                165                 170                 175

Ile Gln Tyr Ser Lys Asp Ser Ser Gly Val Ile His Val Met Leu Asn
                180                 185                 190

Gly Ser Glu Pro Thr Gly Ala Tyr Pro Ile Lys Gly Phe Phe Ala Asp
            195                 200                 205

Tyr Glu Ile Pro Asn Leu Gln Lys Glu Lys Ile Thr Arg Ile Glu Ile
        210                 215                 220

Trp Val Met His Glu Ile Gly Pro Asn Val Glu Ser Cys Gly Glu
225                 230                 235                 240

Gly Ser Met Lys Val Leu Glu Lys Arg Leu Lys Asp Met Gly Phe Gln
                245                 250                 255

Tyr Ser Cys Ile Asn Asp Tyr Arg Pro Val Lys Leu Leu Gln Cys Val
                260                 265                 270

Asp His Ser Thr His Pro Asp Cys Ala Leu Lys Ser Ala Ala Ala Ala
            275                 280                 285

Thr Gln Arg Lys Ala Pro Ser Leu Tyr Thr Glu Gln Arg Ala Gly Leu
        290                 295                 300

Ile Ile Pro Leu Phe Leu Val Leu Ala Ser Arg Thr Gln Leu
305                 310                 315

<210> SEQ ID NO 9
<211> LENGTH: 282
<212> TYPE: PRT
<213> ORGANISM: A. californica

<400> SEQUENCE: 9

Met Ser Pro Val Ala Ile Val Ala Cys Val Cys Leu Ala Val Thr Leu
1               5                   10                  15

Thr Arg Ile Ser Pro Ser Glu Ala Ile Phe Pro Thr Pro Glu Leu Gln
                20                  25                  30

Asn Val Phe Leu Gly Arg Cys Lys Asp Tyr Glu Ile Thr Arg Tyr Leu
            35                  40                  45

Thr Ile Leu Pro Arg Val Lys Ser Asp Cys Arg Ala Leu Trp Thr Asn
        50                  55                  60

Phe Phe Lys Ala Phe Ser Phe Lys Ala Pro Cys Asn Leu Asp Leu Gly
65                  70                  75                  80

Ser Tyr Lys Asp Phe Phe Gln Arg Ala Gln Gln Thr Leu Pro Lys Asn
                85                  90                  95

Lys Val Met Phe Trp Ser Gly Val Tyr Asp Glu Ala His Asp Phe Ala
                100                 105                 110

Asp Asp Gly Arg Lys Tyr Ile Thr Leu Glu Asp Thr Leu Pro Gly Tyr
            115                 120                 125

Met Leu Asn Ser Leu Val Trp Cys Gly Gln Arg Asp Lys Pro Gly Phe
```

```
                130                 135                 140
Asn Gln Lys Val Cys Pro Asp Phe Lys Asp Cys Pro Val Gln Ala Arg
145                 150                 155                 160

Glu Ser Phe Trp Gly Thr Ala Ser Ser Tyr Ala His Ser Ala Glu
                165                 170                 175

Gly Asp Val Thr Tyr Met Val Asp Gly Ser Asn Pro Lys Val Pro Ala
                180                 185                 190

Tyr Arg Pro Asp Ser Phe Phe Gly Lys Tyr Glu Leu Pro Asn Leu Thr
                195                 200                 205

Asn Lys Val Thr Lys Val Lys Val Ile Val Leu His Gln Leu Gly Gln
210                 215                 220

Lys Ile Ile Glu Arg Cys Gly Ala Gly Ser Leu Leu Asp Leu Glu Met
225                 230                 235                 240

Val Val Lys Ala Lys Lys Phe Gly Phe Asp Cys Val Glu Asn Pro Lys
                245                 250                 255

Ser Val Leu Phe Leu Cys Ala Asp Asn Pro Asn Ala Arg Glu Cys
                260                 265                 270

Gln Leu Ala Lys Arg Tyr Tyr Arg Ile Ala
                275                 280

<210> SEQ ID NO 10
<211> LENGTH: 299
<212> TYPE: PRT
<213> ORGANISM: S. japonicum

<400> SEQUENCE: 10

Met Asn Ile Met Leu Ser Phe Ile Leu Leu Asn Ile Ile Thr Ala
1               5                   10                  15

Ala Val Gln Cys Gln Arg Asn Phe Phe Ala Asp Ile Val Ile Ser Arg
                20                  25                  30

Cys Ile Leu Trp Thr Val Thr His Asn Ile Thr Asn Val Asn Cys Val
                35                  40                  45

Asp Val Trp Ser Ser Phe Glu Lys Thr Leu Leu Ser Ile Ser Asn Gln
                50                  55                  60

Ser Glu Cys Ile Val Gln Ser Gln Leu Phe Asp Asn Phe Val His Lys
65                  70                  75                  80

Thr Phe Glu Met Gln Gln Pro Asn Gln Ser Gly Gln Tyr Phe His
                85                  90                  95

Ser Gln Val Thr His Val Ile Arg Gly Met Cys Lys Arg Leu Gly Val
                100                 105                 110

Cys Arg Ser Leu Glu Thr Thr Phe Pro Gly Tyr Leu Phe Asp Glu Leu
                115                 120                 125

Asp Trp Cys Asn Asn Ser Leu Ile Asp Ser Ser His Tyr Gly Thr Val
                130                 135                 140

Cys Lys Cys Asp Tyr Tyr Asn Gly Val Ile Asn Ala Phe Trp Lys Ser
145                 150                 155                 160

Ala Ser Ala Glu Tyr Ala Arg Arg Ala Ser Gly Thr Ile Phe Val Val
                165                 170                 175

Leu Asn Gly Ser Ala Lys Leu Pro Phe Asn Glu Asn Arg Thr Phe Gly
                180                 185                 190

Ser Val Glu Leu Pro Gln Leu Lys Tyr Pro Val Lys Gln Leu Ile
                195                 200                 205

Val Lys Leu Ile His Asn Leu Glu Asp Ser Ile Pro Arg His Thr Cys
210                 215                 220

Glu Ser Ile Asn Leu Leu Arg Leu Ser Ser Lys Val Lys Ser Ser Asn
```

```
                        225                 230                 235                 240
Ile Ser Phe Ser Cys Ile Asn Asp Pro Leu Glu Phe Lys His Tyr Gln
                245                 250                 255

Cys Ile Gln Asn Pro Phe Asn Lys Gln Cys Arg Phe Ala Ser Ser Ala
            260                 265                 270

Asn Ser Asn Arg Phe Lys Thr Leu Leu Leu Ser Ser Leu Phe Ile
        275                 280                 285

Cys Ser Ile Thr Asn Ser Phe Cys Arg Leu Asn
    290                 295

<210> SEQ ID NO 11
<211> LENGTH: 909
<212> TYPE: DNA
<213> ORGANISM: S. masoni
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
```

-continued

```
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
```

```
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
```

```
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
```

```
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
```

```
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
```

```
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (840)..(840)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
```

```
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (879)..(879)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t

<400> SEQUENCE: 11
atgatgaayg tnathytntt yytnacnytn wsnaayatht tygtnttyaa ywsngcncar      60
caycaratha ayytnytnws ngarathgtn carwsnmgnt gyacncartg gaargtngar     120
cayggngcna cnaayathws ntgywsngar athtggaayw snttygarws nathytnytn     180
wsnacncaya cnaarwsngc ntgygtnatg aarwsnggny tntttygayga yttygtntay    240 carytnttyg arytngarca rcarcarcar carmgncayc ayacnathca racngarcar    300
tayttycayw sncargtnat gaayathath mgnggnatgt gyaarmgnyt nggngtntgy     360
mgnwsnytng aracnacntt yccnggntay ytnttygayg arytnaaytg gtgyaayggn    420
wsnytnacng gnaayacnaa rtayggnacn gtntgyggnt gygaytayaa rwsnaaygtn    480
gtncaygcnt tytggcarws ngcnwsngcn gartaygcnm gnmgngcnws nggnaayath    540
ttygtngtny tnaayggnws ngtnaargcn ccnttyaayg araayaarac nttyggnaar    600
athgarytnc cnytnytnaa rcayccnmgn gtncarcary tnacngtnaa rytngtncay    660
wsnytngarg aygtnaayaa ymgncaracn tgygarwsnt ggwsnytnca rgarytngcn    720
aayaarytna aywsngtnca yathccntty mgntgyathg aygayccnyt ngarttymgn    780
caytaycart gyathgaraa yccnggnaar carytntgyc arttywsngc nwsnacnmgn    840
wsnaaygtng aracnytnyt nathytntty ccnytngtna thtgyytnac nttytayacn    900 wsnatgaay                                                            909

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 12
acatctttgt ggtactgaat ggctcgg                                         27

<210> SEQ ID NO 13
```

```
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 13
tgagtaatgt ctcgacgttt gacctcg                                              27

<210> SEQ ID NO 14
<211> LENGTH: 27
<212> TYPE: DNA
<213> ORGANISM: artificial Sequence
<220> FEATURE:
<223> OTHER INFORMATION: Oligonucleotide primer

<400> SEQUENCE: 14
catcgaataa ccctgatttc ataacac                                              27

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 15
gataaagtaa gaactcgtgc c                                                    21
```